(12) United States Patent
Nazare et al.

(10) Patent No.: US 7,365,088 B2
(45) Date of Patent: Apr. 29, 2008

(54) INDAZOLE-DERIVATIVES AS FACTOR XA INHIBITORS

(75) Inventors: Marc Nazare, Idstein (DE); Volkmar Wehner, Sandberg (DE); Volker Laux, Mainz (DE); Matthias Urmann, Eschborn (DE); Armin Bauer, Sulzbach (DE); Hans Matter, Langenselbold (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 616 days.

(21) Appl. No.: 10/849,088

(22) Filed: May 19, 2004

(65) Prior Publication Data

US 2004/0235824 A1 Nov. 25, 2004

Related U.S. Application Data

(60) Provisional application No. 60/507,171, filed on Sep. 30, 2003.

(30) Foreign Application Priority Data

Sep. 30, 2003 (EP) ................................ 60/507,171

(51) Int. Cl.
- A16K 31/42 (2006.01)
- A16K 31/4152 (2006.01)
- C07D 261/20 (2006.01)
- C07D 413/14 (2006.01)

(52) U.S. Cl. ...................................... 514/378; 548/247
(58) Field of Classification Search ................ 514/378; 548/247
See application file for complete search history.

(56) References Cited

U.S. PATENT DOCUMENTS

| | | | |
|---|---|---|---|
| 5,998,424 | A | 12/1999 | Galemmo et al. |
| 6,339,099 | B1 | 1/2002 | Lam et al. |
| 6,906,084 | B2 | 6/2005 | Nazaré et al. |
| 6,953,857 | B2 | 10/2005 | Nazaré et al. |
| 7,067,665 | B2 | 6/2006 | Nazaré et al. |
| 2004/0171604 | A1 | 9/2004 | Nazaré et al. |
| 2004/0204406 | A1 | 10/2004 | Nazaré et al. |
| 2005/0009827 | A1 | 1/2005 | Nazaré et al. |
| 2005/0009828 | A1 | 1/2005 | Nazaré et al. |
| 2005/0009829 | A1 | 1/2005 | Nazaré et al. |
| 2005/0033049 | A1 | 2/2005 | Nazaré et al. |
| 2005/0043302 | A1 | 2/2005 | Nazaré et al. |
| 2007/0049573 | A1 | 3/2007 | Bauer et al. |
| 2007/0179122 | A1 | 8/2007 | Urmann et al. |

FOREIGN PATENT DOCUMENTS

| | | |
|---|---|---|
| EP | 0987274 | 3/2000 |
| WO | WO 92/06711 | 4/1992 |
| WO | WO 95/29189 | 11/1995 |
| WO | WO 96/12800 | 5/1996 |
| WO | WO 97/47651 | 12/1997 |
| WO | WO 00/39131 | 7/2000 |
| WO | WO01/07436 | 2/2001 |
| WO | WO 01/70678 | 9/2001 |
| WO | WO 02/00647 A1 | 1/2002 |

OTHER PUBLICATIONS

Abdel-Khalik, et al., Studies with Functionally Substituted Heteroaromatics: The Chemistry of N-Phenylhydra-onylalkylpyridinium Salts and of Phenylhydrazonylalkylbenzoazoles, Synthesis; 8; 2000; pp. 1166-1169.

Adang, Anton E. P. et al., A New Generation of Orally Active Antithrombotics: Comparing Strategies in the GPIIb/IIIa, Thrombin and Factor Xa Areas, Drugs of the Future, (2000), vol. 24, No. 4, pp. 369-383.

Adger, et al., 1,2,3-Benzotriazines, J. Chem. Soc.; Perkin Trans. 1; 1975; pp. 31-40.

Ahluwalia, et al., A Facile Synthesis of Pyrazolo[3,4-b]Pyridines, Synthetic Comm.; 26(7); 1996; pp. 1341-1348.

Articio, et al., Aromatic Hydrazides As Specific Inhibitors Of Bovine Serum Amine Oxidase, Eur. J. Med. Chem. Chim. Ther. (1992),27, 219-228.

Ashton Wallace T. et al., A Regioselective Route To 3-Alkyl-l-aryl-1H-Pyrazole-5-carboxylates: Synthetic Studies And Structureal Assignments, J. Heterocyclic Chem., (1993), vol. 30, pp. 307-311.

Auzzi, et al., Alogenazlone DI Alcuni Derivati Pirazolo [1,5-a]Pirimidinici, Ed Sci (1979), 34, 743.

(Continued)

Primary Examiner—Taofiq Solola
(74) Attorney, Agent, or Firm—Jiang Lin

(57) ABSTRACT

The present invention relates to a compound of the formula I

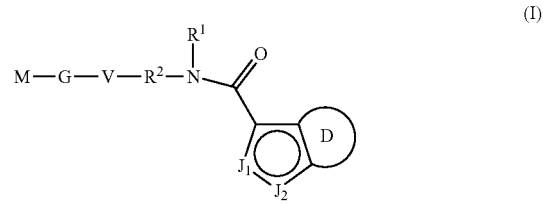

wherein $J_1$, $J_2$, $R^0$, $R^1$, $R^2$, Q, V, G and M are as defined herein. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

11 Claims, No Drawings

OTHER PUBLICATIONS

Baraldi, et al., A New Synthethic Approach to Indazole Synthesis, Synthesis; 1997; pp. 1140-1142.

Bravo Plerfrancesco et al., An Efficient Entry To Perfluoroalkyl Substituted Azoles Starting From Beta-Perfluoroalkyl-Beta-Dicarbonyl Compounds, Tetrahedron, (1994), vol. 50, No. 29, pp. 8827-8836.

Buchwald, et al., A General And Efficient Copper Catalyst For The Amidation Of Aryl Halides And the N-Arylation of Nitrogen Heterocycles, J. Am. Chem. Soc. 2001, 123, 7727-7729.

Butler, et al., New General Methods for the Substitution of 5-Chloropyrazoles. The Synthesis of 1,3-Dialkyl-5-chloropyrazol-4-yl Aryl Ketones and New 1,3-Dialkyl-2-pyrazolin-5-ones, J. Org. Chem. (1971) 36(17), 2542-2547.

Cardia, et al, Synthesis of New Arylidencycloalkylpyrazoles of Potential Biological Interest, J. Heterocyclic Chem.; 40; 2003; pp. 309-315.

Cardia, et al., New Cyclooalkylpyrazoles as Potential Cyclooxygenase Inhibitors, II Farmaco; 53; 1998; pp. 698-708.

Caron, et al., A Versatile and Efficient Synthesis of Substituted 1H-Indazoles, Synthesis; 4; 1999; pp. 588-592.

Cerrada, et al., Synthesis Of p-Nitrophenylazoles By Phase Transfer Catalysis Without Solvent, Synth. Commun (1993), 23(14) 1947-1952.

Chan, et al., New N- and O-Arylations With Phenylboronic Acids And Cupric Acetate, Tetrahedron Letters 39 (1998) 2933-2936.

Cheng, et al, Relationship Between The Inhibition Constant (KI) And The Concentration Of Inhibitor Which Causes 50 Per Cent Inhibition (I50) Of An Enzymatic Reaction, Biochem. Pharmacol. (1973), 22, 3099-3108.

Collot, et al., First Combined Selective N- And C-Arylations With Boronic Acids: Application To The Synthesis Of 1,3-Diarylindazoles, Tetrahedron Letters (2000), 41, 9053-9057.

Connolly, et al., Synthesis and Progesterone Receptor Binding Affinity of Substituted 1-Phenyl-7-Benzyl-4,5,6,7-tetrahydor-1H-Indazoles, Bioorganic & Medicinal Chem. Lett. Oxford,GB; 7; 19; 1997; pp. 2551-2556.

Cooper, et al., 1,4 Dihydropyridines As Antagonists Of Platelet Activating Factor. 1. Synthesis And Structure-Activity Relationships of 2-(4-Heterocyclyl) Phenyl Derivatives, J. Med. Chem. (1992), 35, 3115-3129.

Cozzi, et al., Ethyl 2- {[5,6-Dihydro-7-(1H-Imidazol-1-YL)-2-Naphthalenyl]Oxy-2-Methylpropanonate As A New Potent Oxyisobutyrate Hypolipidaemic With Unusual Features, Farmaco (1987) 42, 205-218.

Chemical Abstracts, Compounds for Screening, Database Chemcats; XP002256315; Apr. 29, 2003.

Dalcanale, et al., Selective Oxidation of Aldehydes to Carboxylic Acids with Sodium Chlorite-Hydrogen Peroxide, J. Org. Chem.; 51; 1996; pp. 567-569.

Dell'erba, et al., A Novel Approach to 1H-Indazoles via Arylazosulfides, Tetrahedron; 50(11); 1994; pp. 3529-3536.

Dennler, et al., Synthesis of Fused Heterocyclic Compounds with Polyphosphoric Acid, Ca. J. Chem.; 45; 1967; pp. 697-705.

Elnagdi Mohamed Hilmy et al., Recent Development In The Synthesis Of Pyrazole Derivatives, Heterocycles, (1985), vol. 23, No. 12, pp. 3121-3153.

Erian Ayman W. et al., Phosphonium Ylides In Organic Synthesis III 1,2 A Novel Synthese Of Alpha-Substituted Ylides And Pyrazole Systems, Synthetic Communications, (1999), vol. 29, No. 9, pp. 1527-1537.

Farina, et al., 1,3-Dipolar Cycloadditions With Methyl 4-Oxo and 4-Hydroxy-2-Butynoates. Synthesis Of Functionalized Pyrazoles And Triazoles, Heterocycles (1989) 29, 967.

Ferrari, et al., An Improved Synthesis of indazole-3-carboxylic Acid, J. Heterocyclic Chem.; 26; 1989; pp. 531-532.

Foti, et al., First Synthesis Of A Bromonitrilimine. Direct Formation of 3-Bromopyrazole Derivatives., Tetrahedron Letters (1999) 40, 2605-2606.

Frasca A., Synthesis of Indazoles from Acetophenone p-Nitro-Phenylhydrazoles Using Polyphosphoric Acid as a Condensing Agent, Tetrahedron Letters; 24; 1962; pp. 1115-1119.

Fuchikami, et al., A Novel And Convenient Method For Trifluoromethylation Of Organic Halides Using CF3SiR'3/KF/Cu(1) System, Tetrahedron Lett. 1991, 32(1), 91-94.

Gardner, et al., A Versatile Approach to Analogues of the Cannabinoid-like Anti-emetic Nonabine, J. Heterocyclic Chem. 21, (1984) 121-127.

Gonzalez, et al., X-Ray Crystallographic Analysisof the Products of the High Temperature Reaction of 1-Phenyl-4-vinylpyrazoly with Dimethyl Acetylenedicarboxylate in a Scaind Vessel., J. Chem. Res.; 1985; pp. 1128-1136.

Grimmett, et al., Synthesis And Reactions Of Lithiated Monocyclic Azoles Containing Two Or More Hetero-Atoms. Part III: Pyrazoles, Heterocycles, 37(3), (1994) 2087-2147.

Halley, et al., Synthesis of 5-Cyanoindazole and 1-Methyl and 1-Aryl-5-Cyanoindazoles, Synth. Commun.; 27; 1997; pp. 1199-1207.

Haque Tasir S. et al., Parallel Synthesis Of Potent, Pyrazole-Based Inhibitors Of Helicobacter pylori Dihydroorotate Dehydrogenase, J. Med. Chem., (2002), vol. 45, pp. 4669-4678.

Harada, et al., Development of Potent Serotonin-3 (5-HT3) Receptor Antagonists., Chem. Pharm. Bull.; 43(11); 1995; pp. 1912-1930.

Hartwig, John, Ubergangsmetall-Katalysierte Synthese Von Arylaminen Und Arylethem Aus Arylhalogeniden Und—Triflaten: Anwendungen Und Reaktionsmechanismus, Angew. Chem. 1998, 110, 2154-2177.

Hartwig, et al., Room-Temperature Palladium-Catalyzed Amination of Aryl Bromides And Chlorides And Extended Scope Of Aromatic C-N Bond Formation With a Commercial Ligand, J. Org. Chem. (1999) 64, 5575-5580.

Heinisch Gottfried et al., Pyrazole Chemistry. Part 4 Directed Lithiation Of 4-Bromo-1-phenyl-sulphonylpyrazole: A Convenient Approach To Vicinally Disubstituted Pyrazoles, J. Chem. Soc. Perkin Trans., (1990), pp. 1829-1834.

Holzer, et al., N1-Substituted 3,5-Dimethoxy-4-Halogeno-1H-Pyrazoles: Synthesis and NMR Study, J. Heterocyclic Chem. 32, 1351 (1995).

Huang, et al., Regioselective Synthesis of 1,3,5-Triaryl-4-alkylpyrazoles: Novel Ligands For The Estrogen Receptor, Organic Letters, (2000) 2, (18), 2833-2836.

Huisgen, et al., Diazocarbonyl Compounds And 1-Diethylaminopropyne, American Chemical Society, (1979), vol. 101, No. 13, pp. 3647-3648.

Jeon, et al., Synthesis Of New 4-Benzoyl-5-Hydroxy-3-Trifluoromethylpyrazole Derivatives VIA [1,3]Rearrangements Of Benzoyl Group Using tert-Butyllithium, Synth. Commun. (1998), 28(12), 2159-2166.

Kang, et al., Copper-Catalyzed N-Arylation Of Aryl Iodides With Benzamides Or Nitrogen Heterocycles In The Presence Of Ethylenediamine, Synlett 2002, 3, 427-430.

Kudo, et al., Synthesis and Herbicidal Activity of 1,5-Diarylpyrazole Derivatives, Chem. Pharm. Bull.; 47(6); 1999; pp. 857-868.

Kwong, et al., Copper-Catalyzed Coupling Of Alkylamines And Aryl Iodides: An Efficient System Even In An Air Atmosphere, Organic Lett. 2002, 4 (4), 581-584.

Lam, et al., Copper-Catalyzed General C-N and C-O Bond Cross-Coupling With Arylboronic Acid, Tetrahedron Letters (2001) 42, 3415-3418.

Lam, et al., New Aryl/Heteroaryl C-N Bond Cross-coupling Reactions Via Arylboronic Acid/Cupric Acetate Arylation, Tetrahedron Letters 39 (1998) 2941-2944.

Makino, et al., Selective Fluorination of Ethyl 1-Methylpyrazole-4-carboxylates with Poly (Hydrogen Fluoride) -Amine Complex Under Electrolytic Anodic Oxidation, Journal of Fluorine Chemistry, 39 (1988) 435-440.

Makino, et al., Synthesis of Pyrazoles and Condensed Pyrazoles, J. Heterocycl. Chem.; 36; 1999; pp. 321-332.

Makino, et al., Synthesis of Pyrazoles, J. Heterocycl. Chem.; 35; 1998; pp. 489-497.

Mann, et al., Palladium-Catalyzed C-N(sp2) Bond Formation: N-Arylation Of Aromatic And Unsaturated Nitrogen And The Reductive Elimination Chemistry Of Palladium Azolyl And Methyleneamido Complexes, J. Am. Chem. Soc. (1998), 120, 827-828.

Markova, et al., Study of the reaction of 1-dialkylamino(alkoxy)-1-buten-3-ones with some 1,3-dipolar systems, Zhurnal Organicheskoi Khimii (1983), 19(11), 2281-5; Coden: Zorkae; ISSN: 0514-7492; See also—J.Org.Chem.USSR (Engl.Transl.), 1983, V.19, pp. 1990-1993 (ISSN: 0022-3271, Coden JOCYA9) (Beilstein Citation No. 5631936).

Martins Marcos A. et al., Haloacetylated Enol Ethers. 11 [16]. Synthesis Of 1-Methyl—And 1-Phenyl Pyrazole-3(5)-Ethyl Esters. A One-Pot Procedure, J. Heterocyclic Chem., (1999), vol. 36, pp. 217-220.

Martins Marcos A. P. et al., One-Pot Synthesis Of 3(5)-Ethoxycarbonylpyrazoles, Synthesis, (1995), pp. 1491-1492.

Morimoto, et al., Synthesis Of Halosulfuron-Methyl Via Selective Chlorination At 3- And/Or 5-Position Of Pyrazole-4-Carboxylates, J. Heterocycl. Chem. (1997) 34, 537.

Nagai Toshikazu et al., Recent Progress In The Preparation And Synthetic Uses Of The Reactions Of 3H-Pyrazoles A Review, Organic Preparations And Procedures Int, (1993), vol. 25, No. 4, pp. 403-435.

Nichols, et al., 1-(2,5-Dimethoxy-4-(Trifluoromethyl) Phenyl)-2-Aminopropane: A Potent Serotonin 5-HT2A/2C Agonist, J. Med. Chem. 1994,37, 4336-4351.

Norman, et al., Synthesis and Evaluation of Heterocyclic Carboxamides as Potential Antipsychotic Agents, J. Med. Chem.; 39; 1996; pp. 4692-4703.

Old David W et al., Efficient Palladium-Catalyzed N-Arylation of Indoles, Organic Letters, 2000, vol. 2, No. 10, pp. 1403-1406.

Padwa Albert et al., Reaction Of Hydrazonyl Chlorides And Carboalkoxymethylene Triphenylphosphoranes To Give 5-Alkoxy Substituted Pyrazoles, J. Heterocyclic, (1987), Vo. 24, pp. 1225-1227.

Patel Himatkumar V. et al., Concise And Efficient Synthesis Of 1h-Pyrazoles: Reaction Of [Hydroxy(Tosyloxy)Iodo]Benzene With Ethyl 2,3-Dioxobutanoate-2-Arylhydrazones, Synthetic Communications, (1991), vol. 21, No. 15-16, pp. 1583-1588.

Pawlas, et al., Synthesis Of 1-Hydroxy-Substituted Pyrazolo[3,4-c]- and Pyrazolo[4,3-c] Quinolines and -Isoquinolines From 4- and 5-Aryl-Substituted 1-Benzyloxypyrazoles, J. Org. Chem. 2000, 65, 9001-9006.

Pilling Garry M. et al., The Synthesis Of 1H-Pyrazol-4-OLS From 2-(2-Alkylidenehydrazino) Acetic Acids, Tetrahedron Letters, (1988), vol. 29, No. 12, pp. 1341-1342.

Prikhod'ko, et al., Croos-coupling of Copper Arylacetylides with N-(o-iodoaryl)hydrazines as a New Method of Synthesising 2-Substituted Indoles, Mendeleev Commun.; 4; 1998; pp. 149-150.

Qing, et al., First Synthesis Of Ortho-Trifluoromethylated Aryl Triflates, J. Chem Soc. Perkin Trans. I, 1997, 20, 3053-3057.

Ratajczyk, et al., The Cyclocondensation of 5-Amino-1,3-dimethylpyrazole with Ethyl Acetoacetate., J. Heterocycl. Chem.; 12; 1975; pp. 517-522.

Rodriguez-Franco, et al., A Mild And Efficient Method For The Regioselective Iodination Of Pyrazoles, Tetrahedron Letters, 42 (2001) 863-865.

Sakamoto, et al., Palladium-Catalyzed Cyanation Of Aryl and Heteroaryl Iodides With Copper (I) Cyanide, J. Chem. Soc. Perkin Trans I, 1999, 2323-2326.

Sall, et al., Use of Conformationally Restricted Benzamidines as Arginine Surrogates in the Design of Plateleet GPIIb-IIIa Receptor Antagonists, J. Med. Chem.; 40; 1997; pp. 2843-2857.

Sauer Daryl R. et al., The Synthesis Of 3(5)-[(2-Hydroxyethoxy)methyl]pyrazole-5(3)-carboxamide, An Acyclic Analogue Of 4-Deoxypyrazofurin, J. Org. Chem., (1990), vol. 55, pp. 5535-5538.

Segel Irwin H, Behavior and Analysis of Rapid Equilibrium and Steady-State Enzyme Systems, Enzyme Kinetics, 1975, John Wiley & Sons, New York, pp. 100-125.

Shutske, et al., Synthesis of Some Piperazinylpyrazolo[3,4-b]pyridines as Selective Serotonin Re-uptake Inhibitors, J. Heterocycl. Chem.; 34; 1997; pp. 789-795.

Smith, et al., Cyclopropanes. I. The Reaction Between Nitrocyclopropyl Ketones and Alkali, J. AM. Chem. Soc.; 71; 1949; pp. 2671-2676.

Song, et al., A Novel Synthesis of 2-Aryl-2H-Indazoles via a palladium-catalyzed Intramolecular Amination Reaction, Organic Lett.; 2; 4; 2000; pp. 519-521.

Song, et al., Synthesis of 1-aryl-1H-indazoles via the palladium-catalyzed cyclization of N-aryl-N'-(o-bromobenzyl)hydrazines and [N-aryl-N'-(o-bromobenzyl)-hydrazinato-N']-triphenylphosphonium bromides, Tetrahedron Letters; 42; 2001; pp. 2937-2940.

Storer, et al., The Synthesis And Antiviral Activity Of 4-Fluoro-1-Beta-D-Ribofuranosyl-1H-Pyrazole-3-Carboxamide, Nucleosides & Nucleotides, 18(2), 203-216 (1999).

Su, et al., Fibrinogen Receptor (GPIIb-IIIa) Antagonists Derived from 5,6-Bicyclic Templates., J. Med. Chem.; 40; 1997; pp. 4308-4318.

Su, et al., Methyl Chlorodifluoroacetate A Convenient Trifluoromethylating Agent, Tetrahedron Letters, (1991), 32(52), 7689-7690.

Sun, et al., Efficient Synthesis of 5-(Bromomethyl)- and 5-(Aminomethyl)-1-THP-Indazole, J. Org. Chem.; 62; 1997; pp. 5627-5629.

Tokmakov Gennadii P et al., Rearrangement of 1-Arylindoles to 5H-Dibenz[b,f]azepines, Tetrahedron, 1995, vol. 51, No. 7, pp. 2091-2098.

Tominaga, et al., Synthesis and Chemiluminescence of 1,3-Disubstituted Pyrazolo[4',3':5,6]Pyrido[2,3-d]Pyridazine-5,8(6H,7H)-Diones and Related Compounds, Tetrahedron Lett.; 36;47;1995; pp. 8641-8644.

Turnbull Kenneth et al., A Lithiation Approach TO 5-Substituted-1-Benzenesulfonylpyrazoles, OPPI Briefs, (2000), vol. 32, No. 6, pp. 593-603.

Turnbull, K., Acid Induced Reactions of a Sydnone Ketoxime, J. Heterocyclic Chem.; 25; 1988; pp. 1817-1819.

Turnbull, et al., Acylation of Sydnones with Acetic Anhydride in the Presence of Montmorillonite K-10, Synthetic Comm.; 26(14); 1996; pp. 2757-2764.

Umemoto, et al., Power And Structure-Variable Fluorinating Agents. The N-Fluoropyridinium Salt System, J. Am. Chem. Soc. (1990), 112, 8563-8575.

Unangst Paul C et al., Synthesis of Novel 1-Phenyl-1H-indole-2-carboxylic Acids. I. Utilization of Ullmann and Dieckmann Reactions for the Preparation of 3-Hydroxy, 3-Alkoxy, and 3-Alkyl Derivatives, J. Heterocyclic Chem., 1987, vol. 24, pp. 811-815.

Von Meyenburg, et al., Ueber eine neus Synthese von Derivaten des Isindazols, Chem. Berlin; 24; 1891; pp. 2370-2388.

Waiser, et al., Pentacycllic Triazolodiazepines as PAF-Antagonists, J. Heterocycl. Chem.; 28; 1991; pp. 1121-1125.

Wang, et al., Practical Synthesis Of 1,3-Diaryl-5-Alkylpyrazoles By A Highly Regioselective N-arylation Of 3,5-disubstituted Pyrazoles With 4-Fluoronitrobenzene, Tetrahedron Letters (2000), 41, 5321-5324.

Washizuka, et al., Novel Generation Of Azomethine Imines From Alpha-Silylnitrosamines by 1,4-Silatropic Shift And Their Cycloaddition, Tetrahedron Letters 40 (1999) 8849-8853.

Welch, et al, A Novel Synthesis of 3-Substituted Indazole Derivatives, Synthesis; 1992; pp. 937-939.

Wolfe, et al., Simple, Efficient Catalyst System For The Palladium-Catalyzed Amination Of Aryl Chlorides, Bromides, and Triflates, J. Org. Chem. 2000, 65, 1158-1174.

Yang, et al., Palladium-Catalyzed Amination Of Aryl Halides And Sulfonates, J. Organomet. Chem. 1999, 576, 125.

Yoshida, et al., Practical Synthesis of 1H-Indazole-3-Carboxylic Acid and its Derivatives, Heterocycles; 43; 12; 1996; pp. 2701-2712.

Zhang Jidong et al., Potent Nonpeptide Endothelin Antagonists: Synthesis And Structure-Activity Relationships Of Pyrazole-5-Carboxylic Acids, Bioorganic & Medicinal Chemistry Letters, (2000), vol. 10, pp. 2575-2578.

Zhenqi, et al., A New and Facile Synthesis of 1H-Indazoles, J. Chem. Soc. Perkin Trans.; 1; 1993; pp. 1279-1280.

Baraldi, et al., A New Synthethic Approach to Indazole Synthesis, Synthesis; (1997), pp. 1140-1142.

Booker-Milburn Kevin I., A Convenient Method for The Synthesis of C-5 Subsituted 1-Tosylpryazolas, Synlett; Apr. 1992; pp. 327-328.

Dewar, M. J. S., et al., Sulphanilamides of Some Aminopyrazoles and a Note on the Application of p-Phthalimidobenzenesulphonyl Chloride to the Synthesis of Sulphanilamides, J. Chem. Soc. (1945), pp. 114-116.

Jones R. G., et al., vic-Dicarboxylic Acid Derivatives of Pyrazole, Isoxazole, and Pyrimidine, J. Org. Chem. (1995), 20, 1342-1347.

Sucrow, et al., Stable Pyrazollum Betaines by Addition of 1,1-Dialkyl-hydrazines to Acetylenecarboxylic Esters, Angew Chem, Intl. Ed. (1975); vol. 14:8 pp. 560-561.

INDAZOLE-DERIVATIVES AS FACTOR XA INHIBITORS

This application claims the benefit of U.S. Provisional Application No. 60/507,171, filed Sep. 30, 2003.

FIELD OF THE INVENTION

The present invention relates to a compound of formula I,

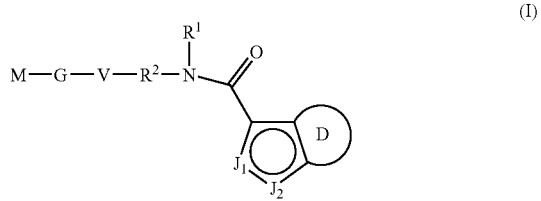

in which $J_1$, $J_2$, $R^1$, $R^2$, Q, V, G and M have the meanings indicated below. The compounds of the formula I are valuable pharmacologically active compounds. They exhibit a strong antithrombotic effect and are suitable, for example, for the therapy and prophylaxis of cardiovascular disorders like thromboembolic diseases or restenoses. They are reversible inhibitors of the blood clotting enzymes factor Xa (FXa) and/or factor VIIa (FVIIa), and can in general be applied in conditions in which an undesired activity of factor Xa and/or factor VIIa is present or for the cure or prevention of which an inhibition of factor Xa and/or factor VIIa is intended. The invention furthermore relates to processes for the preparation of compounds of the formula I, their use, in particular as active ingredients in pharmaceuticals, and pharmaceutical preparations comprising them.

BACKGROUND OF THE INVENTION

Normal haemeostasis is the result of a complex balance between the processes of clot initiation, formation and clot dissolution. The complex interactions between blood cells, specific plasma proteins and the vascular surface, maintain the fluidity of blood unless injury and blood loss occurs (EP-A-987274). Many significant disease states are related to abnormal haemeostasis. For example, local thrombus formation due to rupture of atheroslerotic plaque is a major cause of acute myocardial infarction and unstable angina. Treatment of an occlusive coronary thrombus by either thrombolytic therapy or percutaneous angioplasty may be accompanied by acute thrombolytic reclosure of the affected vessel.

There continues to be a need for safe and effective therapeutic anticoagulants to limit or prevent thrombus formation. It is most desirable to develop agents that inhibit coagulation without directly inhibiting thrombin but by inhibiting other steps in the coagulation cascade like factor Xa and/or factor VIIa activity. It is now believed that inhibitors of factor Xa carry a lower bleeding risk than thrombin inhibitors (A. E. P. Adang & J. B. M. Rewinkel, Drugs of the Future 2000, 25, 369-383). Low molecular weight, factor Xa-specific blood clotting inhibitors that are effective but do not cause unwanted side effects have been described, for example, in WO-A-95/29189.

However, besides being an effective factor Xa-specific blood clotting inhibitor, it is desirable that such inhibitors also have further advantageous properties, for instance stability in plasma and liver and selectivity versus other serine proteases whose inhibition is not intended, such as thrombin. There is an ongoing need for further low molecular weight factor Xa specific blood clotting inhibitors, which are effective and have the above advantages as well.

Specific inhibition of the factor VIIa/tissue factor catalytic complex using monoclonal antibodies (WO-A-92/06711) or a protein such as chloromethyl ketone inactivated factor VIIa (WO-A-96/12800, WO-A-97/47651) is an extremely effective means of controlling thrombus formation caused by acute arterial injury or the thrombotic complications related to bacterial septicemia There is also experimental evidence suggesting that inhibition of factor VIIa/tissue factor activity inhibits restenosis following balloon angioplasty. Bleeding studies have been conducted in baboons and indicate that inhibition of the factor VIIa/tissue factor complex has the widest safety window with respect to therapeutic effectiveness and bleeding risk of any anticoagulant approach tested including thrombin, platelet and factor Xa inhibition. Certain inhibitors of factor VIIa have already been described. EP-A-987274, for example discloses compounds containing a tripeptide unit, which inhibit factor VIIa However, the property profile of these compounds is still not ideal, and there is an ongoing need for further low molecular weight factor Via inhibitory blood clotting inhibitors The present invention satisfies the above needs by providing a novel compound of formula I, which exhibits better factor Xa and/or factor VIIA inhibitory activity and are favorable agents with high bioavailability.

SUMMARY OF THE INVENTION

The present invention relates to a compound of formula I,

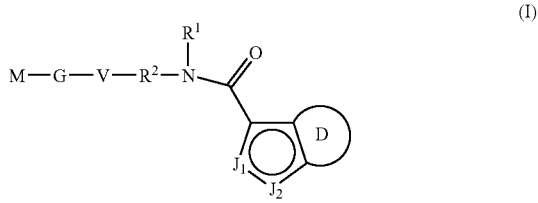

wherein:
one of $J_1$ and $J_2$ is N, and the other is N—Q—$R^0$,
$R^0$ is 1) a monocyclic or bicyclic 6- to 14-membered aryl, wherein aryl is mono-, di- or trisubstituted independently of one another by R8,
  2) a monocyclic or bicyclic 4- to 15-membered heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or
  3) a monocyclic or bicyclic 4- to 15-membered heterocyclyl, containing one, two, three or four heteroatoms chosen from nitrogen, sulfur or oxygen,
  wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen,
  wherein heterocyclyl is unsubstituted or mono-, di- or trisubstituted independently of one another by R8,
R8 is 1) halogen,
  2) —$NO_2$,
  3) —CN,
  4) —C(O)—$NH_2$,
  5) —OH,
  6) —$NH_2$,
  7) —O—$CF_3$
  8) a monocyclic or bicyclic 6- to 14-membered aryl, wherein aryl is mono-, di- or trisubstituted independently of one another by halogen or —O—($C_1$-$C_8$)-alkyl,
  9) —($C_1$-$C_8$)-alkyl, wherein alkyl is unsubstituted or mono-, di- or trisubstituted independently of one another by halogen, $NH_2$, —OH or a methoxy residue,
  10) —O—($C_1$-$C_8$)-alkyl, wherein alkyl is unsubstituted or mono-, di- or trisubstituted independently of one another by halogen, $NH_2$, —OH or a methoxy residue,
  11) —$SO_2$—$CH_3$ or
  12) —$SO_2$—$CF_3$,
  provided that R8 is at least one halogen, —C(O)—$NH_2$ or —O—($C_1$-$C_8$)-alkyl residue, if $R^0$ is a monocyclic or bicyclic 6- to 14-membered aryl,
  the substructure

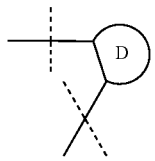

in formula I is
  a 4-to 8 membered saturated, partially unsaturated or aromatic cyclic group containing zero, 1, 2, 3 or 4 heteroatoms chosen from nitrogen, sulfur or oxygen and is unsubstituted or substituted 1, 2, 3, 4, 5 or 6 times by R3 or substituted 1 or 2 times by =O,
Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S(O)$_2$—, —$(CH_2)_m$—$NR^{10}$—C(O)—O—$(CH_2)_n$—, —($C_2$-$C_3$)-alkylene-S(O)$_2$—NH—($R^{10}$)—, —($C_2$-$C_3$)-alkylene-N($R^{10}$)— or —($C_0$-$C_3$)-alkylene-C(O)—O—$(CH_2)_m$—,
  wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$, —OH or —($C_3$-$C_6$)-cycloalkylen, wherein cycloalkylen is unsubstituted or mono-, di- or trisubstituted independently of one another by halogen, —$NH_2$ or —OH;
$R^1$ is hydrogen, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—$R^{15}$, amonocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14,
  $R^{4'}$ and $R^{5'}$ are independent of one another are identical or different and are hydrogen or —($C_1$-$C_4$)-alkyl,
$R^2$ is a direct bond or —($C_1$-$C_4$)-alkylene, or
$R^1$ and $R^3$ together with the atoms to which they are bonded can form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or
$R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14,
  R14 is halogen, —OH, =O, —($C_1$-$C_8$)-alkyl, —($C_1$-$C_4$)-alkoxy, —$NO_2$, —C(O)—OH, —CN, —$NH_2$, —C(O)—O—($C_1$-$C_4$)-alkyl, —(CO-$C_8$)-alkyl-$SO_2$—($C_1$-$C_4$)-alkyl, —($C_0$-$C_8$)-alkyl-$SO_2$—($C_1$-$C_3$)-perfluoroalkyl, —($C_0$-$C_8$)-alkyl-$SO_2$—N($R^{18}$)—$R^{21}$, —C(O)—NH—($C_1$-$C_8$)-alkyl, —C(O)—N—[($C_1$-$C_8$)-alkyl]$_2$, —$NR^{18}$—C(O)—NH—($C_1$-$C_8$)-alkyl, —C(O)—$NH_2$, —S—$R^{18}$, or —$NR^{18}$—C(O)—NH—[($C_1$-$C_8$)-alkyl]$_2$,
  wherein $R^{18}$ and $R^{21}$ are independently from each other hydrogen, —($C_1$-$C_3$)-perfluoroalkyl or —($C_1$-$C_6$)-alkyl,
V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
  2) a 6- to 14-membered aryl, wherein aryl is unsubstituted or mono-, di- or trisubstituted independently of one another by R14, or
  3) a monocyclic or bicyclic 4- to 15-membered heterocyclyl, wherein said heterocyclyl is unsubstituted or mono-, di- or trisubstituted independently of one another by R14,
G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, $(CH_2)_m$—C(O)—$NR^{10}$—$(CH_2)_n$—, —$(CH_2)_m$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—

—(CH$_2$)$_n$—,
—(CH$_2$)$_m$—NR$^{10}$—SO$_2$—(CH$_2$)$_n$—, —(CH$_2$)$_m$—NR$^{10}$—, —(CH$_2$)$_m$—O—C(O)—NR$^{10}$—(CH$_2$)$_n$— or —(CH$_2$)$_m$—NR$^{10}$—C(O)—O—(CH$_2$)$_n$—, n and m are independently of one another identical or different and are the integers zero, 1,2,3,4, 5 or 6, M is 1) hydrogen,
  2) —(C$_1$-C$_8$)-alkyl, wherein alkyl is unsubstituted or mono-, di- or trisubstituted independently of one another by R14,
  3) —C(O)—N(R11)—R12,
  4) —(CH$_2$)$_m$—NR$^{10}$,
  5) a 6- to 14-membered aryl, wherein aryl is unsubstituted or mono-, di- or trisubstituted independently of one another by R14,
  6) a monocyclic or bicyclic 4- to 15-membered heterocyclyl, wherein heterocyclyl is unsubstituted or mono-, di- or trisubstituted independently of one another by R14,
  7) —(C$_3$-C$_8$)-cycloalkyl, wherein said cycloalkyl is unsubstituted or mono-, di- or trisubstituted independently of one another by R14, or
  8) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, wherein R14 is defined above, R3 is
  1) hydrogen,
  2) halogen,
  3) —(C$_1$-C$_4$)-alkyl, wherein alkyl is unsubstituted or mono-, di- or trisubstituted independently of one another by R13,
  4) —(C$_1$-C$_3$)-perfluoroalkyl,
  5) phenyl, wherein phenyl is unsubstituted or mono-, di- or trisubstituted independently of one another by R13,
  6) —(C$_0$-C$_4$)-alkylene-O—R19, wherein R$^{19}$ is
    a) hydrogen,
    b) —(C$_1$-C$_4$)-alkyl, wherein alkyl is unsubstituted or mono-, di- or trisubstituted independently of one another by R13,
    c) phenyl, wherein phenyl is unsubstituted or mono-, di- or trisubstituted independently of one another by R13,
    d) —CF$_3$, or
    e) —CHF$_2$,
  7) —NO$_2$,
  8) —CN,
  9) —SO$_s$—R$^{11}$, wherein s is 1 or 2,
  10) —SO$_t$—N(R$^{11}$)—R$^{12}$, wherein t is 1 or 2,
  11) —(C$_0$-C$_4$)-alkylene-C(O)—R$^{11}$,
  12) —(C$_0$-C$_4$)-alkylene-C(O)—O—R$^{11}$,
  13) —(C$_0$-C$_4$)-alkylene-C(O)—N(R$^{11}$)—R$^{12}$,
  14) —(C$_0$-C$_4$)-alkylene-N(R$^{11}$)—R$^{12}$,
  15) —NR$^{10}$—SO$_2$—R$^{10}$,
  16) —S—R$^{10}$,
  17) —(C$_0$-C$_2$)alkylene-C(O)—O—(C$_2$-C$_4$)-alkylene-O—C(O)—(C$_1$-C$_4$)-alkyl,
  18) —C(O)—O—C(R15, R16)—O—C(O)—R17,
  19) —(C$_0$-C$_2$)alkylene-C(O)—O—(C$_2$-C$_4$)-alkylene-O—C(O)—O—(C$_1$-C$_6$)-alkyl,
  20) —C(O)—O—C(R15, R16)—O—C(O)—O—R17,
  21) —(C$_0$-C$_4$)-alkylene-(C$_6$-C$_{14}$)-aryl, wherein aryl is mono-, di- or trisubstituted independently of one another by R13,
  22) —(C$_0$-C$_4$)-alkylene-(C$_4$-C$_{15}$)-heterocyclyl, wherein heterocyclyl is unsubstituted or mono-, di- or trisubstituted independently of one another by R13
  23) —(C$_0$-C$_4$)-alkylene-(C$_3$-C$_8$)-cycloalkyl, wherein cycloalkyl is unsubstituted or mono-, di- or trisubstituted independently of one another by R13,
  24) —(C$_0$-C$_4$)-alkylene-het, wherein het is unsubstituted or mono-, di- or trisubstituted independently of one another by R13,
  25) —(C$_0$-C$_4$)-alkylene-O—CH$_2$-(C$_1$-C$_3$)-perfluoroalkylene-CH$_2$—O—(C$_0$-C$_4$)-alkyl,
  26) —SO$_w$—N(R$^{11}$)—R$^{13}$, wherein w is 1 or 2,
  27) —(C$_0$-C$_4$)-alkylene-C(O)—N(R$^{11}$)—R$^{13}$,
  28) —(C$_0$-C$_4$)-alkylene-N(R$^{11}$)—R$^{13}$, or
  29) a residue from the following list

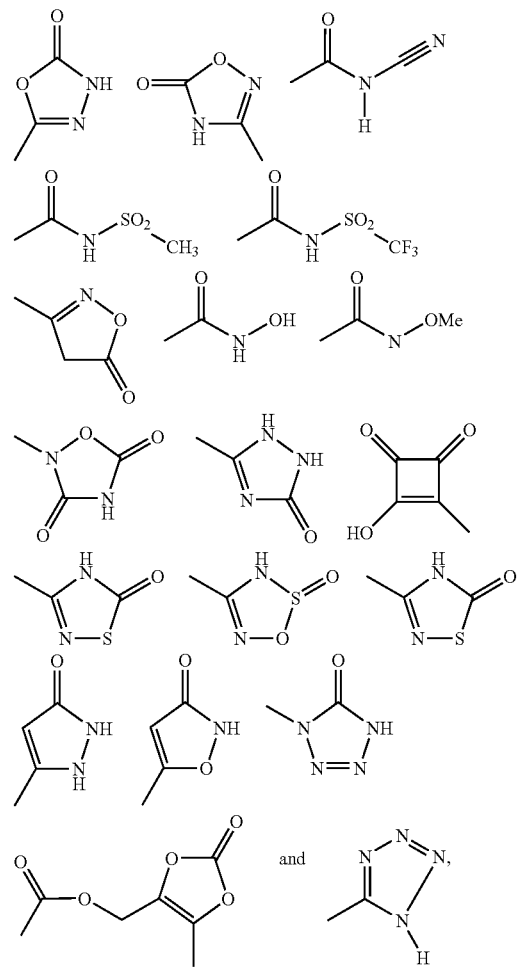

where Me is methyl, or if two —OR$^{19}$ residues are attached to adjacent atoms they can form together with the atoms which they are attached to a 5- or 6-membered ring, which is unsubstituted or substituted one, two, three or four times by R13, R11 and R12 are independently of one another identical or different and are
  1) hydrogen,
  2) —(C$_1$-C$_6$)-alkyl, wherein alkyl is unsubstituted or mono-, di- or trisubstituted independently of one another by R13,
  3) —(C$_0$-C$_6$)-alkyl-(C$_3$-C$_8$)-cycloalkyl, 4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or tri substituted by R13,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)—O—C(O)—R$^{17}$, —(C$_1$-C$_4$)-alkoxy-phenyl, —(C$_0$-C$_4$)-alkyl-C(O)—O—C(R15, R16)—O—C(O)—O—R$^{17}$, —(C$_1$-C$_3$)-perfluoroalkyl, —O—R15, —NH—C(O)—NH—R$^{10}$, —NH—C(O)—O—R$^{10}$, or a residue from the following list

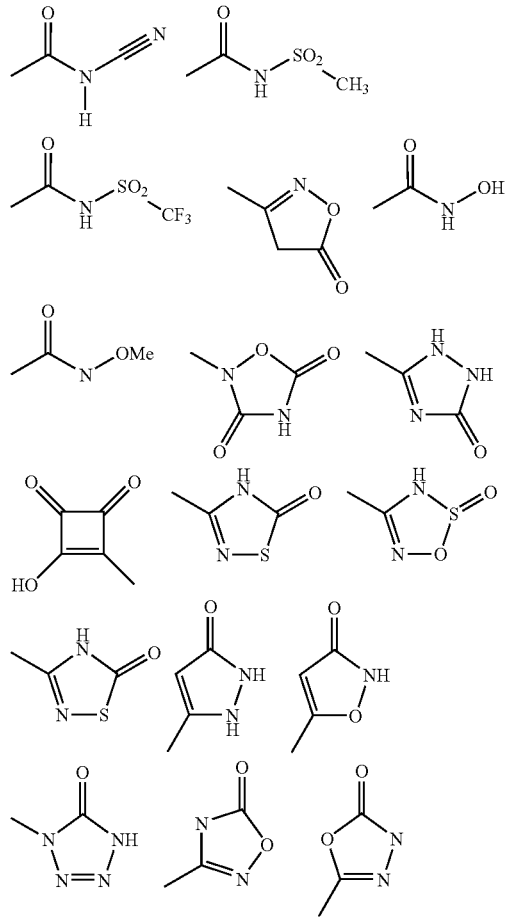

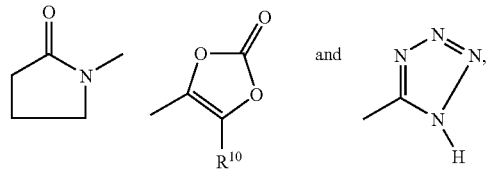

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl, R15 and R16 are independently of one another hydrogen, —(C$_1$-C$_6$)-alkyl, or together with the carbon atom to which they are bonded they can form a 3- to 6 membered carbocyclic ring which is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

DETAILED DESCRIPTION OF THE INVENTION

Definition of Terms

As used above, and throughout the description of the invention, the following terms, unless otherwise indicated, shall be understood to have the following meanings.

In general, the meaning of any group, residue, heteroatom, number etc., which can occur more than once in the compounds of the formula I, is independent of the meaning of this group, residue, heteroatom, number etc. in any other occurrence. All groups, residues, heteroatoms, numbers etc., which can occur more than once in the compounds of the formula I can be identical or different. As used herein, the term alkyl is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of "—(C$_1$-C$_8$)-alkyl" or "—(C$_1$-C$_8$)-alkylene" are alkyl residues containing 1, 2, 3, 4, 5, 6, 7 or 8 carbon atoms are methyl, methylene, ethyl, ethylene, propyl, propylene, butyl, butylene, pentyl, pentylene, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl. The term "—(C$_0$-C$_6$)-alkyl" or "—(C$_0$-C$_8$)-alkylene" is a hydrocarbon residues containing 1, 2, 3, 4, 5, 6, 7 or 8 carbon atoms. The term "—C$_0$-alkyl " or "—C$_0$-alkylene" is a covalent bond.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of —($C_3$-$C_8$)-cycloalkyl cyclic alkyl residues are cycloalkyl residues containing 3, 4, 5, 6, 7 or 8 ring carbon atoms like cyclopropyl, cyclobutyl, cyclopentyl, cyclohexyl, cyloheptyl or cyclooctyl, which can also be substituted and/or unsaturated. Unsaturated cyclic alkyl groups and unsaturated cycloalkyl groups like, for example, cyclopentenyl or cyclohexenyl can be bonded via any carbon atom.

The terms "a monocyclic or bicyclic 6- to 14-membered aryl" or "—($C_6$-$C_{14}$)-aryl" are understood as meaning aromatic hydrocarbon radicals containing from 6 to 14 carbon atoms in the ring. Examples of —($C_6$-$C_{14}$)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "mono- or bicyclic 4- to 15-membered heterocyclyl" or "—($C_4$-$C_{15}$)-heterocyclyl" refer to heterocycles in which one or more of the 4 to 15 ring carbon atoms are replaced by heteroatoms such as nitrogen, oxygen or sulfur.

Examples are acridinyl, azaindole (1H-pyrrolopyridinyl), 8-aza-bicyclo[3.2.1]oct-3-yl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, 1λ6-thiomorpholinyl, thiophenolyl, thiophenyl, thiopyranyl, 1,2,3-triazinyl, 1,2,4-triazinyl, 1,3, 5-triazinyl, 1,2,3-triazolyl, 1,2,3-triazolyl, 1,2,4-triazolyl, 1,2,5-triazolyl, 1,3,4-triazolyl and xanthenyl.

Preferred are heterocyclyls, such as benzimidazolyl, 1,3-benzodioxolyl, benzofuranyl, benzothiazolyl, benzothiophenyl, benzoxazolyl, chromanyl, cinnolinyl, 2-fuiryl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl and 3-thienyl.

Also preferred are:

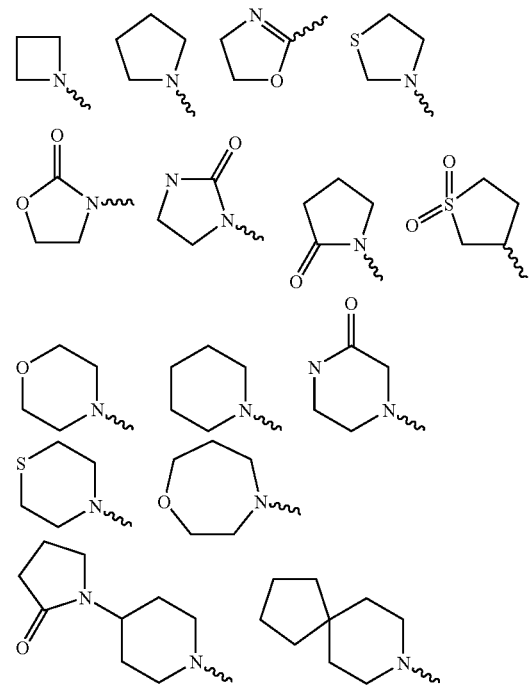

The terms "het" or "a 3- to 7-membered cyclic residue, containing up to 1, 2, 3 or 4 heteroatoms" refer to structures of heterocycles which can be derived from compounds such as azepine, azetidine, aziridine, azirine, 1,4 diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketomorpholine, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxetan, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydrofuran, tetrahydropyran, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole.

The term "$R^1$—N—$R^2$—V can form a 4- to 8-membered cyclic group " or "$R^1I^1$ and $R^{12}$ together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen" refer to structures of heterocycles which can be derived from compounds such as azepane, azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole.

The term "$R^{15}$ and $R^{16}$ together with the carbon atom to which they are bonded can form a 3- to 6 membered carbocyclic ring" refer to structures, which can be derived from compounds such as cyclopropyl, cyclobutyl, cyclopentyl or cyclohexyl.

The term "substructure

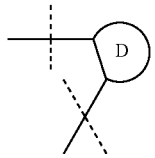

in formula I or the "substructure D" are a 4-to 8 membered saturated, partially unsaturated or aromatic cyclic group containing zero, 1, 2, 3 or 4 heteroatoms chosen from nitrogen, sulfur or oxygen" refer to structures, which can be derived from compounds such as azepane, azetidine, azetine, azocane, azocane-2-one, cyclobutyl, cyclooctane, cyclooctene, cyclopentyl, cyclohexyl, cycloheptyl, cyclooctyl, 1,2-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxaazepane, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, phenyl, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane-1-oxide, thiocan-2-one, thiomorpholine, thiopyran, 1,2,3-triazine, 1,2,4-triazine, 1,3,5-triazine, 1,2,3-triazole or 1,2,4-triazole.

The term "substructure D" is a 5 to 6 membered saturated, partially unsaturated or aromatic cyclic group containing zero, 1, 2, 3 or 4 heteroatoms chosen from nitrogen, sulfur or oxygen" refer to structures, which can be derived from compounds such as cyclopentyl, cyclohexyl, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, ketomorpholine, 1,2-oxathiolan, 1,2-oxazine, 1,3-oxazine, 1,4-oxazine, oxazole, piperazine, piperidine, phenyl, pyran, pyrazine, pyrazole, pyrazoline, pyrazolidine, pyrazine, pyrazinone, pyridazine, pyridazone, pyridine, pyridone, pyrimidine, pyrimidone, pyrrole, pyrrolidine, pyrrolidinone, pyrroline, tetrahydrofuran, tetrahydropyran, tetrahydropyridine, tetrahydrofuran, tetrazole, thiadiazine thiadiazole, 1,2-thiazine, 1,3-thiazine, 1,4-thiazine, 1,3-thiazole, thiazole, thiazolidine, thiazoline, thiomorpholine, thiopyran, tetrazine, tetrazole, 1,2,3-triazine, 1,2,4-triazine, 1,3,5-triazine, 1,2,3-triazole or 1,2,4-triazole.

The term "$R^1$ and $R^3$ together with the atoms to which they are bonded can form a 6- to 8-membered cyclic group, containing up to 1, 2, 3 or 4 heteroatoms chosen from nitrogen, sulfur or oxygen" refers to structures of heterocycles which can be derived from compounds such as azocane, azocane-2-one, cyloheptyl cyclohexyl, cyclooctane, cyclooctene, 1,4-diazepane, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxa-thiepane, 1,4-oxazepane, 1,2-oxazine, 1,3-oxazine, 1,4-oxazine, [1,4]oxazocane, [1,3]oxazocan-2-one, oxocane, oxocan-2-one, phenyl, piperazine, piperidine, pyran, pyrazine, pyridazine, pyrimidine, 5,6,7,8-tetrahydro-1H-azocin-2-one or thiomorpholine.

The fact that many of the before-listed names of heterocycles are the chemical names of unsaturated or aromatic ring systems does not imply that the, the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The term "—$(C_1$-$C_3)$-perfluoroalkyl" is a partial or totally fluorinated alkyl-residue, which can be derived from residues such as —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CH_2F$.

The term "—$(C_1$-$C_3)$-perfluoroalkylene" is a partial or totally fluorinated alkylene-residue, which can be derived from residues such as —$CF_2$—, —CHF—, —CHF—$CHF_2$—, —CHF—CHF—, —$CH_2$—$CF_2$—, —$CH_2$—CHF—, —$CF_2$—$CF_2$—, —$CF_2$—CHF—, —$CH_2$—CHF—$CF_2$—, —$CH_2$—CHF—CHF—, —$CH_2$—$CH_2$—$CF_2$—, —$CH_2$—$CH_2$—CHF, —$CH_2$—$CF_2$—$CF_2$—, —$CH_2$—$CF_2$—CHF—, —CHF—CHF—$CF_2$—, —CHF—CHF—CHF—, —CHF—$CH_2$—$CF_2$—, —CHF—$CH_2$—CHF—, —CHF—$CF_2$—$CF_2$—, —CHF—$CF_2$—CHF—, —$CF_2$—CHF—$CF_2$—, —$CF_2$—CHF—CHF—, —$CF_2$—$CH_2$—$CF_2$—, —$CF_2$—$CH_2$—CHF—, —$CF_2$—$CF_2$—$CF_2$—, or —$CF_2$—$CF_2$—CHF.

Halogen is fluorine, chlorine, bromine or iodine, preferably fluorine, chlorine or bromine, particularly preferably chlorine or bromine.

The term "oxo-residue" or "=O" refers to residues such as carbonyl (—C(O)—) or nitroso (—N=O).

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

Physiologically tolerable salts of the compounds of formula I are nontoxic salts that are physiologically acceptable, in particular pharmaceutically utilizable salts. Such salts of compounds of the formula I containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxy-ethyl)amine. Basic groups contained in the compounds of the formula I, for example amino groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. Compounds of the formula I, which simultaneously contain a basic group and an acidic group, for example a guanidino group and a carboxyl group, can also be present as zwitterions (betaines), which are likewise included in the present invention.

Patient includes both human and other mammals.

Pharmaceutically effective amount means an amount of the compound according to the invention effective in producing the desired therapeutic effect.

Particular or Preferred Embodiments

One particular embodiment of the present invention also relates to a compound of formula I, wherein one of $J_1$ and $J_2$ is N, and the other is N—Q—$R^0$, $R^0$ is 1) a monocyclic or bicyclic 6- to 14-membered aryl, wherein aryl is mono-, di- or trisubstituted independently of one another by R8, 2) a monocyclic or bicyclic 4- to 15-membered heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a monocyclic or bicyclic 4- to 15-membered heterocyclyl, containing one, two, three or four heteroatoms chosen from nitrogen, sulfur or oxygen, wherein said heterocyclyl is unsubstituted or mono-, di- or trisubstituted independently of one another by R8, and which is additionally substituted by a monocyclic or bicyclic 4- to 15-membered heterocyclyl, containing one, two, three or four heteroatoms chosen from nitrogen, sulfur or oxygen, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or a methoxy residue, or
10) —O—($C_1$-$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, provided that R8 is at least one halogen, —C(O)—$NH_2$ or —O—($C_1$-$C_8$)-alkyl residue, if $R^0$ is a monocyclic or bicyclic 6- to 14-membered aryl, substructure D is a 5- to 6 membered saturated, partially unsaturated or aromatic cyclic group containing zero, 1, 2, 3 or 4 heteroatoms chosen from nitrogen, sulfur or oxygen and is substituted 1, 2, 3, 4, 5 or 6 times by R3, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—NR—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —$(C_2-C_3)$-alkylene-O—$(C_0-C_3)$-alkylene-, —$(C_2-C_3)$-alkylene-S(O)—, —$(C_2-C_3)$-alkylene-S(O)$_2$—, —$(CH_2)_m$—$NR^{10}$—C(O)—O—$(CH_2)_n$—, —$(C_2-C_3)$-alkylene-S(O)$_2$—NH—$(R^{10})$—, —$(C_2-C_3)$-alkylene-N($R^{10}$)— or —$(C_0-C_3)$-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —$(C_3-C_6)$-cycloalkylen, wherein cycloalkylen is unsubstituted or mono-, di- or trisubstituted independently of one another by halogen, —$NH_2$ or —OH;

$R^1$ is hydrogen, —$(C_1-C_4)$-alkyl, wherein alkyl is unsubstituted or substituted one to three times by R13; —$(C_1-C_3)$-alkylene-C(O)—NH—$R^0$, —$(C_1-C_3)$-alkylene-C(O)—O—R15, a monocyclic or bicyclic 6- to 14-membered aryl, wherein aryl is mono-, di- or trisubstituted independently of one another by R8, wherein R8 is as defined above; a monocyclic or bicyclic 4- to 15-membered heterocyclyl, containing one, two, three or four heteroatoms chosen from nitrogen, sulfur or oxygen; —$(C_1-C_3)$-perfluoroalkylene,
—$(C_1-C_3)$-alkylene-S(O)—$(C_1-C_4)$-alkyl, —$(C_1-C_3)$-alkylene-S(O)$_2$—$(C_1-C_3)$-alkyl,
—$(C_1-C_3)$-alkylene-S(O)$_2$—N($R^{4'}$)—$R^{5'}$, —$(C_1-C_3)$-alkylene-O—$(C_1-C_4)$-alkyl,
—$(C_0-C_3)$-alkylene-$(C_3-C_8)$-cycloalkyl, or —$(C_0-C_3)$-alkylene-het, wherein het is unsubstituted or mono-, di- or trisubstituted independently of one another by R14, $R^{4'}$ and $R^{5'}$ are independent of one another are identical or different and are hydrogen or —$(C_1-C_4)$-alkyl, $R^2$ is a direct bond or —$(C_1-C_4)$-alkylene, or $R^1$ and R3 together with the atoms to which they are bonded can form a 6- to 8-membered cyclic group, containing up to 1, 2, 3 or 4 heteroatoms chosen from nitrogen, sulfur or oxygen, wherein said cyclic group is unsubstituted or mono-, di- or trisubstituted independently of one another by R14, or $R^1$—N—$R^2$—V can form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, R14 is halogen, —OH, =O, —$(C_1-C_8)$-alkyl, —$(C_1-C_4)$-alkoxy, —$NO_2$, —C(O)—OH, —CN, —$NH_2$,
—C(O)—O—$(C_1-C_4)$-alkyl, —$(C_0-C_8)$-alkyl-$SO_2$—$(C_1-C_4)$-alkyl,
—$(C_0-C_8)$-alkyl-$SO_2$—$(C_1-C_3)$-perfluoroalkyl, —$(C_0-C_8)$-alkyl-$SO_2$—N($R^{18}$)—$R^{21}$,
—C(O)—NH—$(C_1-C_8)$-alkyl, —C(O)—N—[$(C_1-C_8)$-alkyl]$_2$, —$NR^{18}$—C(O)—NH—$(C_1-C_8)$-alkyl,
—C(O)—$NH_2$, —S—$R^{18}$, or —$NR^{18}$—C(O)—NH—[$(C_1-C_8)$-alkyl]$_2$,
wherein $R^{18}$ and $R^{21}$ are independently from each other hydrogen, —$(C_1-C_3)$-perfluoroalkyl or Q$C_1-C_6)$-alkyl, V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14, 2) a 6- to 14-membered aryl, wherein aryl is unsubstituted or mono-, di- or trisubstituted independently of one another by R14, or 3) a monocyclic or bicyclic 4- to 15-membered heterocyclyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—, n and m are independently of one another identical or different and are the integers zero, 1, 2, 3, 4, 5 or 6, M is 1) hydrogen,
2) —$(C_1-C_8)$-alkyl, wherein alkyl is unsubstituted or mono-, di- or trisubstituted independently of one another by R14,
3) —C(O)—N($R^{11}$)—$R^{12}$,
4) —$(CH_2)_m$—$NR^{10}$,
5) —$(C_6-C_{14})$-aryl, wherein aryl is unsubstituted or mono-, di- or trisubstituted independently of one another by R14,
6) —$(C_4-C_{15})$-heterocyclyl, wherein heterocyclyl is unsubstituted or mono-, di- or trisubstituted independently of one another by R14,
7) —$(C_3-C_8)$-cycloalkyl, wherein said cycloalkyl is unsubstituted or mono-, di- or trisubstituted independently of one another by R14, or
8) a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14, wherein $R^{14}$ is defined above, R3 is
1) hydrogen,
2) halogen,
3) —$(C_1-C_4)$-alkyl, wherein alkyl is unsubstituted or mono-, di- or trisubstituted independently of one another by R13,
4) —$(C_1-C_3)$-perfluoroalkyl,
5) phenyl, wherein phenyl is unsubstituted or mono-, di- or trisubstituted independently of one another by R13,
6) —$(C_0-C_4)$-alkylene-O—$R^{19}$, wherein $R^{19}$ is
   a) hydrogen,
   b) —$(C_1-C_4)$-alkyl, wherein alkyl is unsubstituted or mono-, di- or trisubstituted independently of one another by R13,
   c) phenyl, wherein phenyl is unsubstituted or mono-, di- or trisubstituted independently of one another by R13,
   d) —$CF_3$,
   e) —$CHF_2$,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N($R^{11}$)—$R^{12}$,
14) —$(C_0-C_4)$-alkylene-N($R^{11}$)—$R^{12}$,
15) —$NR^{10}$—$SO_2$—$R^{10}$, 16) —S—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)—O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)—O—C(O)—O—R$^{17,}$
21) —(C$_0$-C$_4$)-alkylene-(C$_6$-C$_{14}$)-aryl, wherein aryl is mono-, di- or trisubstituted independently of one another by R13,
22) —(C$_0$-C$_4$)-alkylene-(C$_4$-C$_{15}$)-heterocyclyl, wherein heterocyclyl is unsubstituted or mono-, di- or trisubstituted independently of one another by R13
23) —(C$_0$-C$_4$)-alkylene-(C$_3$-C$_8$)-cycloalkyl, wherein cycloalkyl is unsubstituted or mono-, di- or trisubstituted independently of one another by R13,
24) —(C$_0$-C$_4$)-alkylene-het, wherein het is unsubstituted or mono-, di- or trisubstituted independently of one another by R13,
25) —(C$_0$-C$_3$)-alkylene-O—CH$_2$-(C$_1$-C$_3$)-perfluoroalkylene-CH$_2$—O—(C$_0$-C$_3$)-alkyl,
26) —SO$_w$—N(R$^{11}$)—R$^{13}$, wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue from the following list

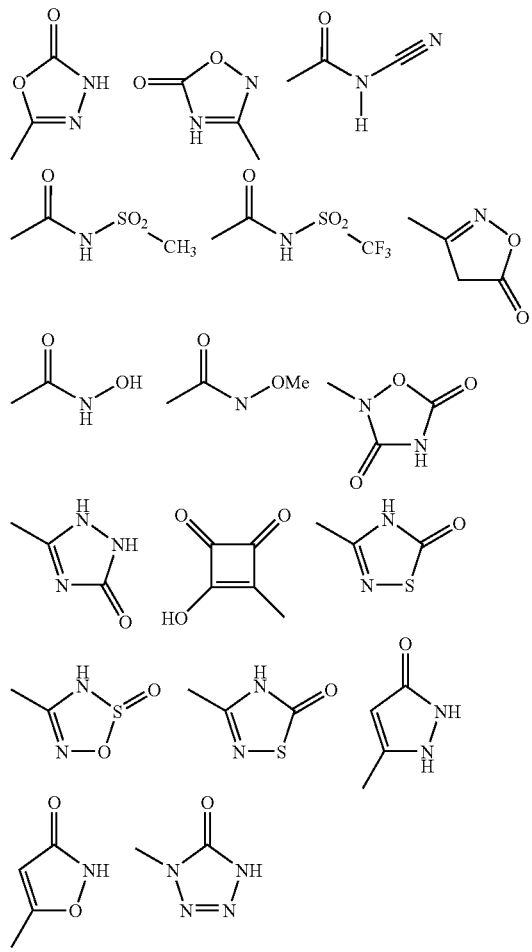

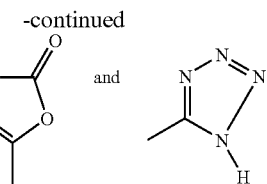

wherein Me is methyl, or if two —OR$^{19}$ residues are attached to adjacent atoms they can form together with the atoms which they are attached to a 5- or 6-membered ring, which is unsubstituted or substituted one, two, three or four times by R13, R11 and R12 are independently of one another identical or different and are
1) hydrogen,
2) —(C$_1$-C$_6$)-alkyl, wherein alkyl is unsubstituted or mono-, di- or trisubstituted independently of one another by R13,
3) —(C$_0$-C$_6$)-alkyl-(C$_3$-C$_8$)-cycloalkyl,
4) —SO$_t$—R$^{10}$, wherein t is 1 or 2,
5) —(C$_0$-C$_6$)-alkyl-(C$_6$-C$_{14}$)-aryl, wherein alkyl and aryl independently from one another are unsubstituted or mono-, di- or trisubstituted by R13,
6) —(C$_1$-C$_3$)-perfluoroalkyl,
7) —O—R$^{17}$, or
8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13, R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy-, —O—CF$_3$, —(C$_0$-C$_4$)-alkyl-C(O)—O—C(R15, R16)—O—C(O)—R17, —(C$_1$-C$_4$)-alkoxy-phenyl, —(C$_0$-C$_4$)-alkyl-C(O)—O—C(R15, R16)—O—C(O)—O—R$^{17}$, —(C$_1$-C$_3$)-perfluoroalkyl, —O—R15, —NH—C(O)—NH—R$^{10}$, —NH—C(O)—O—R$^{10}$, or a residue from the following list

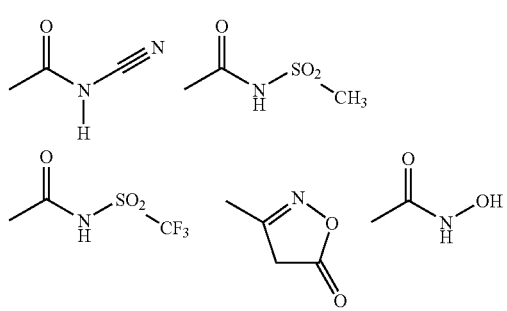

-continued

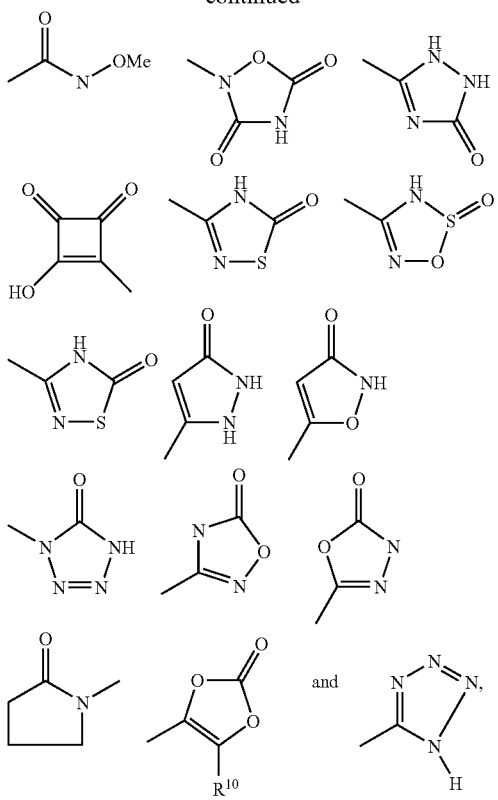

$R^{10}$ and $R^{20}$ are independently of one another hydrogen, —($C_1$-$C_6$)-alkyl or —($C_1$-$C_3$)-perfluoroalkyl, R15 and R16 are independently of one another hydrogen, —($C_1$-$C_6$)-alkyl, or together with the carbon atom to which they are bonded they can form a 3- to 6 membered carbocyclic ring which is unsubstituted or substituted one to three times by $R^{10}$, and R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts Another particular embodiment of the present invention relates to a compound of formula I, wherein one of $J_1$ and $J_2$ is N, and the other is N—Q—$R^0$, $R^0$ is 1) a monocyclic or bicyclic 6- to 14-membered aryl out of the group phenyl, naphthyl, biphenylyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,2,5,6-tetrahydro-pyridazinyl, wherein said heterocyclyl is unsubstituted or mono-, di- or trisubstituted independently of one another by R8, or 3) a heterocyclyl, wherein heterocyclyl is selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R8, and which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1) halogen,
2) —$NO_2$,
3) —CN,
4) —C(O)—$NH_2$,
5) —OH,
6) —$NH_2$,
7) —O—$CF_3$
8) a monocyclic or bicyclic 6- to 14-membered aryl, wherein aryl is as defined above and wherein aryl is mono-, di- or trisubstituted independently of one another by halogen or —O—($C_1$-$C_8$)-alkyl,
9) —($C_1$-$C_8$)-alkyl, wherein alkyl is unsubstituted or mono-, di- or trisubstituted independently of one another by halogen, $NH_2$, —OH or a methoxy residue, or
10) —O—($C_1$-$C_8$)-alkyl, wherein alkyl is unsubstituted or mono-, di- or trisubstituted independently of one another by halogen, $NH_2$, —OH or a methoxy residue,
11) —$SO_2$—$CH_3$ or
12) —$SO_2$—$CF_3$, provided that R8 is at least one halogen, —C(O)—$NH_2$ or —O—($C_1$-$C_8$)-alkyl residue, if $R^0$ is a monocyclic or bicyclic 6- to 14-membered aryl, wherein aryl is as defined above, substructure D is a residue selected out of the group azetidine, azetine, azocane, azocane-2-one, cyclobutyl, cyclooctane, cyclooctene, cyclopentyl, cyclohexyl, cycloheptyl, cyclooctyl, 1,4-diazepane, 1,2-diazepine, 1,3-diazepine, 1,4-diazepine, [1,4]diazocane, [1,2]diazocan-3-one, [1,3]diazocan-2-one, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolan, 1,2-oxazine, 1,3-oxazine, 1,4-oxazine, oxazole, [1,4]oxazocane, [1,3]oxazocan-2-one, oxetan, oxocane, oxocan-2-one, piperazine, piperidine, phenyl, pyran, pyrazine, pyrazole, pyrazoline, pyrazolidine, pyridazine, pyridine, pyrimidine, pyrrole, pyrrolidine, pyrrolidinone, pyrroline, 5,6,7,8-tetrahydro-1H-azocin-2-one, tetrahydrofuran, tetrahydropyran, tetrahydropyridine, tetrazine, thiadiazine, thiadiazole, 1,2-thiazine, 1,3-thiazine, 1,4-thiazine, 1,3-thiazole, thiazole, thiazolidine, thiazoline, thietan, thiocane, thiocane-1,1-dioxide, thiocane-1-oxide, thiocan-2-one, thiomorpholine, thiophene, thiopyran, 1,2,3-triazine, 1,2,4-triazine, 1,3,5-triazine, 1,2,3-triazole or 1,2,4-triazole and is unsubstituted or substituted 1, 2, 3, 4, 5 or 6 times by R3, Q is a direct bond, —($C_0$-$C_2$)-alkylene-C(O)—$NR^{10}$—, —$NR^{10}$—C(O)—$NR^{10}$—, —$NR^{10}$—C(O)—, —$SO_2$—, —($C_1$-$C_6$)-alkylene, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—S—$(CH_2)_n$—, —$(CH_2)_m$—C(O)—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—O—C(O)—$NR^{10}$—$(CH_2)_n$—, —($C_2$-$C_3$)-alkylene-O—($C_0$-$C_3$)-alkylene-, —($C_2$-$C_3$)-alkylene-S(O)—, —($C_2$-$C_3$)-alkylene-S$(O)_2$—, —$(CH_2)_m$—$NR^{10}$—C(O)—O—$(CH_2)_n$—, —($C_2$-$C_3$)-alkylene-S$(O)_2$—NH—($R^{10}$)—, —($C_2$-$C_3$)-alkylene-N($R^{10}$)— or —($C_0$-$C_3$)-alkylene-C(O)—O—$(CH_2)_m$—, wherein $R^{10}$ is as defined below, and wherein n and m are independently of one another identical or different and are the integers zero, 1, 2, 3, 4, 5 or 6, wherein the alkylene residues which are formed by —$(CH_2)_m$— or —$(CH_2)_n$— are unsubstituted or mono-, di- or trisubstituted independently of one another by halogen, —$NH_2$ or —OH; or —($C_3$-$C_6$)-cycloalkylen, wherein cycloalkylen is unsubstituted or mono-, di- or trisubstituted independently of one another by-halogen, —$NH_2$ or —OH;

$R^1$ is hydrogen, —($C_1$-$C_4$)-alkyl, wherein alkyl is unsubstituted or substituted one to three times by R13; —($C_1$-$C_3$)-alkylene-C(O)—NH—$R^0$, —($C_1$-$C_3$)-alkylene-C(O)—O—R15, an aryl out of the group phenyl, naphthyl, biphenylyl, anthryl or fluorenyl, wherein aryl is mono-, di- or trisubstituted independently of one another by R8, wherein R8 is as defined above;

a monocyclic or bicyclic 4- to 15-membered heterocyclyl, which is as defined above;
—($C_1$-$C_3$)-perfluoroalkylene, —($C_1$-$C_3$)-alkylene-S(O)—($C_1$-$C_4$)-alkyl,
—($C_1$-$C_3$)-alkylene-S$(O)_2$-($C_1$-$C_3$)-alkyl, —($C_1$-$C_3$)-alkylene-S$(O)_2$—N($R^{4'}$)—$R^{5'}$,
—($C_1$-$C_3$)-alkylene-O—($C_1$-$C_4$)-alkyl, —($C_0$-$C_3$)-alkylene-($C_3$-$C_8$)-cycloalkyl, or
—($C_0$-$C_3$)-alkylene-het, wherein het is a residue selected out of the group azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazirie, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, $R^{4'}$ and $R^{5'}$ are independent of one another are identical or different and are hydrogen or —($C_1$-$C_4$)-alkyl, $R^2$ is a direct bond or —($C_1$-$C_4$)-alkylene, or $R^1$ and R3 together with the atoms to which they are bonded can form a 6- to 8-membered cyclic residue selected out of the group azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, wherein said cyclic group is unsubstituted or mono-, di- or trisubstituted independently of one another by R14, or $R^1$—N—$R^2$—V can form a 4- to 8-membered cyclic group selected out of the group azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —$(C_1-C_8)$-alkyl, —$(C_1-C_4)$-alkoxy, —$NO_2$, —C(O)—OH, —CN, —$NH_2$, —C(O)—O—$(C_1-C_4)$-alkyl, —$(C_0-C_8)$-alkyl-$SO_2$—$(C_1-C_4)$-alkyl, —$(C_0-C_8)$-alkyl-$SO_2$—$(C_1-C_3)$-perfluoroalkyl, —$(C_0-C_8)$-alkyl-$SO_2$—$N(R^{18})$—$R^{21}$, —C(O)—NH—$(C_1-C_8)$-alkyl, —C(O)—N—$[(C_1-C_8)$-alkyl$]_2$, —$NR^{18}$—C(O)—NH—$(C_1-C_8)$-alkyl, —C(O)—$NH_2$, —S—$R^{18}$, or —$NR^{18}$—C(O)—NH—$[(C_1-C_8)$-alkyl$]_2$, wherein $R^{18}$ and $R^{21}$ are independently from each other hydrogen, —$(C_1-C_3)$-perfluoroalkyl or —$(C_1-C_6)$-alkyl, V is 1) a monocyclic or bicyclic 6- to 14-membered aryl out of the group phenyl, naphthyl, biphenylyl, anthryl or fluorenyl, wherein aryl is mono-, di- or trisubstituted independently of one another by R14, 2) a heterocyclyl out of the group acridinyl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein said heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_m$ or —$(CH_2)_m$—$NR^{10}$—C(O)—O—$(CH_2)_n$—, n and m are independently of one another identical or different and are the integers zero, 1, 2, 3, 4, 5 or 6, M is 1) hydrogen,
2) —$(C_1-C_8)$-alkyl, wherein alkyl is unsubstituted or mono-, di- or trisubstituted independently of one another by R14,
3) —C(O)—$N(R^{11})$—$R^{12}$,
4) —$(CH_2)_m$—$NR^{10}$,
5) —$(C_6-C_{14})$-aryl, wherein aryl is as defined above and wherein aryl is unsubstituted or mono-, di- or trisubstituted independently of one another by R14,
6) —$(C_4-C_{15})$-heterocyclyl, wherein heterocyclyl is as defined above and is unsubstituted or mono-, di- or trisubstituted independently of one another by R14, or
7) —$(C_3-C_8)$-cycloalkyl, wherein said cycloalkyl is unsubstituted or mono-, di- or trisubstituted independently of one another by R14, R3 is 1) hydrogen,
2) halogen,
3) —$(C_1-C_4)$-alkyl, wherein alkyl is unsubstituted or mono-, di- or trisubstituted independently of one another by R13,
4) —$(C_1-C_3)$-perfluoroalkyl,
5) phenyl, wherein phenyl is unsubstituted or mono-, di- or trisubstituted independently of one another by R13,
6) —$(C_0-C_4)$-alkylene-O—$R^{19}$, wherein R19 is
   a) hydrogen,
   b) —$(C_1-C_4)$-alkyl, wherein alkyl is unsubstituted or mono-, di- or tri substituted independently of one another by R13,
   c) phenyl, wherein phenyl is unsubstituted or mono-, di- or trisubstituted independently of one another by R13,
   d) —$CF_3$,
   e) —$CHF_2$,
7) —$NO_2$,
8) —CN,
9) —$SO_s$—$R^{11}$, wherein s is 1 or 2,
10) —$SO_t$—$N(R^{11})$—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$, 13) —($C_0$-$C_4$)-alkylene-C(O)—N($R^{11}$)—$R^{12}$,
14) —($C_0$-$C_4$)-alkylene-N($R^{11}$)—$R^{12}$,
15) —$NR^{10}$—$SO_2$—$R^{10}$,
16) —S—$R^{10}$,
17) —($C_0$-$C_2$)alkylene-C(O)—O—($C_2$-$C_4$)-alkylene-O—C(O)—($C_1$-$C_4$)-alkyl,
18) —C(O)—O—C(R15, R16)—O—C(O)—R17,
19) —($C_0$-$C_2$)alkylene-C(O)—O—($C_2$-$C_4$)-alkylene-O—C(O)—O—($C_1$-$C_6$)-alkyl,
20) —C(O)—O—C(R15, R16)—O—C(O)—O—R17,
21) —($C_0$-$C_4$)-alkylene-($C_6$-$C_{14}$)-aryl, wherein aryl is mono-, di- or trisubstituted independently of one another by R13,
22) —($C_0$-$C_4$)-alkylene-($C_4$-$C_{15}$)-heterocyclyl, wherein heterocyclyl is unsubstituted or mono-, di- or trisubstituted independently of one another by R13
23) —($C_0$-$C_4$)-aikylene-($C_3$-$C_8$)-cycloalkyl, wherein cycloalkyl is unsubstituted or mono-, di- or trisubstituted independently of one another by R13,
24) —($C_0$-$C_4$)-alylene-het, wherein het is unsubstituted or mono-, di- or trisubstituted independently of one another by R13,
25) —($C_0$-$C_3$)-alkylene-O—$CH_2$—($C_1$-$C_3$)-perfluoroalkylene-$CH_2$—O—($C_0$-$C_3$)-alkyl,
26) —$SO_w$—N($R^{11}$)—$R^{13}$, wherein w is 1 or 2,
27) —($C_0$-$C_4$)-alkylene-C(O)—N($R^{11}$)—$R^{13}$,
28) —($C_0$-$C_4$)-alkylene-N($R^{11}$)—$R^{13}$, or
29) a residue from the following list

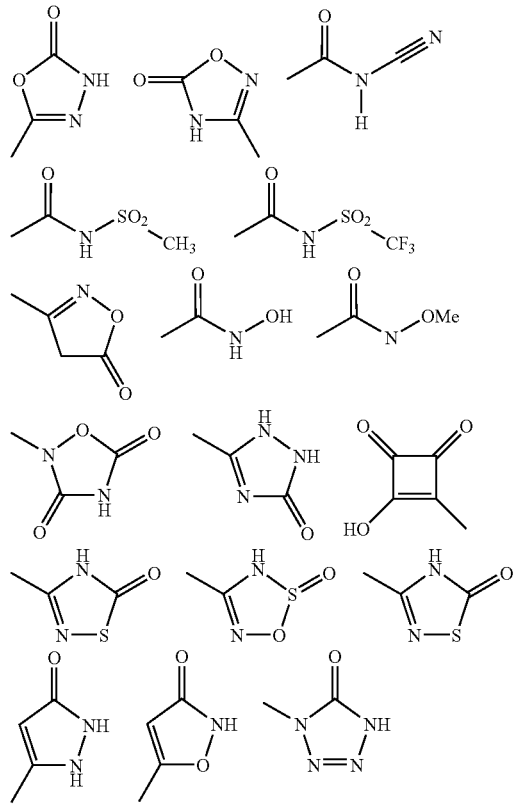

where Me is methyl, or if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are 1) hydrogen,
2) —($C_0$-$C_6$)-alkyl, wher ein alkyl is unsubstituted or mono-, di- or trisubstituted independently of one another by R13,
3) —($C_0$-$C_6$)-alkyl-($C_3$-$C_8$)-cycloalkyl,
4) —$SO_t$—$R^{10}$, wherein t is 1 or 2,
5) —($C_0$-$C_6$)-alkyl-($C_6$-$C_{14}$)-aryl, wherein alkyl and aryl independently from one another are unsubstituted or mono-, di- or tri substituted by R13,
6) —($C_1$-$C_3$)-perfluoroalkyl,
7) —O—$R^{17}$, or
8) —($C_0$-$C_6$)-alkyl-($C_4$-$C_{15}$)-heterocyclyl, wherein alkyl and heterocyclyl are as defined above and are independently from one another unsubstituted or mono-, di- or trisubstituted by R13, or R11 and R12 together with the nitrogen atom to which they are bonded form a heterocyclic ring out of the group azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said heterocyclic ring is unsubstituted or mono-, di- or trisubstituted independently of one another by R13, R13 is halogen, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_3$-$C_8$)-cycloalkyl, —($C_0$-$C_3$)-alkylene-O—$R^{10}$, —Si—$(CH_3)_3$, —N($R^{10}$)—S(O)$_u$—$R^{10}$, wherein u is 1 or 2, —S—$R^{10}$, —$SO_r$—$R^{10}$, wherein r is 1 or 2, —S(O)$_v$—N($R^{10}$)—$R^{20}$, wherein v is 1 or 2, —C(O)—$R^{10}$, —($C_1$-$C_8$)-alkyl, —($C_1$-$C_8$)-alkoxy, phenyl, phenyloxy-, —O—$CF_3$, —($C_0$-$C_4$)-alkyl-C(O)—O—C(R15, R16)—O—C(O)—$R^{17}$, —($C_1$-$C_4$)-alkoxy-phenyl, —($C_0$-$C_4$)-alkyl-C(O)—O—C(R15, R16)—O—C(O)—O—R17, —($C_1$-$C_3$)-perfluoroalkyl, —O—R15, —NH—C(O)—NH—$R^{10}$, —NH—C(O)—O—$R^{10}$, or a residue from the following list

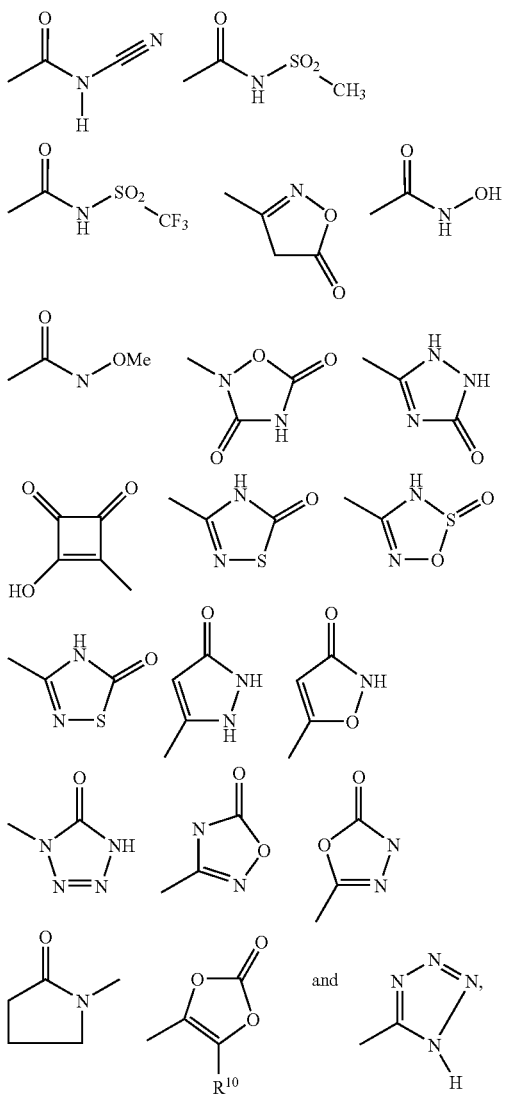

$R^{10}$ and $R^{20}$ are independently of one another hydrogen, —$(C_1$-$C_6)$-alkyl, —$(C_0$-$C_4)$-alkyl-OH, —$(C_0$-$C_4)$-alkyl-O—$(C_1$-$C_4)$-alkyl or —$(C_1$-$C_3)$-perfluoroalkyl, R15 and R16 are independently of one another hydrogen, —$(C_1$-$C_6)$-alkyl, cyclopropyl, cyclobutyl, cyclopentyl or cyclohexyl, wherein each ring is unsubstituted or substituted one to three times by $R^{10}$, and R17 is —$(C_1$-$C_6)$-alkyl, —$(C_1$-$C_6)$-alkyl-OH, —$(C_1$-$C_6)$-alkyl-O—$(C_1$-$C_6)$-alkyl, —$(C_3$-$C_8)$-cycloalkyl, —$(C_1$-$C_6)$-alkyl-O—$(C_1$-$C_8)$-alkyl-$(C_3$-$C_8)$-cycloalkyl, —$(C_1$-$C_6)$-alkyl-$(C_3$-$C_8)$-cycloalkyl, wherein said cycloalkyl ring is unsubstituted or substituted one, two or three times by —OH, —O—$(C_1$-$C_4)$-alkyl or $R^{10}$, in all its stereoisomeric forms and mixtures thereof in any ratio, and its physiologically tolerable salts Another particular embodiment of the present invention relates to a compound of formula I, wherein one of $J_1$ and $J_2$ is N, and the other is N—Q—$R^0$, $R^0$ is 1) a monocyclic or bicyclic 6- to 14-membered aryl out of the group phenyl, naphthyl, biphenyl, anthryl or fluorenyl, wherein aryl is mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl out of the group azabenzimidazolyl, benzimidazolyl, 1,3-benzodioxolyl, benzofuranyl, benzothiazolyl, benzothiophenyl, benzoxazolyl, chromanyl, cinnolinyl, 2-furyl, 3-furyl; imidazolyl, indolyl, indazolyl, isochromanyl, isoindolyl, isoquinolinyl, isothiazolyl, isoxazolyl, oxazolyl, phthalazinyl, pteridinyl, purinyl, pyrazinyl, pyrazolyl, pyridazinyl, pyridoimidazolyl, pyridopyridinyl, pyridopyrimidinyl, 2-pyridyl, 3-pyridyl, 4-pyridyl, pyrimidinyl, pyrrolyl; 2-pyrrolyl, 3-pyrrolyl, quinolinyl, quinazolinyl, quinoxalinyl, tetrazolyl, thiazolyl, 2-thienyl or 3-thienyl, which is additionally substituted by a heterocyclyl selected out of the group acridinyl, azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl, wherein heterocyclyl is unsubstituted or mono-, di- or trisubstituted independently of one another by R8, R8 is 1. F, Cl or Br,
2. —$NO_2$,
3. —CN,
4. —C(O)—$NH_2$, 5. —OH,
6. —NH$_2$,
7. —OCF$_3$
8. a monocyclic or bicyclic 6- to 14-membered aryl, wherein aryl is as defined above and is mono-, di- or trisubstituted independently of one another by halogen or —O—(C$_1$-C$_8$)-alkyl,
9. —(C$_1$-C$_8$)-alkyl, wherein alkyl is unsubstituted or mono-, di- or trisubstituted independently of one another by halogen, NH$_2$, —OH or a methoxy residue, or
10. —O—(C$_1$-C$_8$)-alkyl, wherein alkyl is unsubstituted or mono-, di- or trisubstituted independently of one another by halogen, NH$_2$, —OH or a methoxy residue,
11. —SO$_2$CH$_3$ or
12. —SO$_2$CF$_3$, provided that R8 is at least one halogen, —C(O)—NH$_2$ or —O—(C$_1$-C$_8$)-alkyl residue, if R0 is a aryl or a heterocyclyl, which are as defined above, substructure D is a residue selected out of the group phenyl, pyridyl, pyridyl-N-oxide pyridyl, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3, Q is a direct bond, —(C$_0$-C$_2$)-alkylene-C(O)—NR$^{10}$—, —NR$^{10}$—C(O)—NR$^{10}$—, —NR$^{10}$—C(O)—, —SO$_2$—, —(C$_1$-C$_6$)-alkylene or —(C$_0$-C$_3$)-alkylene-C(O)—O—(C$_0$-C$_2$)-alkylene, R$^1$ is hydrogen, —(C$_1$-C$_4$)-alkyl, wherein alkyl is unsubstituted or substituted one to three times by R13; —(C$_1$-C$_3$)-alkylene-C(O)—NH—R$^0$, —(C$_1$-C$_3$)-alkylene-C(O)—O—R15, —(C$_1$-C$_3$)-perfluoroalkylene, —(C$_1$-C$_3$)-alkylene-S(O)—(C$_1$-C$_4$)-alkyl, —(C$_1$-C$_3$)-alkylene-S(O)$_2$-(C$_1$-C$_3$)-alkyl, —(C$_1$-C$_3$)-alkylene-S(O)$_2$—N(R$^{4'}$)—R$^{5'}$, —(C$_1$-C$_3$)-alkylene-O—(C$_1$-C$_4$)-alkyl, —(C$_0$-C$_3$)-alkylene-(C$_3$-C$_8$)-cycloalkyl, or —(C$_0$-C$_3$)-alkylene-het, wherein het is a residue selected out of the group azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, wherein het is unsubstituted or mono-, di- or trisubstituted independently of one another by R14, R$^{4'}$ and R$^{5'}$ are independent of one another are identical or different and are hydrogen or —(C$_1$-C$_4$)-alkyl, R$^2$ is a direct bond or -C$_1$-C$_4$)-alkylene, or R$^1$—N—R$^2$—V form a 4- to 8-membered cyclic group selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, wherein said cyclic group is unsubstituted or mono-, di- or trisubstituted independently of one another by R14, R14 is fluorine, chlorine, bromine, iodine, —OH, =O, —(C$_1$-C$_8$)-alkyl, —(C$_1$-C$_4$)-alkoxy, —NO$_2$, —C(O)—OH, —CN, —NH$_2$, —C(O)—O—(C$_1$-C$_4$)-alkyl, —(C$_0$-C$_8$)-alkyl-SO$_2$—(C$_1$-C$_4$)-alkyl, —(C$_0$-C$_8$)-alkyl-SO$_2$-(C$_1$-C$_3$)-perfluoroalkyl, —(C$_0$-C$_8$)-alkyl-SO$_2$—N(R$^{18}$)—R$^{21}$, —C(O)—NH—(C$_1$-C$_8$)-alkyl, —C(O)—N—[(C$_1$-C$_8$)-alkyl]$_2$, —NR$^{18}$—C(O)—NH—(C$_1$-C$_8$)-alkyl, —C(O)—NH$_2$, —S—R$^{18}$, or —NR$^{18}$—C(O)—NH—[(C$_1$-C$_8$)-alkyl]$_2$, wherein R$^{18}$ and R$^{21}$ are independently from each other hydrogen, —(C$_1$-C$_3$)-perfluoroalkyl or —(C$_1$-C$_6$)-alkyl, V is 1) a het residue out of the group azaindole (1H-pyrrolopyridine), azepine, azetidine, aziridine, azirine, 1,4-diazepane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, which is as defined above and wherein het is unsubstituted or mono-, di- or trisubstituted independently of one another by R14, or 2) phenyl, wherein phenyl is unsubstituted or mono-, di- or trisubstituted independently of one another by R14, G is a direct bond, —(CH$_2$)$_m$—NR$^{10}$—SO$_2$—NR$^{10}$—(CH$_2$)$_n$—, —(CH$_2$)$_m$—CH(OH)—(CH$_2$)$_n$—, —(CH$_2$)$_m$—O—(CH$_2$)$_n$—, —(CH$_2$)$_m$—C(O)—NR$^{10}$—(CH$_2$)$_n$—, —(CH$_2$)$_m$—SO$_2$—(CH$_2$)$_n$—, —(CH$_2$)$_m$—NR$^{10}$—C(O)—NR$^{10}$—(CH$_2$)$_n$—, —(CH$_2$)$_m$—NR$^{10}$—C(O)—(CH$_2$)$_n$—, —(CH$_2$)$_m$—C(O)—(CH$_2$)$_n$—, —(CH$_2$)—S—(CH$_2$)$_n$—, —(CH$_2$)$_m$—SO$_2$—NR$^{10}$—(CH$_2$)$_n$—, —(CH$_2$)$_m$—NR$^{10}$—SO$_2$—(CH$_2$)$_n$—, —(CH$_2$)$_m$—NR$^{10}$—, —(CH$_2$)$_m$—O—C(O)—NR$^{10}$—(CH$_2$)$_n$— or —(CH$_2$)$_m$—NR$^{10}$—C(O)—O—(CH$_2$)$_n$—, n and m are independently of one another identical or different and are the integers zero, 1, 2, 3, 4, 5 or 6, M is 1) hydrogen,
2) —(C$_1$-C$_8$)-alkyl, wherein alkyl is unsubstituted or mono-, di- or trisubstituted independently of one another by R14,
3) —C(O)—N(R11)—R$^{12}$,
4) —(CH$_2$)$_m$—NR$^{10}$,
5) phenyl or naphthyl, wherein phenyl or naphthyl are unsubstituted or mono-, di- or trisubstituted independently of one another by R14,
6) heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiophene, thiomorpholine, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, or 7) —($C_3$-$C_8$)-cycloalkyl, wherein said cycloalkyl is unsubstituted or mono-, di- or trisubstituted independently of one another by R14, R3 is 1) hydrogen,
2) halogen,
3) —($C_1$-$C_4$)-alkyl, wherein alkyl is unsubstituted or mono-, di- or trisubstituted independently of one another by R13,
4) —($C_1$-$C_3$)-perfluoroalkyl,
5) phenyl, wherein phenyl is unsubstituted or mono-, di- or trisubstituted independently of one another by R13,
6) —($C_0$-$C_4$)-alkylene-O—R19, wherein R19 is
  a) hydrogen,
  b) —($C_1$-$C_4$)-alkyl, wherein alkyl is unsubstituted or mono-, di- or trisubstituted independently of one another by R13,
  c) phenyl, wherein phenyl is unsubstituted or mono-, di- or trisubstituted independently of one another by R13,
  d) —$CF_3$, or
  e) $CHF_2$,
7) —CN,
8) —($C_0$-$C_4$)-aikylene-($C_4$-$C_{15}$)-heterocyclyl, wherein heterocyclyl is as defined above and is unsubstituted or mono-, di- or trisubstituted independently of one another by R13,
9) —$SO_s$—$R^{11}$, wherein s is 1 or 2,
10) —$SO_t$—$N(R^{11})$—$R^{12}$, wherein t is 1 or 2,
11) —($C_0$-$C_4$)-alkylene-C(O)—$R^{11}$,
12) —($C_0$-$C_4$)-alkylene-C(O)—O—$R^{11}$,
13) —($C_0$-$C_4$)-alkylene-C(O)—$N(R^{11})$—R12,
14) —($C_0$-$C_4$)-alkylene-$N(R^{11})$—$R^{12}$,
15) —$NR^{10}$—$SO_2$—$R^{10}$,
16) —($C_0$-$C_4$)-alkylene-het, wherein het is as defined above and is unsubstituted or mono-, di- or trisubstituted independently of one another by R13,
17) —($C_0$-$C_2$)alkylene-C(O)—O—($C_2$-$C_4$)-alkylene-O—C(O)—($C_1$-$C_4$)-alkyl,
18) —C(O)—O—C(R15, R16)—O—C(O)—R17,
19) —($C_0$-$C_2$)alkylene-C(O)—O—($C_2$-$C_4$)-alkylene-O—C(O)—O—($C_1$-$C_6$)-alkyl,
20) —C(O)—O—C(R15, R16)—O—C(O)—O—R17,
21) —($C_0$-$C_4$)-alkylene-($C_6$-$C_{14}$)-aryl, wherein aryl is as defined above and is mono-, di- or trisubstituted independently of one another by R13,
22) —($C_0$-$C_4$)-alkylene-($C_3$-$C_8$)-cycloalkyl, wherein cycloalkyl is unsubstituted or mono-, di- or trisubstituted independently of one another by R13,
23) —($C_0$-$C_3$)-alkylene-O—$CH_2$—$CF_2$—$CH_2$—O—($C_0$-$C_3$)-alkyl,
24) —($C_0$-$C_3$)-alkylene-O—$CH_2$—$CF_2$—$CF_2$—$CH_2$—O—($C_0$-$C_3$)-alkyl,
25) —($C_0$-$C_3$)-aikylene-O—$CH_2$—($C_1$-$C_3$)-perfluoroalkylene-$CH_2$—OH,
26) —$SO_w$—$N(R^{11})$—$R^{13}$, wherein w is 1 or 2,
27) —($C_0$-$C_4$)-alkylene-C(O)—$N(R^{11})$—$R^{13}$,
28) —($C_0$-$C_4$)-alkylene-$N(R^{11})$—$R^{13}$, or
29) a residue from the following list

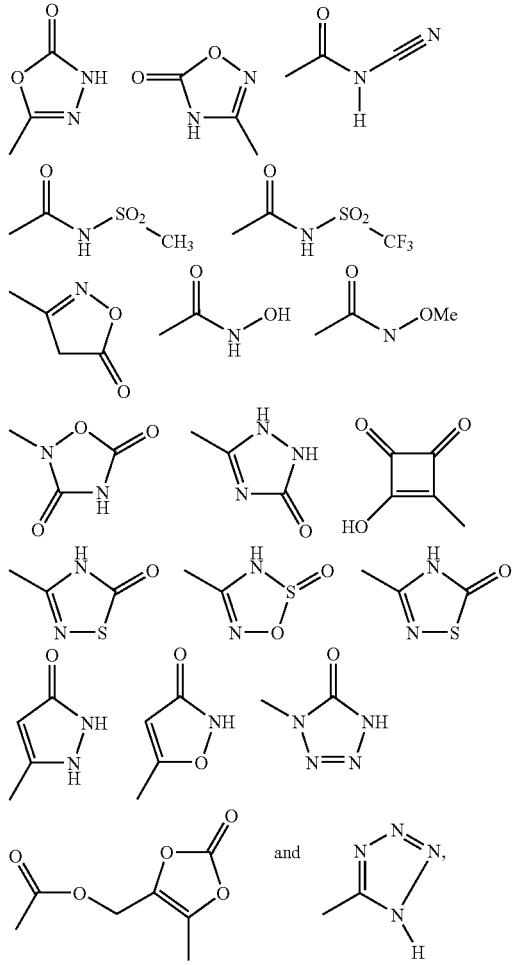

where Me is methyl, if two —OR19 residues are attached to adjacent atoms they can form together with the atoms which they are attached to a 1,3-dioxole ring or a 2,3-dihydro-[1,4]dioxine ring, which is substituted one, two, three or four times by R13, R11 and R12 are independently of one another identical or different and are
1) hydrogen,
2) —($C_1$-$C_6$)-alkyl, wherein alkyl is unsubstituted or mono-, di- or trisubstituted independently of one another by R13,
3) —($C_0$-$C_6$)-alkyl-($C_6$-$C_{14}$)-aryl, wherein aryl is as defined above and wherein alkyl and aryl are independently from one another unsubstituted or mono-, di- or trisubstituted by R13,
4) —O—$R^{17}$, or
5) —($C_0$-$C_6$)-alkyl-($C_4$-$C_{15}$)-heterocyclyl, wherein alkyl and heterocyclyl is as defined above and independently from one another are unsubstituted or mono-, di- or trisubstituted by R13, or $R^{11}$ and R12 together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrroline, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, which is unsubstituted or mono-, di- or trisubstituted independently of one another by R13, R13 is fluorine, chlorine, bromine, iodine, $-NO_2$, $-CN$, $=O$, $-OH$, $-CF_3$, $-C(O)-O-R^{10}$, $-C(O)-N(R^{10})-R^{20}$, $-N(R^{10})-R^{20}$, $-(C_0-C_3)$-alkylene-O—$R^{10}$, $-Si-(CH_3)_3$, $-N(R^{10})-S(O)_2-R^{10}$, $-S-R^{10}$, $-SO_2-R^{10}$, $-S(O)_2-N(R^{10})-R^{20}$, $-C(O)-R^{10}$, $-(C_1-C_8)$-alkyl, $-(C_1-C_8)$-alkoxy, phenyl, phenyloxy-, $-O-CF_3$, $-(C_1-C_3)$-perfluoroalkyl, $-(C_0-C_4)$-alkyl-C(O)—O—C(R15, R16)—O—C(O)—$R^{17}$, $-(C_1-C_4)$-alkoxy-phenyl, $-(C_0-C_4)$-alkyl-C(O)—O—C(R15, R16)—O—C(O)—O—$R^{17}$, $-O-R^{15}$, $-NH-C(O)-NH-R^{10}$, $-NH-C(O)-O-R^{10}$, or a residue from the following list

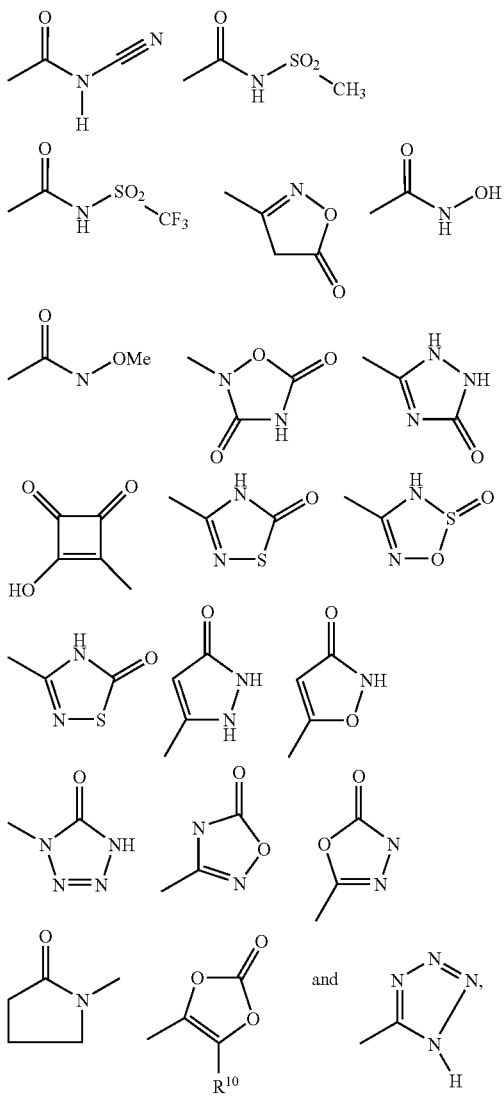

$R^{10}$ and $R^{20}$ are independently of one another hydrogen, $-(C_1-C_6)$-alkyl, $-(C_0-C_4)$-alkyl-OH, $-(C_0-C_4)$-alkyl-O—$(C_1-C_4)$-alkyl or $-(C_1-C_3)$-perfluoroalkl, R15 and R16 are independently of one another hydrogen, $-(C_1-C_6)$-alkyl, or together form a ring out of the group cyclopropyl, cyclobutyl, cyclopentyl or cyclohexyl, wherein each ring is unsubstituted or substituted one to three times by $R^{10}$, and R17 is $-(C_1-C_6)$-alkyl, $-(C_1-C_6)$-alkyl-OH, $-(C_1-C_6)$-alkyl-O—$(C_1-C_6)$-alkyl, $-(C_3-C_8)$-cycloalkyl, $-(C_1-C_6)$-alkyl-O—$(C_1-C_8)$-alkyl-$(C_3-C_8)$-cycloalkyl, $-(C_1-C_6)$-alkyl-$(C_3-C_8)$-cycloalkyl, wherein said cycloalkyl ring is unsubstituted or substituted one, two or three times by $-OH$, $-O-(C_1-C_4)$-alkyl or $R^{10}$, in all its stereoisomeric forms and mixtures thereof in any ratio, and its physiologically tolerable salts.

Another particular embodiment of the present invention relates to a compounds of formula I, wherein one of $J_1$ and $J_2$ is N, and the other is N—Q—$R^0$, R0 is 1) phenyl, wherein phenyl is unsubstituted or mono-, di- or trisubstituted independently of one another by R8, 2) a heterocyclyl out of the group benzimidazolyl, 1,3-benzodioxolyl, benzofuranyl, benzoxazolyl, benzothiazolyl, benzothiophenyl, cinnolinyl, chromanyl, indazolyl, indolyl, isochromanyl, isoindolyl, isoquinolinyl, phenylpyridyl, phthalazinyl, pteridinyl, purinyl, pyridyl, pyridoimidazolyl, pyridopyridinyl, pyridopyrimidinyl, pyrimidinyl, quinazolinyl, quinolyl, quinoxalinyl or 1,4,5,6-tetrahydro-pyridazinyl, wherein said heterocyclyl is unsubstituted or mono-, di- or trisubstituted independently of one another by R8, or 3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. F, Cl, Br or J,
2. $-C(O)-NH_2$,
3. $-(C_1-C_4)$-alkyl, wherein alkyl is unsubstituted or mono-, di- or trisubstituted independently of one another by halogen, $-OH$ or a methoxy residue, or
4. $-O-(C_1-C_4)$-alkyl, wherein alkyl is unsubstituted or mono-, di- or trisubstituted independently of one another by halogen or a methoxy residue, provided that R8 is at least one halogen, $-C(O)-NH_2$ or $-O-(C_1-C_8)$-alkyl residue, if R0 is a aryl or a heterocyclyl, which are as defined above, substructure D is a residue selected out of the group phenyl, pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R3, Q is a direct bond, —C(O)—; —SO$_2$— or —(C$_1$-C$_6$)-alkylene, —(C$_0$-C$_2$)-alkylene-C(O)—NR$^{10}$— or —(C$_0$-C$_3$)-alkylene-C(O)—O—(C$_0$-C$_2$)-alkylene, R$^1$ is hydrogen, —(C$_1$-C$_2$)-alkyl, —(C$_1$-C$_3$)-alkylene-C(O)—NH—R0, —(C$_1$-C$_3$)-perfluoroalkylene, —(C$_1$-C$_3$)-alkylene-C(O)—O—R$^{15}$, —(C$_1$-C$_3$)-alkylene-S(O)$_2$—(C$_1$-C$_3$)-alkyl or —(C$_1$-C$_3$)-alkylene-S(O)$_2$—N(R$^{4'}$)—R$^{5'}$, wherein R$^{4'}$ and R$^{5'}$ are independent of one another are identical or different and are hydrogen or —(C$_1$-C$_4$)-alkyl, R$^2$ is a direct bond or —(C$_1$-C$_2$)-alkylene, R$^1$—N—R$^2$—V can form a 4- to 7-membered cyclic group out of the group azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluorine, chlorine, —OH, =O, —(C$_1$-C$_8$)-alkyl, —C(O)—OH, —CN, —NH$_2$, —C(O)—O—(C$_1$-C$_4$)-alkyl, —C(O)—NH—(C$_1$-C$_8$)-alkyl, —C(O)—N—[(C$_1$-C$_8$)-alkyl]$_2$, —C(O)—NH$_2$ or —N(R$^{18}$)—R$^{21}$, wherein R$^{18}$ and R$^{21}$ are independently from each other hydrogen, —(C$_1$-C$_3$)-perfluoroalkyl or —(C$_1$-C$_4$)-alkyl, V is 1. a cyclic residue out of the group containing compounds which are derived from azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazine, 1,3-thiazine, 1,4-thiazine, thiadiazine or thiomorpholine, wherein said cyclic residue is unsubstituted or mono-, di- or trisubstituted independently of one another by R14, or 2. phenyl, wherein phenyl is unsubstituted or mono-, di- or trisubstituted independently of one another by R14, or G is a direct bond, —(CH$_2$)$_m$—, or —(CH$_2$)$_m$—NR$^{10}$—, m is the integers zero, 1, 2, 3 or 4, M is 1. hydrogen, 2. heterocyclyl, wherein heterocyclyl is a residue out of the group which can be derived from azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole or 1,2,4-triazole, wherein said heterocyclyl is unsubstituted or mono-, di- or trisubstituted independently of one another by R14, 3. —(C$_1$-C$_6$)-alkyl, wherein alkyl is unsubstituted or mono-, di- or trisubstituted independently of one another by R14, or 4. (C$_3$-C$_6$)-cycloalkyl,

5. —C(O)—N(R$^{11}$)—R$^{12}$,

R3 is 1) hydrogen, 2) halogen,

3) —(C$_1$-C$_4$)-alkyl, wherein alkyl is unsubstituted or mono-, di- or trisubstituted independently of one another by R13, 4) —(C$_1$-C$_3$)-perfluoroalkyl, 5) phenyl, wherein phenyl is unsubstituted or mono-, di- or trisubstituted independently of one another by R13, 6) —(C$_0$-C$_4$)-alkylene-O—R19, wherein R19 is a) hydrogen, b) —(C$_1$-C$_4$)-alkyl, wherein alkyl is unsubstituted or mono-, di- or trisubstituted independently of one another by R13, c) phenyl, wherein phenyl is unsubstituted or mono-, di- or trisubstituted independently of one another by R13, d) —CF$_3$, or e) CHF$_2$,

7) —CN,

8) —NR$^{10}$—SO$_2$—R$^{10}$,

9) —SO$_s$—R$^{11}$, wherein s is 1 or 2,

10) —SO$_t$—N(R$^{11}$)—R$^{12}$, wherein t is 1 or 2,

11) —(C$_0$-C$_4$)-alkylene-C(O)—R$^{11}$,

12) —(C$_0$-C$_4$)-alkylene-C(O)—O—R$^{11}$,

13) —(C$_0$-C$_4$)-alkylene-C(O)—N(R$^{11}$)—R$^{12}$,

14) —(C$_0$-C$_4$)-alkylene-N(R$^{11}$)—R$^{12}$,

15) —(C$_0$-C$_2$)alkylene-C(O)—O—(C$_2$-C$_4$)-alkylene-O—C(O)—(C$_1$-C$_4$)-alkyl,

16) —C(O)—O—C(R15, R16)—O—C(O)—R17,

17) —(C$_0$-C$_2$)alkylene-C(O)—O—(C$_2$-C$_4$)-alkylene-O—C(O)—O—(C$_1$-C$_6$)-alkyl,

18) —C(O)—O—C(R15, R16)—O—C(O)—O—R17,

20) —(C$_0$-C$_3$)-alkylene-O—CH$_2$—CF$_2$—CH$_2$—O—(C$_0$-C$_3$)-alkyl,

21) —(C$_0$-C$_3$)-alkylene-O—CH$_2$—CF$_2$—CF$_2$—CH$_2$—O—(C$_0$-C$_3$)-alkyl, 22) —(C$_0$-C$_3$)-alkylene-O—CH$_2$—(C$_1$-C$_3$)-perfluoroalkylene-CH$_2$—OH, 23) —SO$_w$—N(R$^{11}$)—R$^{13}$, wherein w is 1 or 2, 24) —(C$_0$-C$_4$)-alkylene-C(O)—N(R$^{11}$)—R$^{13}$, 25) —(C$_0$-C$_4$)-alkylene-N(R$^{11}$)—R$^{13}$, or 26) a residue from the following list

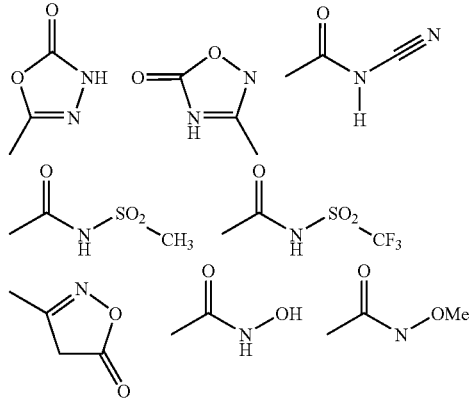

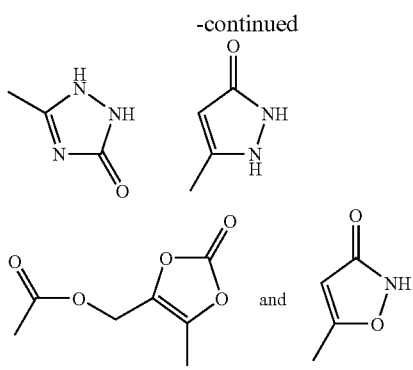

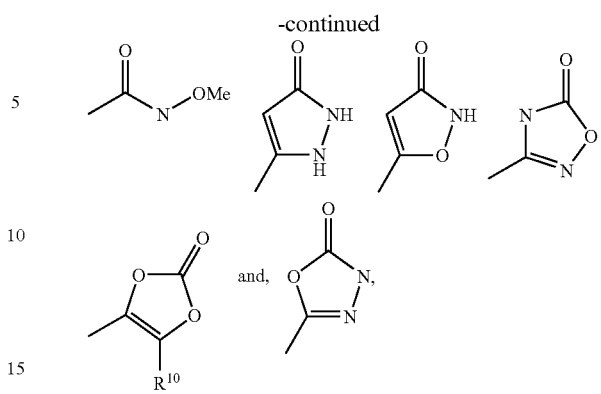

wherein Me is methyl, if two —OR19 residues are attached to adjacent atoms they can form together with the atoms which they are attached to a 1,3-dioxole ring or a 2,3-dihydro-[1,4]dioxine ring, which is substituted one, two, three or four times by R13, $R^{11}$ and $R^{12}$ together with the nitrogen atom to which they are bonded can form a ring selected out of the group azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, wherein said ring is unsubstituted or mono-, di- or trisubstituted independently of one another by R13, R13 is fluorine, chlorine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —NH—C(O)—NH—R$^{10}$, —(C$_0$-C$_4$)-alkyl-C(O)—O—C(R15, R16)—O—C(O)—R17, —(C$_1$-C$_4$)-alkoxy-phenyl, —(C$_0$-C$_4$)-alkyl-C(O)—O—C(R15, R16)—O—C(O)—O—R17, —O—R15, —NH—C(O)—O —R$^{10}$, or a residue from the following list

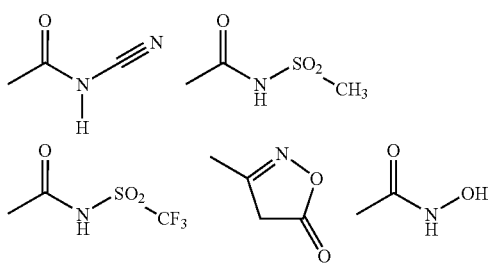

wherein Me is methyl, $R^{10}$ and $R^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl, R15 and R16 are independently of one another hydrogen, —(C$_1$-C$_6$)-alkyl, or together form a ring out of the group cyclopropyl, cyclobutyl, cyclopentyl or cyclohexyl, wherein each ring is unsubstituted or substituted one to three times by R$^{10}$, and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein said cycloalkyl ring is unsubstituted or substituted one, two or three times by —OH, —O—(C$_1$-C$_4$)-alkyl or R$^{10}$, in all its stereoisomeric forms and mixtures thereof in any ratio, and its physiologically tolerable salts.

Another particular embodiment of the present invention relates to a compound of formula I, wherein one of $J_1$ and $J_2$ is N, and the other is N—Q—R$^0$, R0 is 1) phenyl, wherein phenyl is unsubstituted or mono-, di- or trisubstituted independently of one another by R8, 2) a heterocyclyl selected out of the group indolyl, isoindolyl, benzofuranyl, benzothiophenyl, 1,3-benzodioxolyl, indazolyl, benzimidazolyl, benzoxazolyl, benzothiazolyl, quinolinyl, isoquinolinyl, chromanyl, isochromanyl, cinnolinyl, quinazolinyl, quinoxalinyl, phthalazinyl, pyridoimidazolyl, pyridopyridinyl, pyridopyrimidinyl, pyridyl, purinyl and pteridinyl, wherein said heterocyclyl is unsubstituted or mono-, di- or trisubstituted independently of one another by R8, 3) a heterocyclyl out of the group pyridyl, 2-pyridyl, 3-pyridyl, 4-pyridyl, pyrrolyl, 2-pyrrolyl, 3-pyrrolyl, furyl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said heterocyclyl is unsubstituted or mono-, di- or trisubstituted independently of one another by R8, and in addition is substituted by a residue selected out of the group pyridyl, 2-pyridyl, 3-pyridyl, 4-pyridyl, pyrrolyl, 2-pyrrolyl, 3-pyrrolyl, fuiryl, 2-furyl, 3-furyl; thienyl, 2-thienyl, 3-thienyl, imidazolyl, pyrazolyl, oxazolyl, isoxazolyl, thiazolyl, thiadiazolyl, isothiazolyl, triazolyl, tetrazolyl, pyridazinyl and pyrazinyl, wherein said residue is unsubstituted or mono-, di- or trisubstituted independently of one another by R8

R8 is 1. is F, Cl, Br, J,
2. —C(O)—NH$_2$,
3. —(C$_1$-C$_4$)-alkyl, wherein alkyl is unsubstituted or mono-, di- or trisubstituted independently of one another by halogen, —OH or a methoxy residue, or
4. —O—(C$_1$-C$_4$)-alkyl, wherein alkyl is unsubstituted or mono-, di- or trisubstituted independently of one another by halogen or a methoxy residue,
provided that R8 is at least one halogen, —C(O)—NH$_2$ or —O—(C$_1$-C$_8$)-alkyl residue, if R0 is a aryl or a heterocyclyl, which are as defined above, substructure D is a residue selected out of the group phenyl, pyridyl, pyridyl-N-oxide, pyrrolyl, furyl, thienyl, imidazolyl, pyrazolyl, oxazolyl, isoxazolyl, thiazolyl, triazolyl, isothiazolyl, thiadiazolyl, pyrimidinyl, pyridazinyl, pyrazinyl and is unsubstituted or substituted 1, 2, 3 or 4 times by R$^3$, Q is a direct bond, —C(O)—; —SO$_2$—, —C(O)—O-methylene, —(C$_1$-C$_6$)-alkylene or —(C$_0$-C$_2$)-alkylene-C(O)—NR$^{10}$—, R$^1$ is hydrogen or —(C$_1$-C$_2$)-alkyl, R$^2$ is a direct bond or —(C$_1$-C$_2$)-alkylene, or R$^1$—N—R$^2$-V can form a 4- to 7-membered cyclic group out of the group piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, wherein said cyclic group is unsubstituted or mono-, di- or trisubstituted independently of one another by R14, R14 is fluoro, chlorine, —(C$_1$-C$_4$)-alkyl or —NH$_2$, V is 1. a cyclic residue out of the group containing compounds, which are derived from azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazine, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole or 1,2,4-triazole,
wherein said cyclic residue is unsubstituted or mono-, di- or trisubstituted independently of one another by R14, or 2. phenyl, wherein phenyl is unsubstituted or mono-, di- or trisubstituted independently of one another by R14, G is a direct bond, —(CH$_2$)$_m$—, or —(CH$_2$)$_m$—NR$^{10}$—, m is the integers zero, 1, 2, 3 or 4, M is 1. hydrogen,
2. heterocyclyl, wherein heterocyclyl is a residue out of the group which can be derived from 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine,
wherein said heterocyclyl is unsubstituted or mono-, di- or trisubstituted independently of one another by R14,
3. —(C$_1$-C$_6$)-alkyl, wherein alkyl is unsubstituted or mono-, di- or trisubstituted independently of one another by R14, or
4. (C$_3$-C$_6$)-cycloalkyl, R3 is 1) hydrogen,
2) halogen,
3) —(C$_1$-C$_4$)-alkyl, wherein alkyl is unsubstituted or mono-, di- or trisubstituted independently of one another by R13,
4) —(C$_1$-C$_3$)-perfluoroalkyl,
5) phenyl, wherein phenyl is unsubstituted or mono-, di- or trisubstituted independently of one another by R13,
6) —(C$_0$-C$_4$)-alkylene-O—R19, wherein R19 is
   a) hydrogen,
   b) —(C$_1$-C$_4$)-alkyl, wherein alkyl is unsubstituted or mono-, di- or trisubstituted independently of one another by R13, or
   c) phenyl, wherein phenyl is unsubstituted or mono-, di- or trisubstituted independently of one another by R13,
   d) —CF$_3$, or
   e) —CHF$_2$,
7) —CN,
8) —NR$^{10}$—SO$_2$—R$^{10}$,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —(C$_0$-C$_2$)alkylene-C(O)—O—(C$_2$-C$_4$)-alkylene-O—C(O)—(C$_1$-C$_4$)-alkyl,
16) —C(O)—O—C(R15, R16)—O—C(O)—R17,
17) —(C$_0$-C$_2$)alkylene-C(O)—O—(C$_2$-C$_4$)-alkylene-O—C(O)—O—(C$_1$-C$_6$)-alkyl,
18) —C(O)—O—C(R15, R16)—O—C(O)—O—R17,
19) —(C$_0$-C$_3$)-alkylene-O—CH$_2$—CF$_2$—CH$_2$—O—(C$_0$-C$_3$)-alkyl,
20) —(C$_0$-C$_3$)-alkylene-O—CH$_2$—CF$_2$—CF$_2$—CH$_2$—O—(C$_0$-C$_3$)-alkyl,
21) —(C$_0$-C$_3$)-alkylene-O—CH$_2$—(C$_1$-C$_3$)-perfluoroalkylene-CH$_2$—OH,
22) —SO$_w$—N(R$^{11}$)—R$^{13}$, wherein w is 1 or 2,
23) —(C$_0$-C$_4$)-alkylene-C(O)—N(R$^{11}$)—R$^{13}$,
24) —(C$_0$-C$_4$)-alkylene-N(R$^{11}$)—R$^{13}$, or
25) a residue from the following list

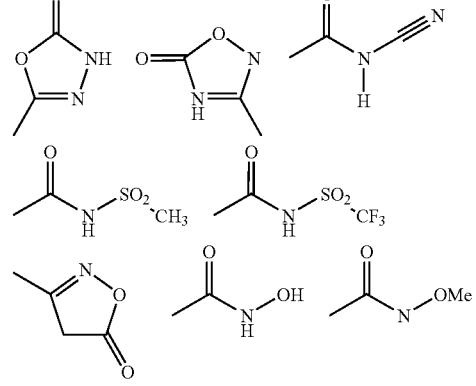

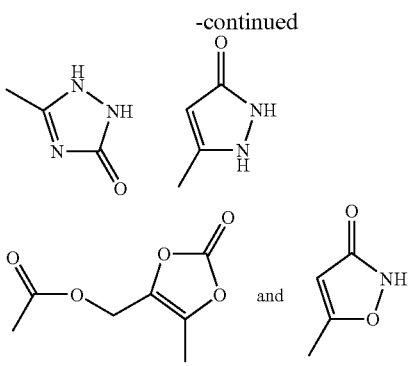

wherein Me is methyl,

R11 and R12 are independently of one another identical or different and are
1) hydrogen,
2) —($C_1$-$C_4$)-alkyl, wherein alkyl is unsubstituted or mono-, di- or trisubstituted independently of one another by R13,
3) —($C_0$-$C_6$)-alkyl-($C_3$-$C_6$)-cycloalkyl,
4) —O—$R^{17}$, or
5) —($C_0$-$C_6$)-alkyl-($C_4$-$C_{15}$)-heterocyclyl, wherein alkyl and heterocyclyl independently from one another are unsubstituted or mono-, di- or trisubstituted by R13 and wherein heterocyclyl is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or R11 and R12 together with the nitrogen atom to which they are bonded form a heterocyclic ring, which is selected out of the group azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, R13 is fluorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—$(CH_3)_3$, —S—$R^{10}$, —$SO_2$—$R^{10}$, —($C_1$-$C_3$)-perfluoroalkyl, or a residue from the following list

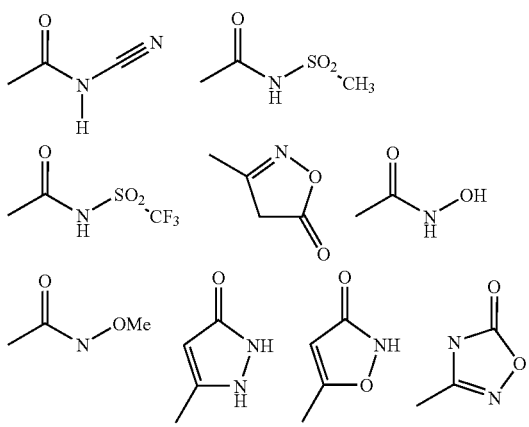

methyl, $R^{10}$ and $R^{20}$ are independently of one another hydrogen, —($C_1$-$C_4$)-alkyl or —($C_1$-$C_3$)-perfluoroalkyl, $R^{15}$ and $R^{16}$ are independently of one another hydrogen, —($C_1$-$C_4$)-alkyl, or together form a ring out of the group cyclopropyl, cyclobutyl, cyclopentyl or cyclohexyl, wherein each ring is unsubstituted or substituted one to three times by $R^{10}$, and R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl—($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or $R^{10}$, in all its stereoisomeric forms and mixtures thereof in any ratio, and its physiologically tolerable salts.

Another particular embodiment of the present invention relates to a compound of formula I, wherein
R0 is 1. phenyl, wherein phenyl is unsubstituted or mono- or disubstituted independently of one another by R8,
2. pyridyl, wherein pyridyl is unsubstituted or mono- or disubstituted independently of one another by R8, or
3. a heterocyclyl out of the group thienyl, thiadiazolyl, isoxazolyl and thiazolyl, wherein said heterocyclyl is substituted by a residue selected out of the group thienyl, 2-thienyl and 3-thienyl, wherein said residue is unsubstituted or mono- or disubstituted independently of one another by R8, R8 is F, Cl, Br, —$OCH_3$, —C(O)—$NH_2$ or —O—$CF_3$, substructure D is a residue selected out of the group phenyl, pyridyl, pyridyl-N-oxide, pyrrolyl, thienyl, imidazolyl, pyrazolyl, oxazolyl, isoxazolyl, thiazolyl, isothiazolyl, thiadiazolyl, pyrimidinyl, pyridazinyl or pyrazinyl and is unsubstituted or substituted 1, 2, 3 or 4 times by R3, Q is a direct bond, —C(O)—; —$SO_2$—, —C(O)—O-methylene, —$CH_2$—C(O)—NH—, methylene or ethylene, $R^1$ is hydrogen, $R^2$ is a direct bond or methylene, $R^1$—N—$R^2$—V can form a 4- to 8-membered cyclic group out of the group azetidine, pyrrolidine, piperidine and piperazine, R14 is fluorine, chlorine, methyl, ethyl, =O, —$SO_2$—$CH_3$ or —$NH_2$, V is 1. a residue out of the group containing compounds which is derived from azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, wherein said cyclic residue is unsubstituted or mono- or disubstituted independently of one another by R14, or
2. phenyl, wherein phenyl is unsubstituted or mono- or disubstituted independently of one another by R14, G is a direct bond, —$(CH_2)_m$—, —C(O)— or —$(CH_2)_m$—$NR^{10}$—, m is the integers zero, 1 or 2, M is hydrogen, $(C_2-C_4)$-alkyl, azepanyl, cyclopropyl, cyclobutyl, cyclopentyl, cyclohexyl, imidazolyl, ketomorpholinyl, morpholinyl, [1,4]Oxazepanyl, piperidinyl, piperidonyl, phenyl, pyrazinyl, pyrazolyl, pyridazinyl, pyridyl, pyrimidyl, pyrrolidinyl, 1,4,5,6-tetrahydro-pyridazinyl, or tetrahydropyranyl, wherein the residues are unsubstituted or mono- or disubstituted independently of one another by R14

R3 is 1) hydrogen,
  2) fluorine, chlorine,
  3) $-(C_1-C_4)$-alkyl, wherein alkyl is unsubstituted or mono-, di- or trisubstituted independently of one another by R13,
  4) $-(C_1-C_3)$-perfluoroalkyl,
  5) phenyl, wherein phenyl is unsubstituted or mono-, di- or trisubstituted independently of one another by R13,
  6) $-(C_0-C_2)$-alkylene-O—$R^{19}$, wherein R19 is
    a) hydrogen,
    b) $-(C_1-C_4)$-alkyl, wherein alkyl is unsubstituted or mono-, di- or trisubstituted independently of one another by R13,
    c) phenyl, wherein phenyl is unsubstituted or mono-, di- or trisubstituted independently of one another by R13,
    d) $-CF_3$, or
    e) $-CHF_2$,
  7) —CN,
  8) $-NR^{10}-SO_2-R^{10}$,
  9) $-SO_s-R^{11}$, wherein s is 1 or 2,
  10) $-SO_t-N(R^{11})-R^{12}$, wherein t is 1 or 2,
  11) $-(C_0-C_4)$-alkylene-C(O)—$R^{11}$,
  12) $-(C_0-C_4)$-alkylene-C(O)—O—$R^{11}$,
  13) $-(C_0-C_4)$-alkylene-C(O)—N($R^{11}$)—$R^{12}$,
  14) $-(C_0-C_4)$-alkylene-N($R^{11}$)—$R^{12}$,
  15) $-(C_0-C_2)$alkylene-C(O)—O—$(C_2-C_4)$-alkylene-O—C(O)—$(C_1-C_4)$-alkyl,
  16) —C(O)—O—C(R15, R16)—O—C(O)—R17,
  17) $-(C_0-C_2)$alkylene-C(O)—O—$(C_2-C_4)$-alkylene-O—C(O)—O—$(C_1-C_6)$-alkyl,
  18) —C(O)—O—C(R15, R16)—O—C(O)—O—R17,
  19) $-(C_0-C_4)$-alkylene-C(O)—N($R^{11}$)—$R^{13}$ or
  20) a residue from the following list

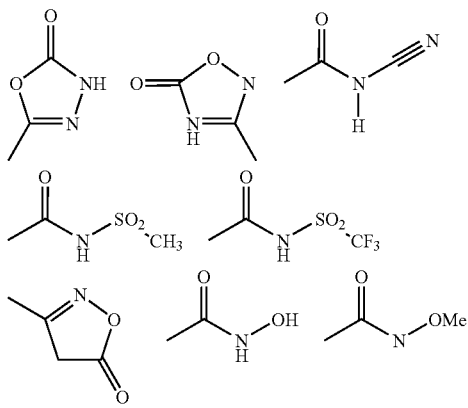

-continued

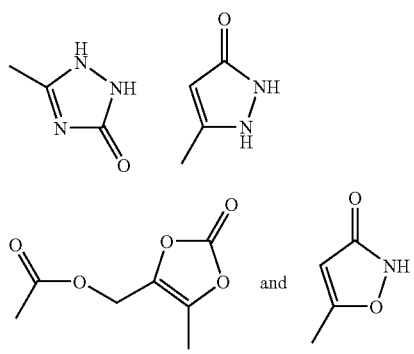

wherein Me is methyl,

R11 and R12 are independently of one another identical or different and are
  1) hydrogen,
  2) $-(C_1-C_4)$-alkyl, wherein alkyl is unsubstituted or mono-, di- or trisubstituted independently of one another by R13,
  3) $-(C_0-C_6)$-alkyl-$(C_3-C_6)$-cycloalkyl,
  4) $-O-R^{17}$, or
  5) $-(C_0-C_6)$-alkyl-heterocyclyl, wherein alkyl and heterocyclyl independently from one another are unsubstituted or mono-, di- or trisubstituted by R13 and wherein heterocyclyl is selected out of the group azetidine, imidazolidine, 4,5-dihydro-[1,2,4]oxadiazole, -[1,3]dioxole, (1,4)-oxazepane or pyrrolidine or R11 and R12 together with the nitrogen atom to which they are bonded can form a ring, which is selected out of the group azetidine, imidazolidine, morpholine, (1,4)-oxazepane piperazine, piperidine, pyrrolidine or thiomorpholine, R13 is fluorine, —CN, =O, —OH, $-CF_3$, —C(O)—O—$R^{10}$, —C(O)—N($R^{10}$)—$R^{20}$, —N($R^{10}$)—$R^{20}$, $-(C_1-C_3)$-alkyl, $-(C_3-C_6)$-cycloalkyl, $-(C_0-C_3)$-alkylene-O—$R^{10}$, $-Si-(CH_3)_3$, $-S-R^{10}$, $-SO_2-R^{10}$, $-SO_2-NH$, $-(C_1-C_3)$-perfluoroalkyl, or a residue from the following list

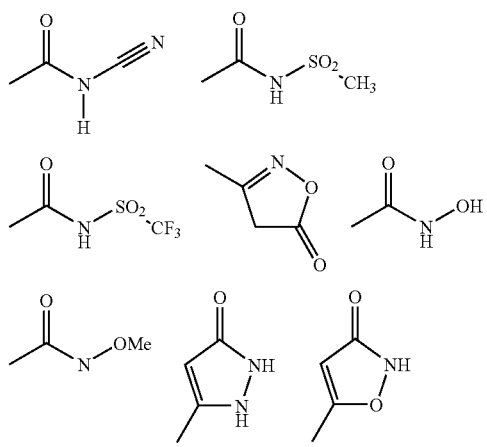

-continued

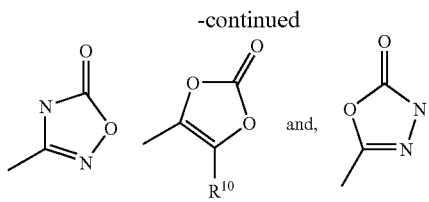

and, wherein Me is methyl,
R[10] and R[20] are independently of one another hydrogen, —($C_1$-$C_4$)-alkyl or —($C_1$-$C_3$)-perfluoroalkyl,
R[15] and R[16] are independently of one another hydrogen, —($C_1$-$C_4$)-alkyl, or together form a ring out of the group cyclopropyl, cyclobutyl, cyclopentyl or cyclohexyl, wherein each ring is unsubstituted or substituted one to three times by R[10], and
R17 is —($C_1$-$C_6$)-alkyl, —($C_1$-$C_6$)-alkyl-OH, —($C_1$-$C_6$)-alkyl-O—($C_1$-$C_6$)-alkyl, —($C_3$-$C_8$)-cycloalkyl, —($C_1$-$C_6$)-alkyl-O—($C_1$-$C_8$)-alkyl-($C_3$-$C_8$)-cycloalkyl, —($C_1$-$C_6$)-alkyl-($C_3$-$C_8$)-cycloalkyl, wherein said cycloalkyl ring is unsubstituted or substituted one, two or three times by —OH, —O—($C_1$-$C_4$)-alkyl or R[10], in all its stereoisomeric forms and mixtures thereof in any ratio, and its physiologically tolerable salts.

Another particular embodiment of the present invention relates to a compound of formula I, wherein $J_1$ is N, and $J_2$ is N—Q—R[0].

Another particular embodiment of the present invention relates to a compound of formula I, wherein $J_2$ is N, and $J_1$ is N—Q—R[0].

Another particular embodiment of the present invention relates to a compound of formula I, which is
1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester,
1-[5-(5-Chloro-thiophen-2-yl)-isoxazol-3-ylmethyl]-3-(1-isopropyl-piperidin-4-ylcarbamoyl)-1H-indazole-6-carboxylic acid methyl ester,
1-[5-(5-Chloro-thiophen-2-yl)-isoxazol-3-ylmethyl]-3-(1-isopropyl-piperidin-4-ylcarbamoyl)-1H-indazole-7-carboxylic acid methyl ester,
1-[5-(5-Chloro-thiophen-2-yl)-isoxazol-3-ylmethyl]-3-(1-isopropyl-piperidin-4-ylcarbamoyl)-1H-indazole-5-carboxylic acid,
1-[5-(5-Chloro-thiophen-2-yl)-isoxazol-3-ylmethyl]-3-(1-isopropyl-piperidin-4-ylcarbamoyl)-1H-indazole-7-carboxylic acid,
1-[5-(5-Chloro-thiophen-2-yl)-isoxazol-3-ylmethyl]-3-(1-isopropyl-piperidin-4-ylcarbamoyl)-1H-indazole-6-carboxylic acid,
Indazole-1,3-dicarboxylic acid 1-[(5-chloro-pyridin-2-yl)-amide]-3-[(1-isopropyl-piperidin-4-yl)-amide],
1-[5-(5-Chloro-thiophen-2-yl)-isoxazol-3-ylmethyl]-1H-indazole-3-carboxylic acid (1-isopropyl-piperidin-4-yl)-amide,
1-[5-(5-Chloro-thiophen-2-yl)-isoxazol-3-ylmethyl]-3-(1-isopropyl-piperidin-4-ylcarbamoyl)-1H-indazole-5-carboxylic acid 1-ethoxycarbonyloxy-ethyl ester,
1-[5-(5-Chloro-thiophen-2-yl)-isoxazol-3-ylmethyl]-4-cyano-1H-indazole-3-carboxylic acid (1-isopropyl-piperidin-4-yl)-amide,
1-[5-(5-Chloro-thiophen-2-yl)-isoxazol-3-ylmethyl]-4-(5-oxo-4,5-dihydro-[1,2,4]oxadiazol-3-yl)-1H-indazole-3-carboxylic acid (1-isopropyl-piperidin-4-yl)-amide,
5-(Azetidine-1-carbonyl)-1-[5-(5-chloro-thiophen-2-yl)-isoxazol-3-ylmethyl]-1H-indazole-3-carboxylic acid (1-isopropyl-piperidin-4-yl)-amide,
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-methanesulfonyl-ethyl)-amide],
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-sulfamoyl-ethyl)-amide],
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-morpholin-4-yl-ethyl)-amide],
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-trimethylsilanylmethyl-amide,
1-[5-(5-Chloro-thiophen-2-yl)-isoxazol-3-ylmethyl]-1H-indazole-3,5-dicarboxylic acid 5-[bis-(2-hydroxy-ethyl)-amide]3-[(1-isopropyl-piperidin-4-yl)-amide],
1-[5-(5-Chloro-thiophen-2-yl)-isoxazol-3-ylmethyl]-1H-indazole-3,5-dicarboxylic acid 5-[(2-hydroxy-ethyl)-methyl-amide]3-[(1-isopropyl-piperidin-4-yl)-amide],
{1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid ethyl ester,
1-[5-(5-Chloro-thiophen-2-yl)-isoxazol-3-ylmethyl]-1H-indazole-3,5-dicarboxylic acid 5-[(2,2-difluoro-ethyl)-amide]3-[(1-isopropyl-piperidin-4-yl)-amide],
1-[5-(5-Chloro-thiophen-2-yl)-isoxazol-3-ylmethyl]-1H-indazole-3,5-dicarboxylic acid 5-carbamoylmethyl-amide 3-[(1-isopropyl-piperidin-4-yl)-amide],
1-[5-(5-Chloro-thiophen-2-yl)-isoxazol-3-ylmethyl]-1H-indazole-3,5-dicarboxylic acid 5-[(2-hydroxy-ethyl)-amide]3-[(1-isopropyl-piperidin-4-yl)-amide],
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-{[2-(2-oxo-imidazolidin-1-yl)-ethyl]-amide},
1-[5-(5-Chloro-thiophen-2-yl)-isoxazol-3-ylmethyl]-1H-indazole-3,5-dicarboxylic acid 5-[(2-hydroxy-1-hydroxymethyl-1-methyl-ethyl)-amide]3-[(1-isopropyl-piperidin-4-yl)-amide],
{1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid,
1-[1-[5-(5-Chloro-thiophen-2-yl)-isoxazol-3-ylmethyl]-3-(1-isopropyl-piperidin-4-ylcarbamoyl)-1H-indazole-5-carbonyl]-(2S)-azetidine-2-carboxylic acid,
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2,2,2-trifluoro-ethyl)-amide],
{1-[5-(5-Chloro-thiophen-2-yl)-isoxazol-3-ylmethyl]-3-(1-isopropyl-piperidin-4-ylcarbamoyl)-1H-indazole-5-carbonyl]-methyl-amino}-acetic acid,
1-[5-(5-Chloro-thiophen-2-yl)-isoxazol-3-ylmethyl]-3-(1-isopropyl-piperidin-4-ylcarbamoyl)-1H-indazole-5-carboxylic acid 2-hydroxy-ethyl ester,
1-[5-(5-Chloro-thiophen-2-yl)-isoxazol-3-ylmethyl]-5-([1,4]oxazepane-4-carbonyl)-1H-indazole-3-carboxylic acid (1-isopropyl-piperidin-4-yl)-amide,
1-[5-(5-Chloro-thiophen-2-yl)-isoxazol-3-ylmethyl]-5-(3-hydroxy-azetidine-1-carbonyl)-1H-indazole-3-carboxylic acid (1-isopropyl-piperidin-4-yl)-amide,
1-[5-(5-Chloro-thiophen-2-yl)-isoxazol-3-ylmethyl]-1H-indazole-3,5-dicarboxylic acid 3-[(1-isopropyl-piperidin-4-yl)-amide]5-(methoxy-amide), 1-[(5-Chloro-pyridin-2-ylcarbamoyl)-methyl]-1H-indazole-3-carboxylic acid [4-(piperidine-1-carbonyl)-phenyl]-amide, 1-[5-(5-Chloro-thiophen-2-yl)-isoxazol-3-ylmethyl]-1H-indazole-3-carboxylic acid [4-(pyrrolidine-1-carbonyl)-phenyl]-amide, 1-[5-(5-Chloro-thiophen-2-yl)-isoxazol-3-ylmethyl]-1H-indazole-3-carboxylic acid [4-(morpholine-4-carbonyl)-phenyl]-amide, 1-[(5-Chloro-pyridin-2-ylcarbamoyl)-methyl]-1H-indazole-3-carboxylic acid [4-(morpholine-4-carbonyl)-phenyl]-amide, 1-(1-{1-[5-(5-Chloro-thiophen-2-yl)-isoxazol-3-ylmethyl]-1H-indazole-3-carbonyl}-piperidin-4-yl)-pyrrolidin-2-one, N-(5-Chloro-pyridin-2-yl)-2-{3-[4-(2-oxo-pyrrolidin-1-yl)-piperidine-1-carbonyl]-indazol-1-yl}-acetamide, 1-[5-(5-Chloro-thiophen-2-yl)-isoxazol-3-ylmethyl]-1H-indazole-3-carboxylic acid [4-(2-oxo-pyrrolidin-1-yl)-phenyl]-amide, 1-[(5-Chloro-pyridin-2-ylcarbamoyl)-methyl]-1H-indazole-3-carboxylic acid [4-(2-oxo-pyrrolidin-1-yl)-phenyl]-amide, 1-[5-(5-Chloro-thiophen-2-yl)-isoxazol-3-ylmethyl]-1H-indazole-3-carboxylic acid (2'-methanesulfonyl-biphenyl-4-yl)-amide, 1-[(5-Chloro-pyridin-2-ylcarbamoyl)-methyl]-1H-indazole-3-carboxylic acid (2'-methanesulfonyl-biphenyl-4-yl)-amide, 1-[5-(5-Chloro-thiophen-2-yl)-isoxazol-3-ylmethyl]-1H-indazole-3-carboxylic acid [4-(4-methyl-6-oxo-1,4,5,6-tetrahydro-pyridazin-3-yl)-phenyl]-amide, 1-[5-(5-Chloro-thiophen-2-yl)-isoxazol-3-ylmethyl]-1H-indazole-3-carboxylic acid (4-morpholin-4-yl-phenyl)-amide, 1-[5-(5-Chloro-thiophen-2-yl)-isoxazol-3-ylmethyl]-1H-indazole-3-carboxylic acid [4-(1H-imidazol-4-yl)-phenyl]-amide, 1-[5-(5-Chloro-thiophen-2-yl)-isoxazol-3-ylmethyl]-1H-indazole-3-carboxylic acid (4-piperidin-1-yl-phenyl)-amide, 1-[5-(5-Chloro-thiophen-2-yl)-isoxazol-3-ylmethyl]-3-[4-(3-oxo-morpholin-4-yl)-phenylcarbamoyl]-1H-indazole-5-carboxylic acid methyl ester, 1-[(5-Chloro-pyridin-2-ylcarbamoyl)-methyl]-3-(1-isopropyl-piperidin-4-ylcarbamoyl)-1H-indazole-5-carboxylic acid methyl ester, 1-[(5-Chloro-pyridin-2-ylcarbamoyl)-methyl]-3-(1-isopropyl-piperidin-4-ylcarbamoyl)-1H-indazole-5-carboxylic acid, 1-[5-(5-Chloro-thiophen-2-yl)-isoxazol-3-ylmethyl]-3-(1-isopropyl-piperidin-4-ylcarbamoyl)-1H-indazole-5-carboxylic acid 5-methyl-2-oxo-[1,3]dioxol-4-ylmethyl ester, 1-[5-(5-Chloro-thiophen-2-yl)-isoxazol-3-ylmethyl]-5-(cyanamide-1-carbonyl)-1H-indazole-3-carboxylic acid (1-isopropyl-piperidin-4-yl)-amide, 1-[1-[5-(5-Chloro-thiophen-2-yl)-isoxazol-3-ylmethyl]-3-(1-isopropyl-piperidin-4-ylcarbamoyl)-1H-indazole-5-carbonyl]-azetidine-3-carboxylic acid, 1-[(5-Chloro-pyridin-2-ylcarbamoyl)-methyl]-1H-indazole-3-carboxylic acid [4-(3-oxo-morpholin-4-yl)-phenyl]-amide, 1-[5-(5-Chloro-thiophen-2-yl)-isoxazol-3-ylmethyl]-1H-indazole-3-carboxylic acid [4-(4-oxo-4H-pyridin-1-yl)-phenyl]-amide, 1-[(5-Chloro-pyridin-2-ylcarbamoyl)-methyl]-1H-indazole-3-carboxylic acid [4-(4-oxo-4H-pyridin-1-yl)-phenyl]-amide, 1-[5-(5-Chloro-thiophen-2-yl)-isoxazol-3-ylmethyl]-3-(1-isopropyl-piperidin-4-ylcarbamoyl)-1H-indazole-5-carboxylic acid 2-methoxy-ethyl ester, 1-[(5-Chloro-pyridin-2-ylcarbamoyl)-methyl]-3-(1-isopropyl-piperidin-4-ylcarbamoyl)-1H-indazole-5-carboxylic acid 2-hydroxy-ethyl ester, or 1-[(5-Chloro-pyridin-2-ylcarbamoyl)-methyl]-5-([1,4]oxazepane-4-carbonyl)-1H-indazole-3-carboxylic acid (1-isopropyl-piperidin-4-yl)-amide.

Salts of compounds of the formula I can be obtained by customary methods known to those skilled in the art, for example by combining a compound of the formula I with an inorganic or organic acid or base in a solvent or dispersant, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The present invention furthermore includes all solvates of compounds of the formula I, for example hydrates or adducts with alcohols.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I, which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985; Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogens on nitrogen atoms in such groups are replaced with an acyl group or a carbamate, preferably a —($C_1$-$C_6$)-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, ($C_1$-$C_8$)-alkyl, ($C_3$-$C_8$)-cycloalkyl, ($C_3$-$C_8$)-cycloalkyl-($C_1$-$C_4$)-alkyl-, ($C_6$-$Cl_4$)-aryl, Het-, ($C_6$-$C_{14}$)-aryl-($C_1$-$C_4$)-alkyl- or Het-($C_1$-$C_4$)-alkyl- and in which $R^{p2}$ has the meanings indicated for $R^{p1}$ with the exception of hydrogen.

Especially preferred compounds of the formula I are those wherein two or more residues are defined as indicated before for preferred compounds of the formula I, or residues can have one or some of the specific denotations of the residues given in their general definitions or in the definitions of preferred compounds before. All possible combinations of definitions given for preferred definitions and of specific denotations of residues explicitly are a subject of the present invention.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I, all residues that are present more than one time in the molecule are independent of each other and can be identical or different.

The compounds of the formula I can be prepared by utilising procedures and techniques, which per se are well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in the literature, or by procedures or analogously to procedures described in this application.

In general, compounds of the formula I can be prepared, for example in the course of a convergent synthesis, by linking two or more fragments which can be derived retrosynthetically from the formula I. More specifically, suitably substituted starting Indazole derivatives are employed as building blocks in the preparation of the compounds of formula I. If not commercially available, such Indazole derivatives can be prepared according to the well-known standard procedures for the formation of the Indazole ring system. By choosing suitable precursor molecules, these pyrazole syntheses allow the introduction of a variety of substituents into the various positions of the pyrazole system, which can be chemically modified in order to finally arrive at the molecule of the formula I having the desired substituent pattern. As one of the comprehensive reviews in which numerous details and literature references on the chemistry of indazole and on synthetic procedures for their preparation can be found, J. Eiguero in "Comprehensive Heterocyclic Chemistry II"; Eds. A. Katritzky, Ch. Rees, E. Scriven; Elsevier 1996, Vol. 3; W. Stadlbauer in Houben-Weyl, "Methoden der Organischen Chemie" (Methods of Organic Chemistry), Georg Thieme Verlag, Stuttgart, Germany 1994, Vol. E8b Hetarene.

If starting indazole derivatives are not commercially available and have to be synthesized this can be done, for example, according to the well-known indazole syntheses mentioned above. In the following procedures of particular interest for the embodiment of this invention are listed and referenced briefly, however, they are standard procedures comprehensively discussed in the literature, and are well known to one skilled in the art. Although not always shown explicitly, in certain cases positional isomers will occur during the synthesis of the below mentioned reactions. Nevertheless such mixtures of positional isomers, can be separated by modern separation techniques like, for example, preparative HPLC.

1) M. Sisti et al. J. Heterocyclic. Chem. (1989) 26, 531.

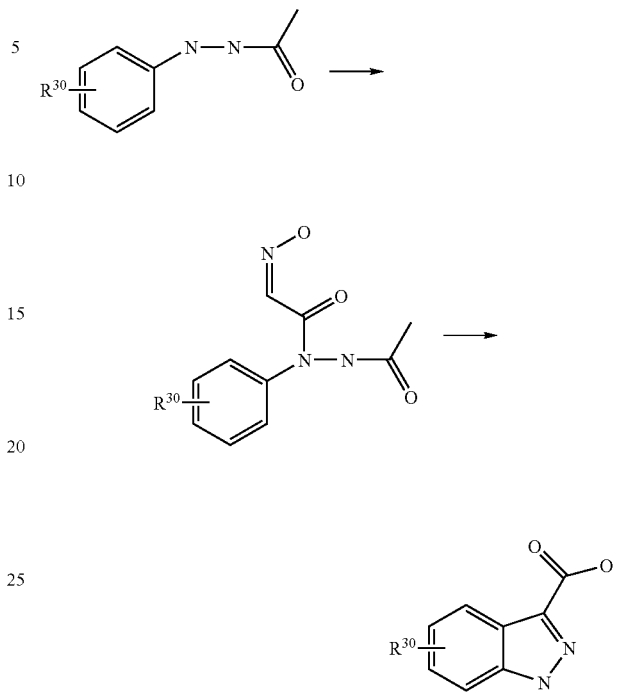

2) a) R. M. Scarborough et al., J. Med. Chem. (1997) 40, 2843.
 b) C. S. Harms et al., J. Med. Chem. (1997) 40, 2843.
 c) A. E. Arfsten et al., J. Med. Chem. (1997) 40, 4308.

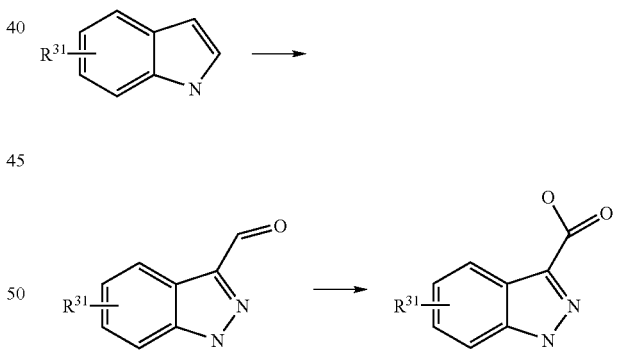

3) a) T. Yoshida et al., Heterocycles (1996) 43, 2701.

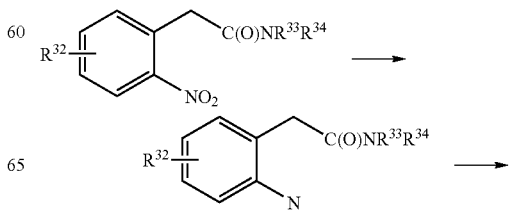

-continued
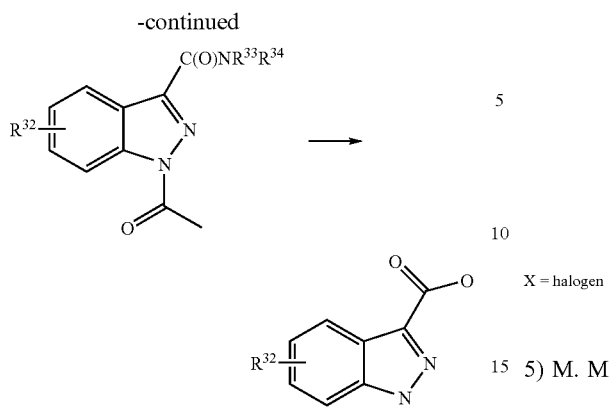
4) a) J. J. Song et al., Tetrahedron Lett. (2001) 42, 2937.
b) J. J. Song et al., Org. Lett. (2000) 2, 519.
-continued
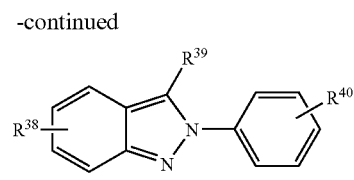
X = halogen
5) M. M. Abdel-Khalik et al., Synthesis (2000) 8, 1166.
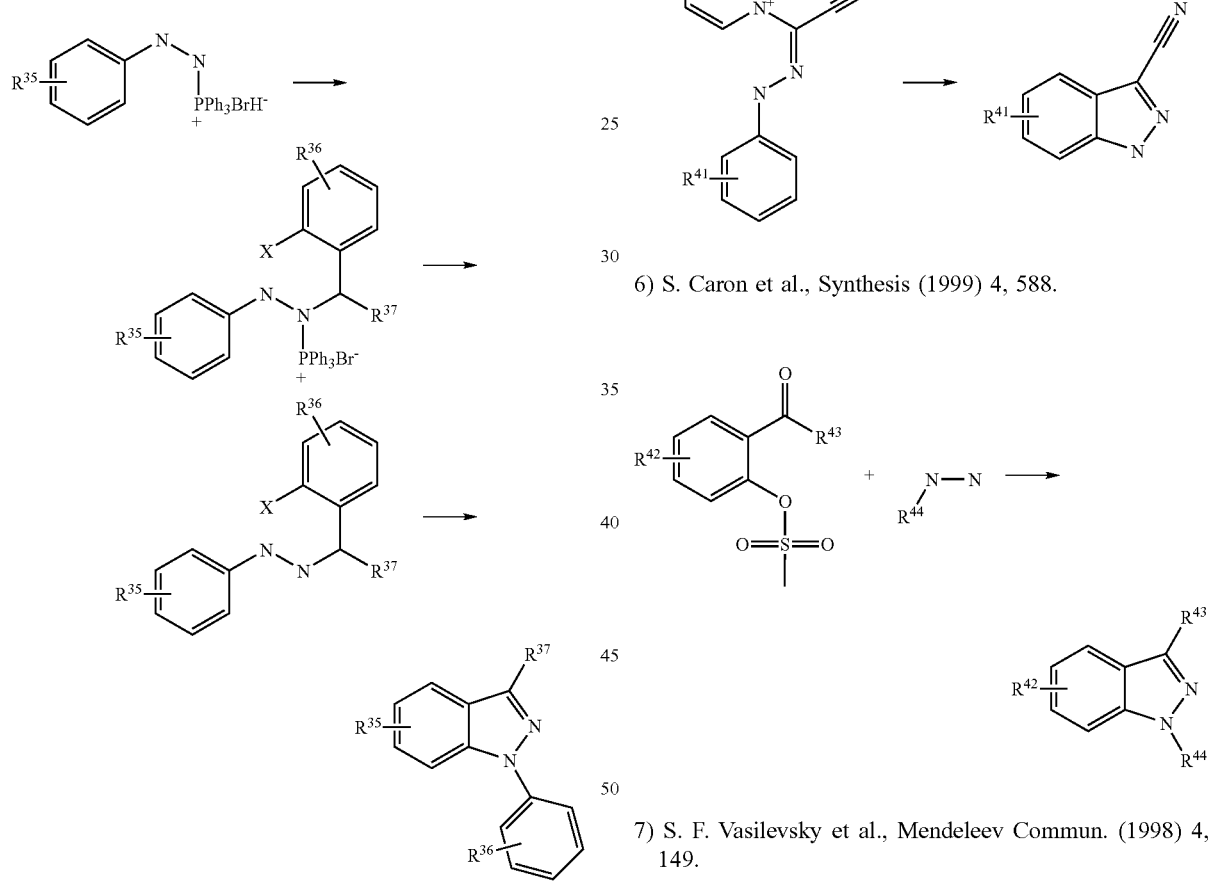
6) S. Caron et al., Synthesis (1999) 4, 588.
7) S. F. Vasilevsky et al., Mendeleev Commun. (1998) 4, 149.
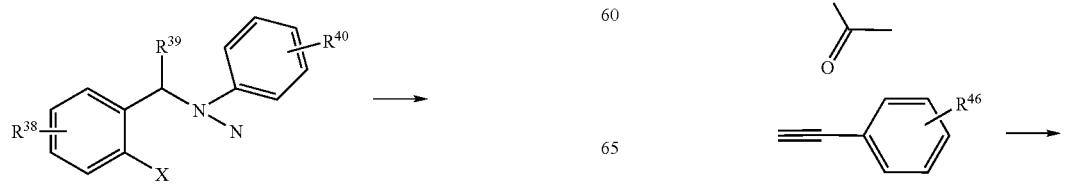

-continued
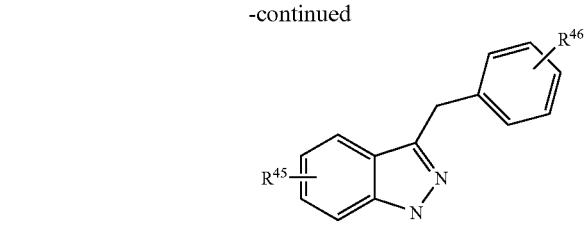
8) a) T. Yoshida et al., Heterocycles (1996) 43, 2701.
   b) D. A. Nugiel et al., J. Org. Chem. (1997) 62, 5627.
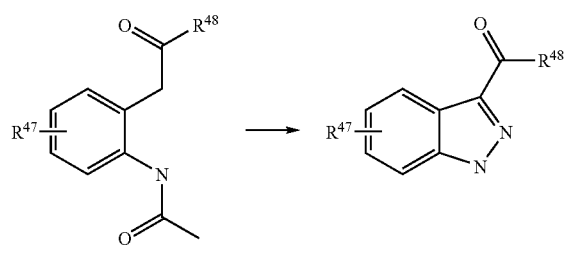
9) a) F. Halley et al., Synth. Commun. (1997) 27, 1199.
   b) A. Walser et al., J. Heterocycl. Chem. (1991) 28, 1121.
   c) G. M. Shutzke et al., J. Heterocycl. Chem. (1997) 34, 1121.
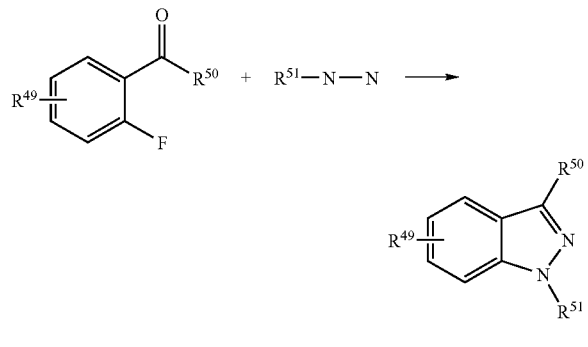
10) K. Turnbull et al., Synth. Commun. (1996) 26, 2757.
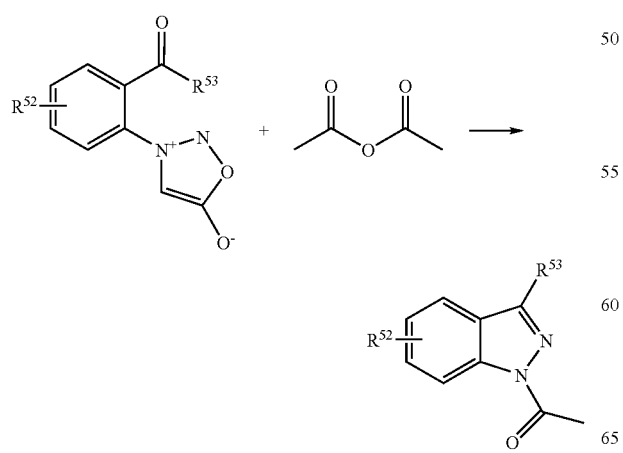
11) a) Z. Zong et al., J. Chem. Soc. Perkin Trans 1 (1993) 1279.
    b) P. G. Baraldi et al., Synthesis (1997) 1140.
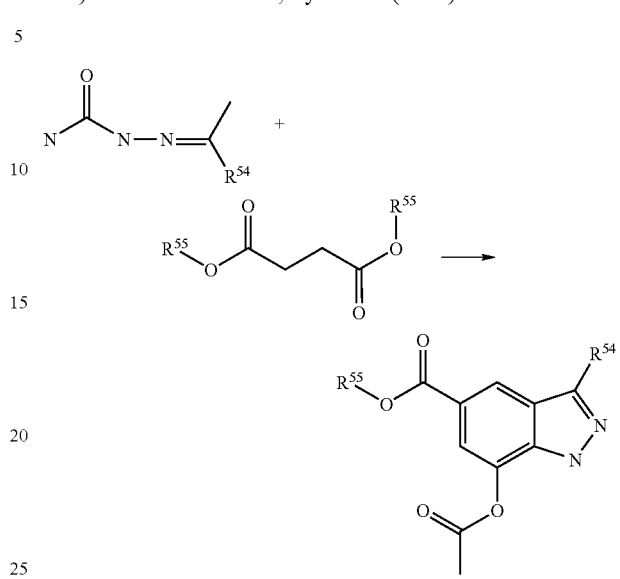
12) R. L. Swett et al., J. Heterocycl. Chem. (1975) 12, 517.
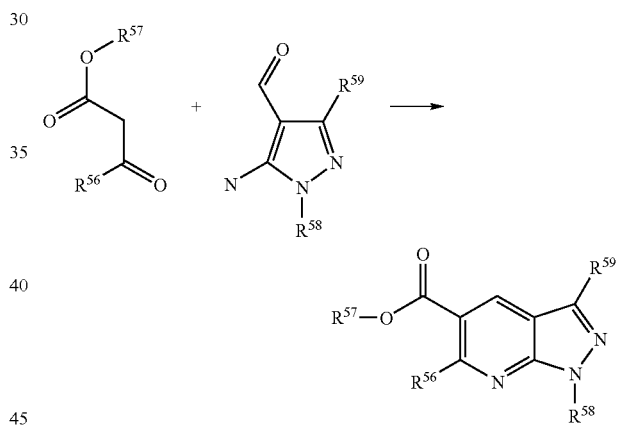
13) Y. Tominaga et al., Tetrahedron Lett. (1995) 47, 8641.
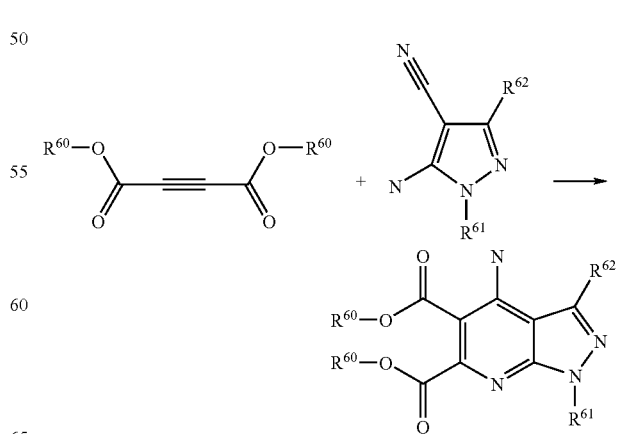

14) V. K. Ahluwalia et al., Synth. Commun. (1996) 26, 1341.
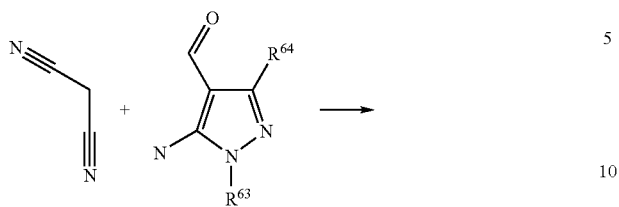
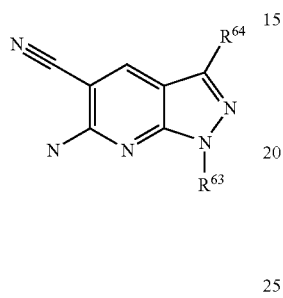
15) F. von Meyenburg et al., Chem. Ber. (1891) 24, 2370.
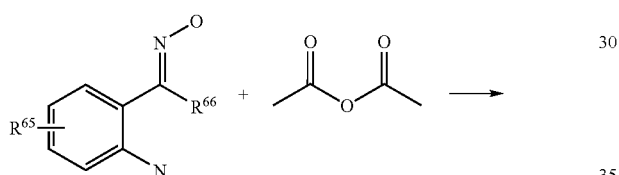
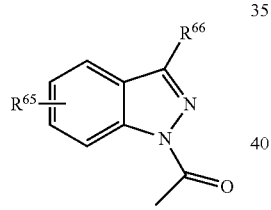
16) B. N. Bradbury et al., J. Chem. Soc. Perkin Trans 1 (1975) 31.
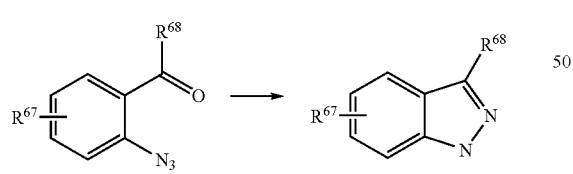
17) B. Gonzalez et al., J. Chem. Res. Miniprint (1985) 1128.
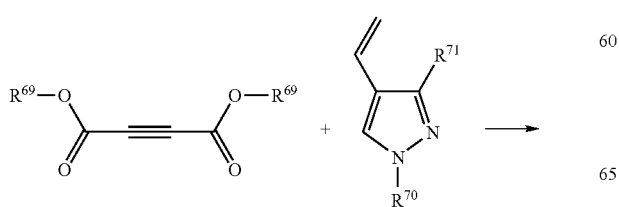
-continued
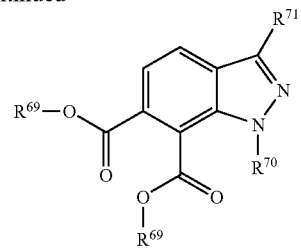
18) a) A. R. Frasca et al., Tetrahedron Lett. (1962) 1115.
b) A. R. Frasca et al., Can. J. Chem. (1967) 45, 697.
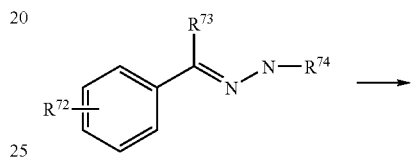
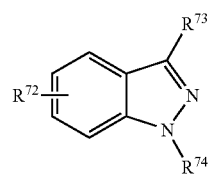
19) K. Turnbull et al., J. Heterocycl. Chem. (1988) 25, 1817.
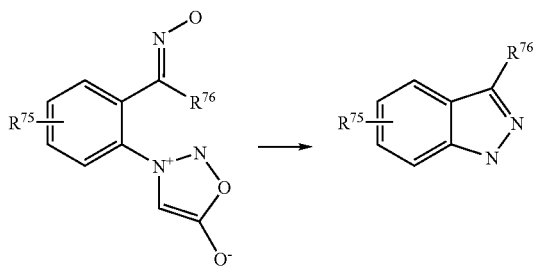
20) C. Tavani et al., Tetrahedron (I1994) 50, 3529.
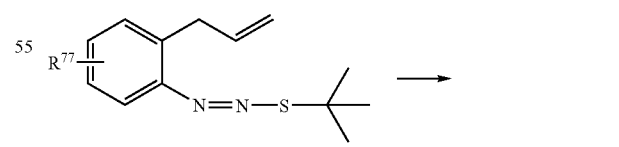
21) a) I. Fujiwara et al., Chem. Pharm Bull. (1995) 43, 1912.
b) G. C. Rigdon et al., J. Med. Chem. (1996) 39, 4692.

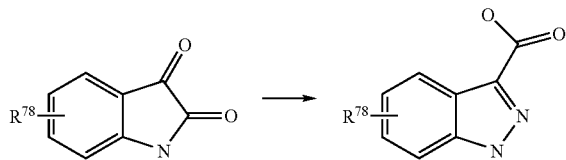

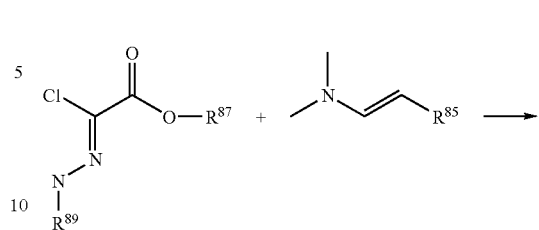

3) N. K. Markova et al., Zh. Org. Khim. (1983) 19, 2281.

Furthermore for those who are skilled in the art it will cause no difficulty to adopt and modify certain procedures describing the synthesis and derivatisation of pyrazoles to indazoles. These procedures are, for example, described by J. Eiguero in "Comprehensive Heterocyclic Chemistry II"; Eds. A. Katritzky, Ch. Rees, E. Scriven; Elsevier 1996, Vol. 3; K. Kirschke in Houben-Weyl, "Methoden der Organischen Chemie" (Methods of Organic Chemistry), Georg Thieme Verlag, Stuttgart, Germany 1994, Vol. E8b Hetarene; T. Nagai et al. Org. Prep. Proced. Int. (1993), 25, 403; M. Elnagdi et al., Heterocycles (1985) 23, 3121; K. Makino et al., J. Heterocycl. Chem. (1998) 35, 489; K. Makino et al., J. Heteterocycl. Chem. (1999) 36, 321.

In particular applying and modiflying procedures for the synthesis of pyrazole derivatives listed and briefly referenced below, can open-up access to valuable intermediates for the synthesis of compounds of the formula I.

1) a) N. Kudo et al. Chem. Pharm. Bull. (1999) 47, 857.
   b) M. Dewar et al. J. Chem. Soc. (1945) 114.
   c) L. J. Smith, J. Am. Chem. Soc. (1949) 71, 2671.
   d) J. Zhang,et al., Bioorg. Med. Chem. Lett. (2000) 10, 2575.

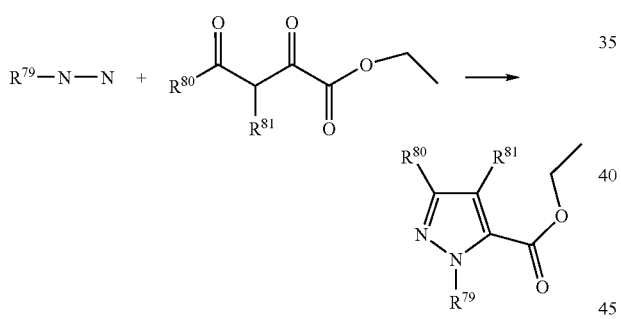

2) a) A. Padwa, J. Heterocycl. Chem. (1987) 24, 1225.
   b) A. W. Erian et al.; Synth Commun. (1999) 29, 1527.

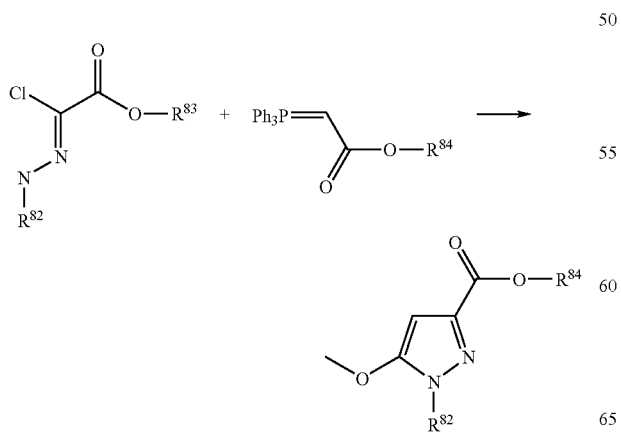

4) P. Bravo et al., Tetrahedron (1994) 50, 8827.

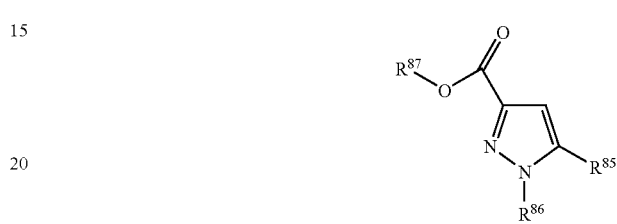

5) a) M. A. Martins et al., Synthesis (1995) 12, 1491.
   b) M. A. Martins et al., J. Heterocycl. Chem. (1999) 36, 217.

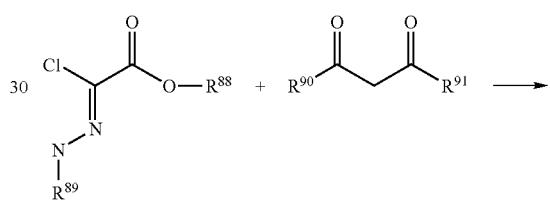

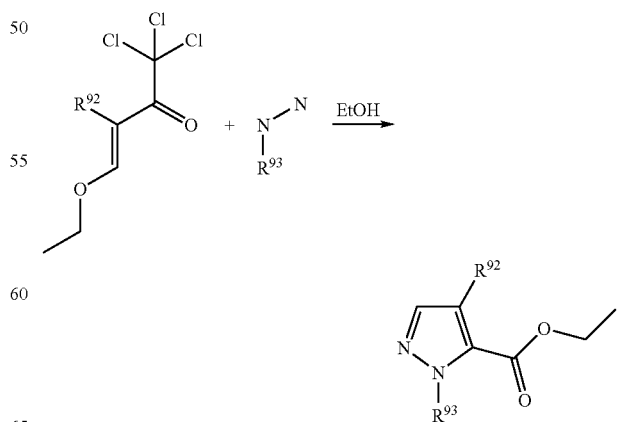

6) R. G. Jones et al., J. Org. Chem. (1955) 20, 1342.
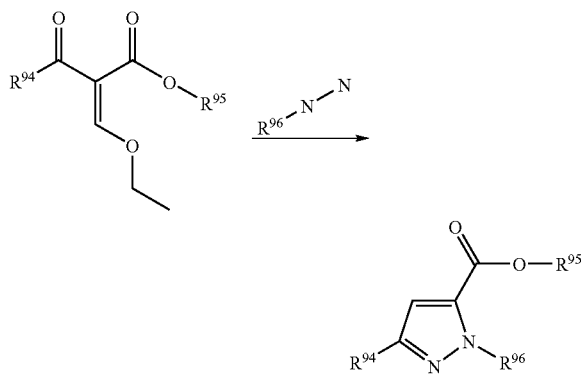
7) W. T. Ashton et al., J. Heterocycl. Chem. (1993) 30, 307.
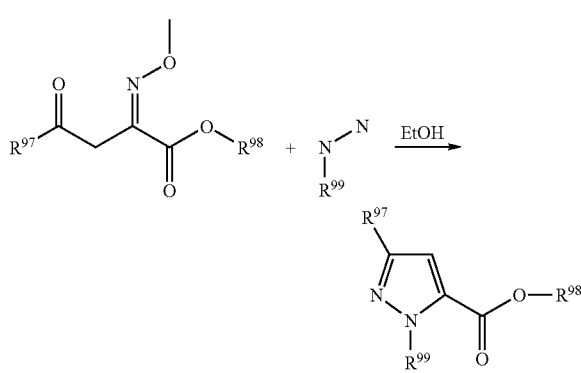
8) a) K. I. Bookernilburn, Synlett, (1992) 327.
   b) G. Heinisch et al., J. Chem. Soc. Perkin. Trans 1 (1990) 1829.
   c) K. Tumbull et al., Org. Prep. Proced. Int. (2000) 32, 593
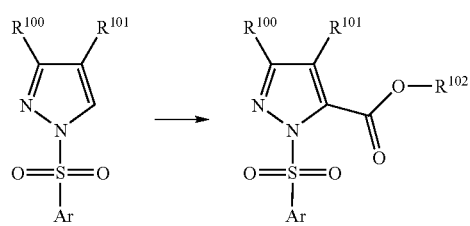
9) F. Farina et al., Heterocycles (1989) 29, 967.
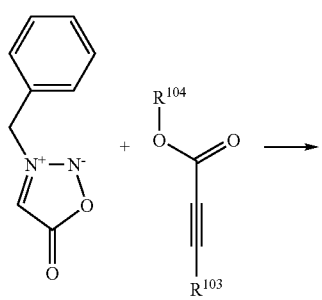
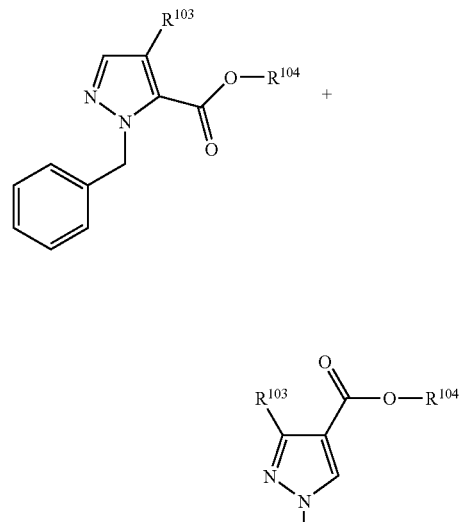
10) T. Haque et al., J. Med. Chem. (2002) 4669.
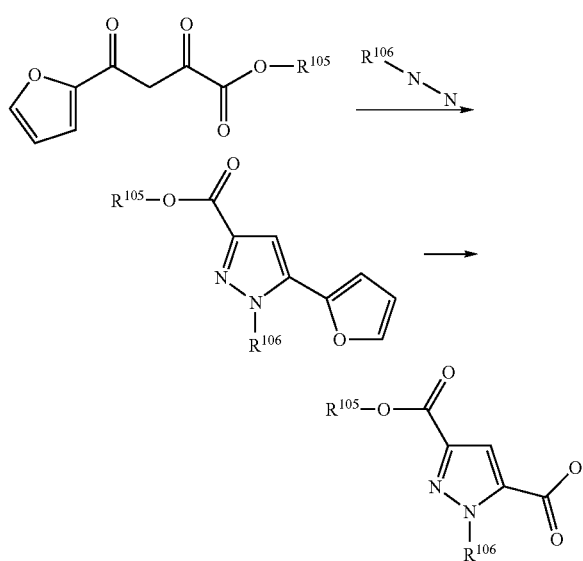
11) H. V. Patel, Synth. Commun. (1991) 21, 1583.
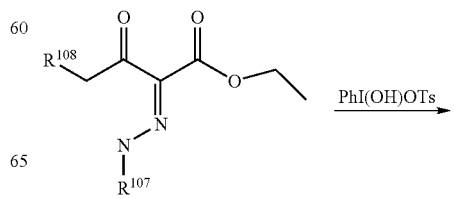

-continued
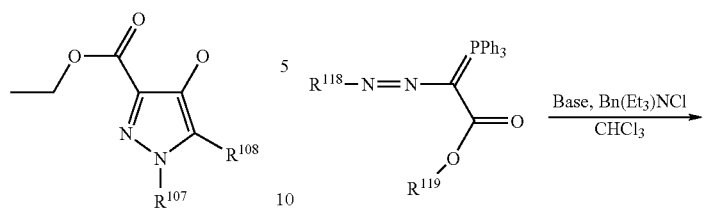
12) F. Farina et al., Heterocycles (1989) 29, 967.
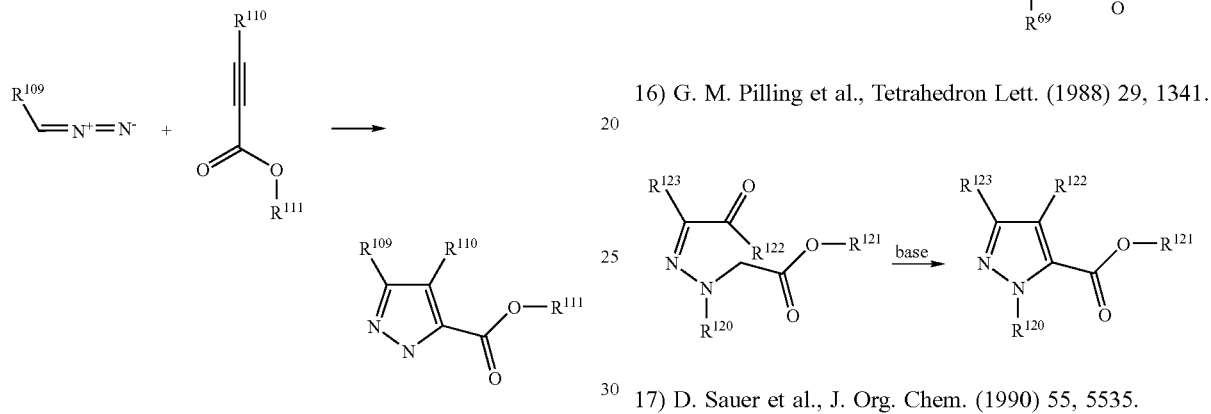
13) R. Huisgen et al., J. Am. Chem. Soc. (1979) 101, 3647.
14) W. Sucrow et al., Angew. Chem., Int. Ed. (1975) 14, 560.
15) C. Baldoli et al., J. Heterocycl. Chem. (1989), 26, 241.
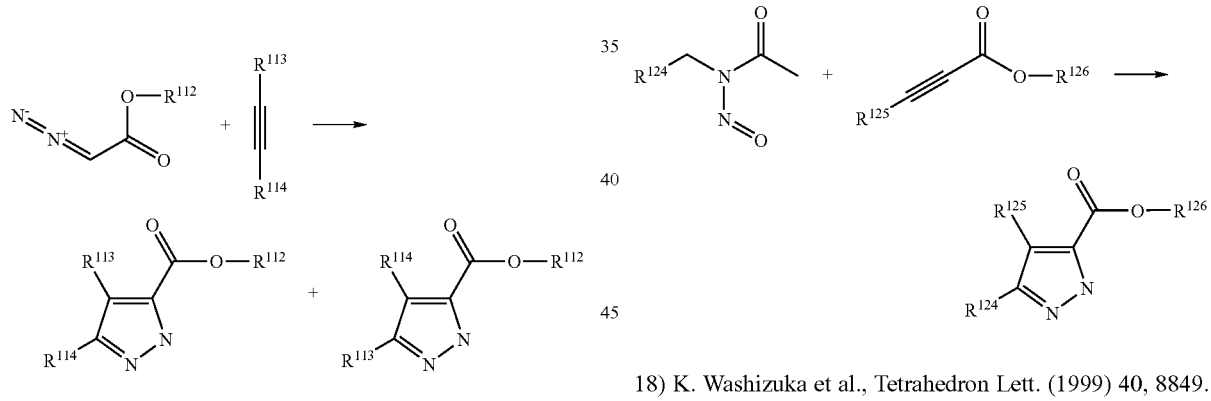
16) G. M. Pilling et al., Tetrahedron Lett. (1988) 29, 1341.
17) D. Sauer et al., J. Org. Chem. (1990) 55, 5535.
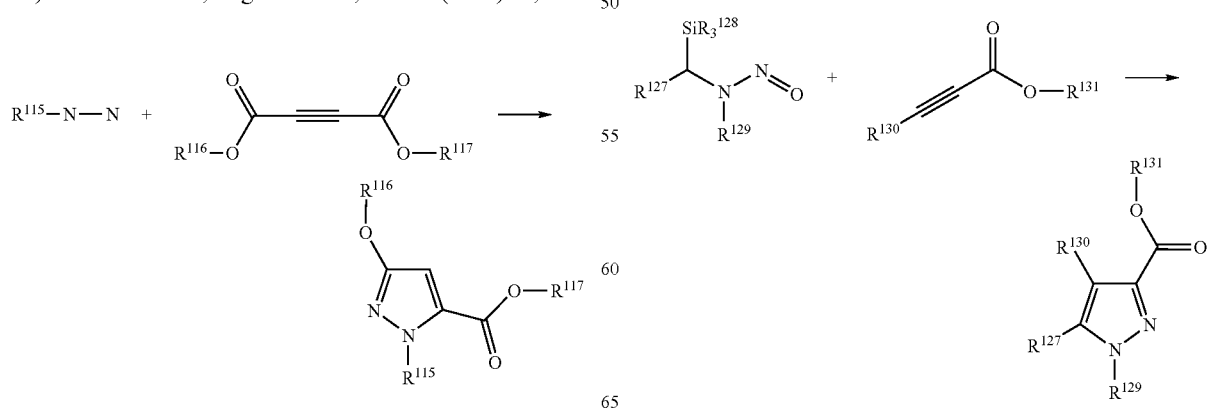
18) K. Washizuka et al., Tetrahedron Lett. (1999) 40, 8849.

19) F. Foti et al., Tetrahedron Lett. (1999) 40, 2605.

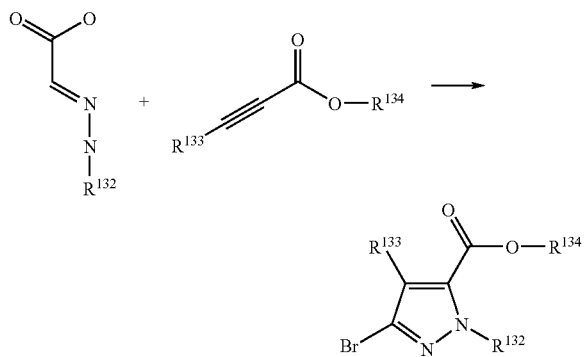

Further, in order to obtain the desired substituents at the indazole ring system in the formula I, the functional groups introduced into the ring system during the indazole synthesis can be chemically modified. Especially the groups present in the indazole ring system can be modified by a variety of reactions and thus the desired residues $R^3$ can be obtained. For example, an indazole carrying hydrogen in the 3-position can also be obtained by saponification and subsequent decarboxylation of indazole carrying an ester group in the respective position. Alkyl- or hydroxymethyl groups as well as formyl groups attached to the indazole core can be transformed to a variety of functional groups, for example, to the corresponding carboxylic acid or carboxylic ester by many oxidative reactions well known to those skilled in the art. Moreover a nitrile group attached to the indazole ring can, for example, easily be converted into the desired acid under acidic or basic conditions. In addition, carboxylic acid groups and acetic acid groups in the 3-position can be converted into their homologues by usual reactions for chain elongation of carboxylic acids. Halogen atoms can be introduced into the 3-position for example according to procedures like the following described in the literature. For the fluorination N-fluoro-2,4,6-trimethylpyridinium triflate is a suitable reagent (T. Umemoto, S. Fukami, G. Tomizawa, K. Harasawa, K. Kawada, K. Tomita, J. Am. Chem. Soc. (1990) 112, 8563 see also K. Manko et al., J. Fluorine Chem. (1988) 39, 435; R. Storer et al. Nucleosides Nucleotides (1999) 18; 203) however, other fluorinating reagents may also be employed where appropriate. The chlorination, brominnation, or iodination of indazoles can be accomplished by the reaction with elemental halogens or by the use of NCS, NBS or NIS and many other reagents well known to those skilled in the art. In addition suitable procedures are, in analogy to the related pyrazoles, for example reported by M. Rodriguez-Franco et al., Tetrahedron Lett. (2001) 42, 863; J. Pawlas et al., J. Org. Chem. (2000) 65, 9001; Y. Huang et al., Org Lett (2000) 2, 2833; W. Holzer et al., J. Heterocycl. Chem. (1995) 32, 1351; N. Kudo et al., Chem. Pharm. Bull. (1999) 47, 857; G. Auzzi et al., Farmaco, Ed Sci (1979) 34, 743; K. Morimoto et al., J. Heterocycl. Chem. (1997) 34, 537; D. Jeon et al., Synth. Commun. (1998) 28, 2159.

Depending on the reaction conditions, reagent, stochiometry and substitution pattern the halogen is introduced in the 3-position. By selective halogen/metal exchange or metalation by selective hydrogen/metal exchange and subsequent reaction with a wide range of electrophiles various substituents can be introduced at the heterocyclic nucleus. (W. M. Welch et al., Synthesis (1992) 937; M. R. Grimmett, Heterocycles (1994) 37, 2087; V. D. Gardner et al., J. Heterocycl. Chem. (1984) 21, 121; D. Butler et al., J. Org. Chem. (1971) 36, 2542). Halogens or hydroxy groups (via their triflates or nonaflates)—or primary amines (via their diazonium salts) present in the indazole structure—can be converted directly, or after interconversion to the corresponding stannane, or boronic acid,into a variety of other functional groups like for example —CN, —CF$_3$, —C$_2$F$_5$, ethers, acids, amides, amines, alkyl- or aryl-groups mediated by means of transition metals, namely palladium or nickel catalysts or copper salts and reagents for example referred to below (F. Diederich, P. Stang, Metal-catalyzed Cross-coupling Reactions, Wiley-VCH, 1998; or M. Beller, C. Bolm, Transition Metals for Organic Synthesis, Wiley-VCH, 1998; J. Tsuji, Palladium Reagents and Catalysts, Wiley, 1996; J. Hartwig, Angew. Chem. (1998) 110, 2154; B. Yang, S. Buchwald, J. Organomet. Chem. (1999) 576, 125; T. Sakamoto, K. Ohsawa, J. Chem. Soc. Perkin Trans 1 (1999) 2323; D. Nichols, S. Frescas, D. Marona-Lewicka, X. Huang, B. Roth, G. Gudelsky, J. Nash, J. Med. Chem. (1994) 37, 4347; P. Lam, C. Clark, S. Saubern, J. Adams, M. Winters, D. Chan, A. Combs, Tetrahedron Lett. (1998) 39,2941; D. Chan, K. Monaco, R. Wang, M. Winters, Tetrahedron Lett. (1998) 39, 2933; V. Farina, V. Krishnamurthy, W. Scott, The Stille Reaction, Wiley, 1994; F. Qing et al. J. Chem. Soc. Perkin Trans. I (1997) 3053; S. Buchwald et al. J. Am. Chem Soc. (2001) 123, 7727; S. Kang et al. Synlett (2002) 3, 427; S. Buchwald et al. Organic Lett. (2002) 4, 581; T. Fuchikami et al. Tetrahedron Lett. (1991) 32, 91; Q. Chen et al. Tetrahedron Lett. (1991) 32, 7689).

For example, nitro groups can be reduced to amino groups by means of various reducing agents, such as sulfides, dithionites, complex hydrides or by catalytic hydrogenation. A reduction of a nitro group may also be carried out at a later stage of the synthesis of a compound of the formula I, and a reduction of a nitro group to an amino group may also occur simultaneously with a reaction performed on another functional group, for example when reacting a group like a cyano group with hydrogen sulfide or when hydrogenating a group. In order to introduce the residues $R^3$, amino groups can then be modified according to standard procedures for alkylation, for example by reaction with (substituted) alkyl halogenides or by reductive amination of carbonyl compounds, according to standard procedures for acylation, for example by reaction with activated carboxylic acid derivatives such as acid chlorides, anhydrides, activated esters or others or by reaction with carboxylic acids in the presence of an activating agent, or according to standard procedures for sulfonylation, for example by reaction with sulfonyl chlorides.

Ester groups present in the indazole nucleus can be hydrolyzed to the corresponding carboxylic acids, which after activation can then be reacted with amines or alcohols under standard conditions to give amides or alcohols, respectively. Ester groups present in the indazole nucleus can be converted to other esters by transesterification. Carboxylic acids attached to a suitable indazole nucleus can also be alkylated to give esters. Ether groups present at the indazole nucleus, for example benzyloxy groups or other easily cleavable ether groups, can be cleaved to give hydroxy groups which then can be reacted with a variety of agents, for example etherification agents or activating agents allowing replacement of the hydroxy group by other groups. Sulfur-containing groups can be reacted analogously.

During the course of the synthesis in order to modify the groups $R^{136}$ or $R^{8'}$ attached to the indazole ring system by application of parallel synthesis methodology, a variety of reactions can be extremely useful, including, for example, palladium, nickel or copper catalysis. Such reactions are described for example in F. Diederich, P. Stang, Metal-catalyzed Cross-coupling Reactions, Wiley-VCH (1998); or M. Beller, C. Bolm, Transition Metals for Organic Synthesis, Wiley-VCH (1998); J. Tsuji, Palladium Reagents and Catalysts, Wiley (1996); J. Hartwig, Angew. Chem. (1998) 110, 2154; B. Yang, S. Buchwald, J. Organomet. Chem. (1999) 576, 125; P. Lam, C. Clark, S. Saubern, J. Adams, M. Winters, D. Chan, A. Combs, Tetrahedron Lett. (1998) 39, 2941; D. Chan, K. Monaco, R. Wang, M. Winters, Tetrahedron Lett. (1998) 39, 2933; J. Wolfe, H. Tomori, J. Sadight, J. Yin, S. Buchwald, J. Org. Chem. (2000) 65, 1158; V. Farina, V. Krishnamurthy, W. Scott, The Stille Reaction, Wiley, (1994); S. Buchwald et al., J. Am. Chem. Soc. (2001) 123, 7727; S. Kang et al., Synlett (2002) 3, 427; S. Buchwald et al., Org. Lett. (2002) 4, 581.

The previously-mentioned reactions for the conversion of functional groups are furthermore, in general, extensively described in textbooks of organic chemistry like M. Smith, J. March, March's Advanced Organic Chemistry, Wiley-VCH, 2001 and in treatises like Houben-Weyl, "Methoden der Organischen Chemie" (Methods of Organic Chemistry), Georg Thieme Verlag, Stuttgart, Germany, or "Organic Reactions", John Wiley & Sons, New York, or R. C. Larock, "Comprehensive Organic Transformations", Wiley-VCH, $2^{nd}$ ed (1999), B. Trost, I. Fleming (eds.) Comprehensive Organic Synthesis, Pergamon, 1991; A. Katritzky, C. Rees, E. Scriven Comprehensive Heterocyclic Chemistry II, Elsevier Science, 1996) in which details on the reactions and primary source literature can be found. Due to the fact that in the present case the functional groups are attached to an indazole ring it may in certain cases become necessary to specifically adapt reaction conditions or to choose specific reagents from a variety of reagents that can in principle be employed into a conversion reaction, or otherwise to take specific measures for achieving a desired conversion, for example to use protection group techniques. However, finding out suitable reaction variants and reaction conditions in such cases does not cause any problems for one skilled in the art.

The structural elements present in the residues attached at the 1-position or 2-position of the indazole ring in the compounds of the formula I and in the $COR^{8'}$ group present in the 3-position of the indazole ring can be introduced into the starting indazole derivative obtainable as outlined above by consecutive reaction steps using synthesis methodologies like those outlines below using procedures which per se are well known to one skilled in the art. The sequence described below can be completely transferred to compounds of the formula Ib as outlined.

The residues $R^{8'}$ that can be introduced in formula 2, for example, by condensing a corresponding carboxylic acid of the formula 2 with a compound of the formula $HR^{8'}$, i.e. with an amine of the formula $HN(R^{1'})R^{2't}$—V-G-M to give a compound of the formula 3. The compound of the formula 3 thus obtained can already contain the desired final groups, i.e. the groups $R^{8'}$ and $R^{136}$ can be the groups —$N(R^1)$—$R^2$—V-G-M and $R^0$-Q- as defined in the formula I, or optionally in the compound of the formula 3 thus obtained subsequently the residue or the residues $R^{8'}$ and the residue $R^{136}$ are introduced or converted into the residues —$N(R^1)R^2$—V-G-M and $R^0$-Q-, respectively, to give the desired compound of the formula I, wherein $J_1$ is N and $J_2$ is N—Q—$R^0$.

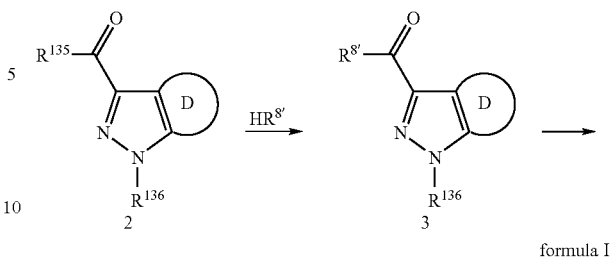

formula I

Thus, the residues $R^{8'}$ and the residues $R^{1'}$ and $R^{2't}$—V-G-M contained therein can have the denotations of $R^1$ and $R^2$—V-G-M, respectively, given above or in addition in the residues $R^{1'}$ and $R^{2't}$—V-G-M functional groups can also be present in the form of groups that can subsequently be transformed into the final groups $R^1$ and $R^2$—V-G-M, i.e. functional groups can be present in the form of precursor groups or of derivatives, for example in protected form. In the course of the preparation of the compounds of the formula I it can generally be advantageous or necessary to introduce functional groups which reduce or prevent undesired reactions or side reactions in the respective synthesis step, in the form of precursor groups which are later converted into the desired functional groups, or to temporarily block functional groups by a protective group strategy suited to the synthesis problem. Such strategies are well known to those skilled in the art (see, for example, Greene and Wuts, Protective Groups in Organic Synthesis, Wiley, 1991, or P. Kocienski, Protecting Groups, Thieme 1994). As examples of precursor groups nitro groups and cyano groups may be mentioned which can in a later step be transformed into carboxylic acid derivatives or by reduction into aminomethyl groups, or nitro groups which may be transformed by reduction, for example catalytic hydrogenation into amino groups by reduction. Protective groups can also have the meaning of a solid phase, and cleavage from the solid phase stands for the removal of the protective group. The use of such techniques is known to those skilled in the art (Burgess K (Ed.) Solid Phase Organic Synthesis, New York, Wiley, 2000). For example, a phenolic hydroxy group can be attached to a trityl-polystyrene resin, which serves as a protecting group, and the molecule is cleaved from this resin by treatment with TFA at a later stage of the synthesis.

The residue $R^{136}$ in the compounds of the formulae 2 and 3 can denote the group -Q-$R^0$ as defined above which finally is to be present in the desired target molecule of the formula I, or it can denote a group which can subsequently be transformed into the group -Q-$R^0$, for example a precursor group or a derivative of the group -Q-$R^0$ in which functional groups are present in protected form, or $R^{136}$ can denote hydrogen or a protective group for the nitrogen atom of the indazole ring. Similarly, the residue $R^3$ in the formulae 2 and 3 have the corresponding definitions of $R^3$ in formula I as defined above, however, for the synthesis of the compounds of the formula I these residues, too, can in principle be present at the stage of the condensation of a compound of the formula 2 with a compound of the formula $HR^{8'}$ giving a compound of the formula 3 in the form of precursor groups or in protected form.

The residues $R^{135}$ in the compounds of the formula 2 which can be identical or different, can be, for example, hydroxy or $(C_1$-$C_4)$-alkoxy, i.e., the groups $COR^{135}$ present in the compounds of the formula 2 can be, for example, the free carboxylic acids or esters thereof like alkyl esters as can be the groups $COR^{8'}$ in the compounds of the formula I. The groups $COR^{135}$ can also be any other activated derivative of a carboxylic acid which allows amide formation, ester formation or thioester formation with a compound of the formula $HRR^{8'}$. The group $COR^{135}$ can be, for example, an acid chloride, an activated ester like a substituted phenyl ester or an N-hydroxysuccinimide or a hydroxybenzotriazole ester, an azolide like an imidazolide, an azide or a mixed anhydride, for example a mixed anhydride with a carbonic acid ester or with a sulfonic acid, which derivatives can all be prepared from the carboxylic acid by standard procedures and can be reacted with an amine, an alcohol or a mercaptan of the formula $HR^{8'}$ under standard conditions. A carboxylic acid group COOH representing $COR^{135}$ in a compound of the formula 2 can be obtained, for example, from an ester group introduced into the indazole system during a indazole synthesis by standard hydrolysis procedures. It can also be obtained, for example, by hydrolysis of a nitrile group introduced into the indazole system during an indazole sysnthesis.

Compounds of the formula I in which a group $COR^{8'}$ is an ester group can also be prepared from compounds of the formula 2 in which $COR^{135}$ is a carboxylic acid group by common esterification reactions like, for example, reacting the acid with an alcohol under acid catalysis, or alkylation of a salt of the carboxylic acid with an electrophile like an alkyl halogenide, or by transesterification from another ester. Compounds of the formula I in which a group $COR^{8'}$ is an amide group can be prepared from amines and compounds of the formula 2 in which $COR^{135}$ is a carboxylic acid group or an ester thereof by common amination reactions. Especially for the preparation of amides the compounds of the formula 2 in which $COR^{135}$ is a carboxylic acid group can be condensed under standard conditions with compounds of the formula $HR^{8'}$ which are amines by means of common coupling reagents used in peptide synthesis. Such coupling reagents are, for example, carbodiimides like dicyclohexylcarbodiimide (DCC) or diisopropylcarbodiimide, carbonyldiazoles like carbonyldiimidazole (CDI) and similar reagents, propylphosphonic anhydride, O-((cyano-(ethoxycarbonyl)-methylene)amino)-N,N,N',N'-tetramethyluronium tetrafluoroborate (TOTU), diethylphosphoryl cyanide (DEPC) or bis-(2-oxo-3-oxazolidinyl)-phosphoryl chloride (BOP-Cl) and many others.

If the residue $-Q-R^0$ present in an indazole of the formula I or the residue $R^{136}$ present in an indazole of the formula 2, or a residue in which functional groups within the residue $-Q-R^0$ or $R^{136}$ are present in protected form or in the form of a precursor group, have not already been introduced during a preceding step, for example during a synthesis of the indazole nucleus, these residues can, for example, be introduced into the 1-position of the indazole system by conventional literature procedures well known to one skilled in the art for N-alkylation, reductive amination, N-arylation, N-acylation or N-sulfonylation of ring nitrogen atoms of heterocycles. The starting indazole derivative that is to be employed in such a reaction carries hydrogen in the 1-position. N-Alkylation of a ring nitrogen atom can, for example, be performed under standard conditions, preferably in the presence of a base like $K_2CO_3$, $Cs_2CO_3$, NaH or KO$^t$Bu, using an alkylating compound of the formula LG-Q-$R^0$ or of the formula $R^{136}$-LG, wherein the atom in the group Q or in the group $R^{136}$ bonded to the group LG in this case is an aliphatic carbon atom of an alkyl moiety and LG is a leaving group, for example halogen like chlorine, bromine or iodine, or a sulfonyloxy group like tosyloxy, mesyloxy or trifluormethylsulfonyloxy. LG may, for example, also be a hydroxy group which, in order to achieve the alkylation reaction, is activated in a well-known Mitsunobu reaction by a conventional activating agent. The regioselectivity of the N-alkylation can be controlled by the choice of the base, solvent and reaction conditions. Nevertheless mixtures of positional isomers, can be separated by modern separation techniques like, for example, flash chromatography, crystallisation or preparative HPLC.

The sequence described above for compounds of the formula I, wherein $J_1$ is N and $J_2$ is $N-Q-R^0$, can be completely transferred to compounds of the formula I, wherein $J_2$ is N and $J_1$ is $N-Q-R^0$, as outlined by the scheme below.

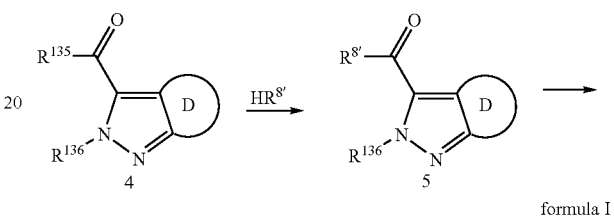

formula I

For the preparation of compounds in which A is a direct linkage and an aromatic group is directly bonded to the 1-position or 2-position of the indazole system, conventional arylation procedures can be used. For example aryl fluorides like alkyl fluorobenzoates or 4-fluorophenyl nitriles can be employed as arylating agents. Such processes are described, for example, by K. Cooper et al., J.Med.Chem. (1992), 35, 3115; M. Artico et al., Eur.J.Med.Chem.Chim.Ther. (1992) 27, 219; X.-J. Wang et al., Tetrahedron Letters (2000) 41, 5321; M. L. Cerrada et al., Synth. Commun. (1993) 23, 1947. Alternatively a wide variety of substituted aryl iodides, aryl bromides or aryl triflates can serve as arylating agents at the 1-position or 2-position of the heterocyclic nitrogen in a copper salt or palladium mediated reaction according for example to P. Cozzi et al. Farmaco (1987) 42, 205; P. Unangst, D. Connor, R. Stabler, R. Weikert, J. Heterocycl. Chem. (1987) 24, 811; G. Tokmakov, I. Grandberg, Tetrahedron (1995) 51, 2091; D. Old, M. Harris, S. Buchwald, Org. Lett. (2000) 2, 1403, G. Mann, J. Hartwig, M. Driver, C. Femandez-Rivas, J. Am. Chem. Soc. (1998) 120, 827; J. Hartwig, M. Kawatsura, S. Hauk, K. Shaughnessy, L. J. Org. Chem. (1999) 64, 5575; S. Buchwald et al., J. Am. Chem. Soc. (2001) 123, 7727. Moreover such arylations can also be accomplished by reaction of a wide range of substituted aryl boronic acids as demonstrated for example by P. Lam et al., Tetrahedron Lett. (1998) 39, 2941; V. Collot et al., Tetrahedron Lett. (2000) 41, 9053; P. Lam et al., Tetrahedron Lett. (2001) 42, 3415;

Preferred methods include, but are not limited to those described in the examples.

The compounds of the present invention are serine protease inhibitors, which inhibit the activity of the blood coagulation enzyme factors Xa and/or factor VIIa. In particular, they are highly active inhibitors of factor Xa. They are specific serine protease inhibitors inasmuch as they do not substantially inhibit the activity of other proteases whose inhibition is not desired. The activity of the compounds of the formula I can be determined, for example, in the assays described below or in other assays known to those skilled in the art. With respect to factor Xa inhibition, a preferred embodiment of the invention comprises compounds which have a Ki<1 mM for factor Xa inhibition as determined in the assay described below, with or without concomitant factor VIIa inhibition, and which preferably do not substantially inhibit the activity of other proteases involved in coagulation and fibrinolysis whose inhibition is not desired (using the same concentration of the inhibitor). The compounds of the invention inhibit factor Xa catalytic activity either directly, within the prothrombinase complex or as a soluble subunit, or indirectly, by inhibiting the assembly of factor Xa into the prothrombinase complex.

As inhibitors of factor Xa and/or factor VIIa the compounds of the formula I and their physiologically tolerable salts and their prodrugs are generally suitable for the therapy and prophylaxis of conditions in which the activity of factor Xa and/or factor VJIa plays a role or has an undesired extent, or which can favorably be influenced by inhibiting factor Xa and/or factor VIIa or decreasing their activities, or for the prevention, alleviation or cure of which an inhibition of factor Xa and/or factor VIIa or a decrease in their activity is desired by the physician. As inhibition of factor Xa and/or factor VIIa influences blood coagulation and fibrinolysis, the compounds of the formula I and their physiologically tolerable salts and their prodrugs are generally suitable for reducing blood clotting, or for the therapy and prophylaxis of conditions in which the activity of the blood coagulation system plays a role or has an undesired extent, or which can favorably be influenced by reducing blood clotting, or for the prevention, alleviation or cure of which a decreased activity of the blood coagulation system is desired by the physician. A specific subject of the present invention thus are the reduction or inhibition of unwanted blood clotting, in particular in an individual, by administering an effective amount of a compound I or a physiologically tolerable salt or a prodrug thereof, as well as pharmaceutical preparations therefore.

The present invention also relates to the compounds of the formula I and/or their physiologically tolerable salts and/or their prodrugs for use as pharmaceuticals (or medicaments), to the use of the compounds of the formula I and/or their physiologically tolerable salts and/or their prodrugs for the production of pharmaceuticals for inhibition of factor Xa and/or factor VIa or for influencing blood coagulation, inflammatory response or fibrinolysis or for the therapy or prophylaxis of the diseases mentioned above or below, for example for the production of pharmaceuticals for the therapy and prophylaxis of cardiovascular disorders, thromboembolic diseases or restenoses. The invention also relates to the use of the compounds of the formula I and/or their physiologically tolerable salts and/or their prodrugs for the inhibition of factor Xa and/or factor VIIa or for influencing blood coagulation or fibrinolysis or for the therapy or prophylaxis of the diseases mentioned above or below, for example for use in the therapy and prophylaxis of cardiovascular disorders, thromboembolic diseases or restenoses, and to methods of treatment aiming at such purposes including methods for said therapies and prophylaxis. The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i.e. one or more pharmaceutically acceptable carrier substances or excipients and/or auxiliary substances or additives.

The invention also relates to the treatment of disease states such as abnormal thrombus formation, acute myocardial infarction, unstable angina, thromboembolism, acute vessel closure associated with thrombolytic therapy or percutaneous transluminal coronary angioplasty (PTCA), transient ischemic attacks, stroke, intermittent claudication or bypass grafting of the coronary or peripheral arteries, vessel luminal narrowing, restenosis post coronary or venous angioplasty, maintenance of vascular access patency in long-term hemodialysis patients, pathologic thrombus formation occurring in the veins of the lower extremities following abdominal, knee or hip surgery, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The compounds of the present invention can also be used to reduce an inflammatory response. Examples of specific disorders for the treatment or prophylaxis of which the compounds of the formula I can be used are coronary heart disease, myocardial infarction, angina pectoris, vascular restenosis, for example restenosis following angioplasty like PTCA, adult respiratory distress syndrome, multi-organ failure and disseminated intravascular clotting disorder. Examples of related complications associated with surgery are thromboses like deep vein and proximal vein thrombosis, which can occur following surgery.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations, which permit enteral or parenteral administration.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carriers being used in addition to the compound(s) of the formula I and/or its (their) physiologically tolerable salts and/or its (their) prodrugs. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 mg to about 1000 mg, preferably from about 1 mg to about 500 mg.

In addition to the active ingredients of the formula I and/or their physiologically acceptable salts and/or prodrugs and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I, and/or their physiologically tolerable salts and/or their prodrugs. In case a pharmaceutical preparation contains two or more compounds of the formula I, the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physico-chemical properties of the compounds and thus allows the selection of such desired compounds. Furthermore, in addition to at least one compound of the formula I and/or a physiologically tolerable salt and/or its prodrug, the pharmaceutical preparations can also contain one or more other therapeutically or prophylactically active ingredients.

When using the compounds of the formula I the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from 0.01 mg/kg to 100 mg/kg, preferably from 0.1 mg/kg to 50 mg/kg, in particular from 0. 1 mg/kg to 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

A compound of the formula I can also advantageously be used as an anticoagulant outside an individual. For example, an effective amount of a compound of the invention can be contacted with a freshly drawn blood sample to prevent coagulation of the blood sample. Further, a compound of the formula I or Ib its salts can be used for diagnostic purposes, for example in in vitro diagnoses, and as an auxiliary in biochemical investigations. For example, a compound of the formula I can be used in an assay to identify the presence of factor Xa and/or factor VIIa or to isolate factor Xa and/or factor VIIa in a substantially purified formr. A compound of the invention can be labeled with, for example, a radioisotope, and the labeled compound bound to factor Xa and/or factor VIIa is then detected using a routine method useful for detecting the particular label. Thus, a compound of the formula I or a salt thereof can be used as a probe to detect the location or amount of factor Xa and/or factor VIIa activity in vivo, in vitro or ex vivo.

Furthermore, the compounds of the formula I can be used as synthesis intermediates for the preparation of other compounds, in particular of other pharmaceutical active ingredients, which are obtainable from the compounds of the formula I, for example by introduction of substituents or modification of functional groups.

The general synthetic sequences for preparing the compounds useful in the present invention are outlined in the examples given below. Both an explanation of, and the actual procedure for, the various aspects of the present invention are described where appropriate. The following examples are intended to be merely illustrative of the present invention, and not limiting thereof in either scope or spirit. Those with skill in the art will readily understand that known variations of the conditions and processes described in the examples can be used to synthesize the compounds of the present invention.

It is understood that changes that do not substantially affect the activity of the various embodiments of this invention are included within the invention disclosed herein. Thus, the following examples are intended to illustrate but not limit the present invention.

EXAMPLES

When in the final step of the synthesis of a compound an acid such as trifluoroacetic acid or acetic acid was used, for example when trifluoroacetic acid was employed to remove a tBu group or when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt or hydrochloric acid salt.

| Abbreviations used: | |
| --- | --- |
| tert-Butyl | tBu |
| 2,2'-bis(diphenylphoshino-1,1'-binaphthyl | Binap |
| Bis-(oxo-3-oxazolidinyl)-phosphoryl chloride | BOP-Cl |
| dibenzylidenacetone | dba |
| Dichloromethane | DCM |
| Dicyclohexyl-carbodiimide | DCC |
| Diethylphosphoryl cyanide | DEPC |
| 4-Dimethyaminopyridine | DMAP |
| N,N-Dimethylformamide | DMF |
| Dimethylsulfoxide | DMSO |
| 1,1'-Bis(diphenylphosphino)ferrocene | DPPF |
| O-(7-Azabenzotriazol-1-yl)-N,N,N',N'-tetramethyluronium-hexafluorophosphate | HATU |
| N-Bromosuccinimide | NBS |
| N-Chlorosuccinimide | NCS |
| N-Iodosuccinimide | NIS |
| N-Ethylmorpholine | NEM |
| Methanol | MeOH |
| Room temperature 20° C. to 25° C. | RT |
| Saturated | sat. |
| Tetrahydrofuran | THF |
| Trifluoroacetic acid | TFA |
| O-((Ethoxycarbonyl)cyanomethyleneamino)-N,N,N',N'-tetramethyluronium tetrafluoroborate | TOTU |

Example 1

1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester (i) 3-Formyl-1H-indazole-5-carboxylic acid methyl ester To a solution of 2 g NaNO$_2$ in 100 mL THF and 50 mL water, 500 mg 1H-Indole-5-carboxylic acid methyl ester were added. The solution was cooled to 0° C. and 7 mL half concentrated hydrochloric acid were added dropwise. After stirring for 4 days, the reaction mixture was extracted with ethyl acetate (3×100 mL) and the combined organic layers were washed with brine (1×50 mL) and dried over MgSO$_4$. Filtration and evaporation of the solvents under reduced pressure yielded 551 mg crude product which was recrystallized from heptane/ethyl acetate to yield a bright yellow solid.

Yield: 318 mg.

(ii) 1-[5-(5-Chloro-thiophen-2-yl)-isoxazol-3-ylmethyl]-3-formyl-1H-indazole-5-carboxylic acid methyl ester To a solution of 200 mg 3-Formyl-1H-indazole-5-carboxylic acid methyl ester in 4 mL DMF, 273 mg 3-Bromomethyl-5-(5-chloro-thiophen-2-yl)-isoxazole [prepared by adopting a procedure described by Ewing, William R.; Becker, Michael R.; Choi-Sledeski, Yong Mi; Pauls, Heinz W.; He, Wei; Condon, Stephen M.; Davis, Roderick S.; Hanney, Barbara A.; Spada, Alfred P.; Burns, Christopher J.; Jiang, John Z.; Li, Aiwen; Myers, Michael R.; Lau, Wan F.; Poli, Gregory B; PCT Int. Appl. (2001) 460 pp. WO 0107436 A2] and 320 mg Cs$_2$CO$_3$ were added and the mixture was stirred at room temperature for 1.5 h. This crude reaction mixture was subjected to the subsequent oxidation step.

(iii) 1-[5-(5-Chloro-thiophen-2-yl)-isoxazol-3-ylmethyl]-1H-indazole-3,5-dicarboxylic acid 5-methyl ester To the reaction mixture of the foregoing step 18.7 mL 2-Methylbutene (2M in THF) were added at 0° C. Then a solution of 886 mg NaClO$_2$ (80%) and 940 mg NaH$_2$PO$_4$ in 10 mL water was added dropwise. After complete addition, the reaction mixture was warmed to RT and stirred for 2 h. Finally, 4.5 mL half concentrated hydrochloric acid were added and the mixture was extracted with ethyl acetate (3×100 mL). The combined organic layers were washed with brine (1×50 mL) and dried over MgSO$_4$. Removal of the solvents under reduced pressure yielded the crude product which was used in the next reaction step without further purification.

Yield: 480 mg.

(i) (1-Isopropyl-piperidin-4-yl)-carbamic acid tert-butyl ester

To a solution of 5.0 g Piperidin-4-yl-carbamic acid tert-butyl ester in 15 mL methanol, 7.34 mL acetone, 3.14 g Na(CN)BH$_3$ and 0.3 mL acetic acid were added. After stirring for 16 h at RT the solvent was removed under reduced pressure and the residue was partitioned between 30 mL of water and 30 mL of ethyl acetate. The organic layer was washed with saturated Na$_2$CO$_3$ solution, water and then dried over Na$_2$SO$_4$. Following filtration, the solvent was removed under reduced pressure to yields a white solid. Yield: 4.8 g MS (ES$^+$): m/e=243.

(ii) 1-Isopropyl-piperidin-4-ylamine

To 4.8 g (1-Isopropyl-piperidin-4-yl)-carbamic acid tert-butyl ester in 15 mL methanol, 20 mL methanolic hydrochloric acid (8M) were added and the mixture was stirred for 16 h. Removal of the solvent under reduced pressure yielded a white solid, which was coevaporated twice with 20 mL toluene. The product was obtained as its hydrochloride.

Yield: 5.42 g MS (ES$^+$): m/e=143.

(iv) 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester To 480 mg 1-[5-(5-Chloro-thiophen-2-yl)-isoxazol-3-ylmethyl]-1H-indazole-3,5-dicarboxylic acid 5-methyl ester in 5 mL DCM and 0.6 mL NEt$_3$, 253 mg 1-Isopropyl-piperidin-4-ylamine hydrochloride and 250 mg BOP-Cl were added at RT and the mixture was stirred for 3 h. After addition of 20 mL of water the reaction mixture was extracted with ethyl acetate (3×50 mL). The combined organic layers were washed with water (1×30) and brine (1×50 mL) and then dried over MgSO$_4$. After removal of the solvent under reduced pressure the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 210 mg MS (ES$^+$): m/e=542, chloro pattern.

Alternatively 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester was prepared by the following procedure:

(i) 1H-Indazole-3,5-dicarboxylic acid 5-methyl ester

To a solution of 5 g 3-Formyl-1H-indazole-5-carboxylic acid methyl ester in 100 mL acetonitrile and 8 mL DMF a solution of 4.4 g NaH$_2$PO$_4$ in 90 mL water was added dropwise at RT within 1 h. Then a solution of 4.2 g NaClO$_2$ (80%) in 90 mL water followed by 5.3 mL H$_2$O$_2$ (30%) was added dropwise at 0° C. After stirring for 16 h at RT the reaction mixture was cooled to 0° C. followed by addition of 180 mL half-concentrated aqueous hydrochloric acid. The precipitated product was collected by filtration to yield 2.3 g pure product. The filtrate was extracted with ethyl acetate (3×150 mL), the combined organic layers were dried over MgSO$_4$. After removal of the solvent under reduced pressure further 3.42 g of product were obtained. The combined product fractions were used without further purification. Yield: 5.7 g.

(ii) 3-(1-Isopropyl-piperidin-4-ylcarbamoyl)-1H-indazole-5-carboxylic acid methyl ester To a solution of 1 g 1H-Indazole-3,5-dicarboxylic acid 5-methyl ester in 8 mL DCM, 2.5 mL NEt$_3$, 1.15 g BOP-Cl and 0.98 g 1-Isopropyl-piperidin-4-ylamine hydrochloride were added at RT. The mixture was stirred for 3 h. After addition of 20 mL of water the reaction mixture was extracted with DCM (3×50 mL). The combined organic layers were dried over MgSO$_4$. After removal of the solvent under reduced pressure the crude product was used without further purification.

Yield: 1.4 g.

(iii) 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester To a solution of 1.4 g 3-(1-Isopropyl-piperidin-4-ylcarbamoyl)-1H-indazole-5-carboxylic acid methyl ester in 10 mL DMF, 1.42 g Cs$_2$CO$_3$ and 1.21 g Bromomethyl-5-(5-chloro-thiophen-2-yl)-isoxazole were added at RT and the reaction mixture was stirred for 2 h. After addition of 10 mL water the mixture was extracted with DCM (3×50 mL), the combined organic layers were dried over MgSO$_4$ and filtered. Then the solvents were removed under reduced pressure and the residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.

Yield: 2.1 g MS (ES$^+$): m/e=542, chloro pattern.

Example 2

1-[5-(5-Chloro-thiophen-2-yl)-isoxazol-3-ylmethyl]-3-(1-isopropyl-piperidin-4-ylcarbamoyl)-1H-indazole-6-carboxylic acid methyl ester The title compound was prepared analogously to example 1 with the difference that 1H-Indole-6-carboxylic acid methyl ester was used instead of 1H-Indole-5-carboxylic acid methyl ester.

MS (ES$^+$): m/e=542, chloro pattern.

Example 3

1-[5-(5-Chloro-thiophen-2-yl)-isoxazol-3-ylmethyl]-3-(1-isopropyl-piperidin-4-ylcarbamoyl)-1H-indazole-7-carboxylic acid methyl ester The title compound was prepared analogously to example 1 with the difference that 1H-Indole-7-carboxylic acid methyl ester was used instead of 1H-Indole-5-carboxylic acid methyl ester.

MS (ES$^+$): m/e=542, chloro pattern.

Example 4

1-[5-(5-Chloro-thiophen-2-yl)-isoxazol-3-ylmethyl]-3-(1-isopropyl-piperidin-4-ylcarbamoyl)-1H-indazole-5-carboxylic acid To a solution of 85 mg 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester in 4 mL THF/water 2:1, 0.8 mL aqueous NaOH (1M) were added at RT and the reaction mixture was stirred for 16 h. Then, 2 mL half concentrated hydrochloric acid were added and the mixture was evaporated and lyophilized. The solid residue was stirred with 50 mL DCM and remaining inorganic salts were filtered off. After evaporation of the solvent the product was obtained as its hydrochloride.

Yield: 87 mg MS (ES$^+$): m/e=528, chloro pattern.

Example 5

1-[5-(5-Chloro-thiophen-2-yl)-isoxazol-3-ylmethyl]-3-(1-isopropyl-piperidin-4-ylcarbamoyl)-1H-indazole-7-carboxylic acid The title compound was prepared analogously to example 4 with the difference that 1-[5-(5-Chloro-thiophen-2-yl)-isoxazol-3-ylmethyl]-3-(1-isopropyl-piperidin-4-ylcarbamoyl)-1H-indazole-7-carboxylic acid methyl ester was used instead of 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester. MS (ES$^+$): m/e=528, chloro pattern.

Example 6

1-[5-(5-Chloro-thiophen-2-yl)-isoxazol-3-ylmethyl]-3-(1-isopropyl-piperidin-4-ylcarbamoyl)-1H-indazole-6-carboxylic acid The title compound was prepared analogously to example 4 with the difference that 1-[5-(5-Chloro-thiophen-2-yl)-isoxazol-3-ylmethyl]-3-(1-isopropyl-piperidin-4-ylcarbamoyl)-1H-indazole-6-carboxylic acid methyl ester was used instead of 1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester. MS (ES$^+$): m/e=528, chloro pattern.

Example 7

Indazole-1,3-dicarboxylic acid 1-[(5-chloro-pyridin-2-yl)-amide]3-[(1-isopropyl-piperidin-4-yl)-amide]

(i) 1H-Indazole-3-carboxylic acid (1-isopropyl-piperidin-4-yl)-amide

To a solution of 300 mg 1H-Indazole-3-carboxylic acid in 3 mL DMF and 1 mL NEt$_3$, 398 mg 1-Isopropyl-piperidin-4-ylamine hydrochloride and 471 mg BOP-Cl were added at RT and the mixture was stirred for 16 h. After the addition of 5 mL water the mixture was filtered through a chem elut® cartridge by elution with ethyl acetate and then concentrated under reduced pressure. The residue was directly subjected to the subsequent alkylation reaction without further purification. Yield: 340 mg.

(ii) 2-Bromo-N-(5-chloro-pyridin-2-yl)-acetamide

To a solution of 5 g 5-Chloro-pyridin-2-ylamine and 1.5 mL pyridine in 30 mL toluene 8 g bromo-acetyl bromide dissolved in 10 mL toluene was added dropwise under ice cooling. After 2 h the precipitate was isolated by filtration and recristallized from toluene to yield a white solid.

Yield: 12 g.

(iii) Indazole-1,3-dicarboxylic acid 1-[(5-chloro-pyridin-2-yl)-amide]3-[(1-isopropyl-piperidin-4-yl)-amide]

To a solution of 180 mg 1H-Indazole-3-carboxylic acid (1-isopropyl-piperidin-4-yl)-amide in 2 mL DMF, 25 mg NaH (60% in oil) were added at RT and stirred for 10 min. Then, 157 mg 2-Bromo-N-(5-chloro-pyridin-2-yl)-acetamide were added and the reaction mixture was allowed to stir for 2 h. After the addition of 2 mL sat. NaHCO$_3$ the mixture was filtered through a chem elut® cartridge by elution with ethyl acetate and then concentrated under reduced pressure. The residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt.

Yield: 130 mg MS (ES$^+$): m/e=455, chloro pattern.

Example 8

1-[5-(5-Chloro-thiophen-2-yl)-isoxazol-3-ylmethyl]-1H-indazole-3-carboxylic acid (1-isopropyl-piperidin-4-yl)-amide The title compound was prepared analogously to example 7 with the difference that 3-Bromomethyl-5-(5-chloro-thiophen-2-yl)-isoxazole was used instead of 2-Bromo-N-(5-chloro-pyridin-2-yl)-acetamide. MS (ES$^+$): m/e=484, chloro pattern.

Example 9

1-[5-(5-Chloro-thiophen-2-yl)-isoxazol-3-ylmethyl]-3-(1-isopropyl-piperidin-4-ylcarbamoyl)-1H-indazole-5-carboxylic acid 1-ethoxycarbonyloxy-ethyl ester To a solution of 0.5 g 1-[5-(5-Chloro-thiophen-2-yl)-isoxazol-3-ylmethyl]-3-(1-isopropyl-piperidin-4-ylcarbamoyl)-1H-indazole-5-carboxylic acid acetate (see example 4) and 0.529 g 1-chloroethyl-ethylcarbonate in 20 mL DMF 0.47 g $K_2CO_3$ and 0.282 g KI were added and the reaction mixture was stirred for 4 h at 60° C. in an argon atmosphere. After filtration and removal of the solvent under reduced pressure the residue was directly purified by preparative RP-HPLC eluting with a gradient of 0-100% acetonitrile in water (+0.01% trifluoroacetic acid). After addition of 1 M hydrochloric acid and lyophilization in an acetonitrile/water mixture, the product was obtained as its hydrochloride.

Yield: 0.406 g MS (ESI+): m/e=644, chloro pattern.

Example 10

1-[5-(5-Chloro-thiophen-2-yl)-isoxazol-3-ylmethyl]-4-cyano-1H-indazole-3-carboxylic acid (1-isopropyl-piperidin-4-yl)-amide (i) 3-Formyl-1H-indazole-4-carbonitrile The title compound was prepared analogously to example 1 (i) with the difference that 1H-Indole-4-carbonitrile was used instead of 1H-Indole-5-carboxylic acid methyl ester.

MS (ES+): m/e=171.

(ii) 1-[5-(5-Chloro-thiophen-2-yl)-isoxazol-3-ylmethyl]-3-formyl-1H-indazole-4-carbonitrile The title compound was prepared analogously to example 1 (ii) with the difference that 3-Formyl-1H-indazole-4-carbonitrile was used instead of 3-Formyl-1H-indazole-5-carboxylic acid methyl ester.

MS (ES+): m/e=368, chloro pattern.

(iii) 1-[5-(5-Chloro-thiophen-2-yl)-isoxazol-3-ylmethyl]-4-cyano-1H-indazole-3-carboxylic acid The title compound was prepared analogously to example 1 (iii) with the difference that 1-[5-(5-Chloro-thiophen-2-yl)-isoxazol-3-ylmethyl]-3-formyl-1H-indazole-4-carbonitrile was used instead of 1-[5-(5-Chloro-thiophen-2-yl)-isoxazol-3-ylmethyl]-3-formyl-1H-indazole-5-carboxylic acid methyl ester and that a modified oxidation procedure described by E. Dalacanale et al. J. Org. Chem. (1986) 51, 567 employing $H_2O_2$ instead of 2-methylbutene was utilized.

MS (ES+): m/e=385, chloro pattern.

(iv) 1-[5-(5-Chloro-thiophen-2-yl)-isoxazol-3-ylmethyl]-4-cyano-1H-indazole-3-carboxylic acid (1-isopropyl-piperidin-4-yl)-amide The title compound was prepared analogously to example 1 (iv) with the difference that 1-[5-(5-Chloro-thiophen-2-yl)-isoxazol-3-ylmethyl]-4-cyano-1H-indazole-3-carboxylic acid was used instead of 1-[5-(5-Chloro-thiophen-2-yl)-isoxazol-3-ylmethyl]-1H-indazole-3,5-dicarboxylic acid 5-methyl ester. MS (ES+): m/e=509, chloro pattern.

Example 11

1-[5-(5-Chloro-thiophen-2-yl)-isoxazol-3-ylmethyl]-4-(5-oxo-4,5-dihydro-[1,2,4]oxadiazol-3-yl)-1H-indazole-3-carboxylic acid (1-isopropyl-piperidin-4-yl)-amide (i) 1-[5-(5-Chloro-thiophen-2-yl)-isoxazol-3-ylmethyl]-4-(N-hydroxycarbamimidoyl)-1H-indazole-3-carboxylic acid (1-isopropyl-piperidin-4-yl)-amide To a solution of 200 mg 1-[5-(5-Chloro-thiophen-2-yl)-isoxazol-3-ylmethyl]-4-cyano-1H-indazole-3-carboxylic acid (1-isopropyl-piperidin-4-yl)-amide in 3 mL methanol, 27 mg $NH_2OH*HCl$ and 44 mg KOt-Bu were added and the mixture was heated to 50° C. for 3 d. After cooling to RT the precipitated inorganic salts were filtered off. The precipitate was washed with methanol (2×5 ml) and the combined filtrates were collected and concentrated under reduced pressure. The residue was subjected to the next reaction step without further purification. Yield: 223 mg.

(ii) 1-[5-(5-Chloro-thiophen-2-yl)-isoxazol-3-ylmethyl]-4-(5-oxo4,5-dihydro-[1,2,4]oxadiazol-3-yl)-1H-indazole-3-carboxylic acid (1-isopropyl-piperidin-4-yl)-amide To a solution of 223 mg 1-[5-(5-Chloro-thiophen-2-yl)-isoxazol-3-ylmethyl]-4-(N-hydroxycarbamimidoyl)-1H-indazole-3-carboxylic acid (1-isopropyl-piperidin-4-yl)-amide in 2 mL DMF, 35 µl pyridine and i-butylchlorformiate were added at 0° C. Then the reaction mixture was warmed to RT and stirred for 1 h. After the addition of 2 mL of water the mixture was filtered through a chem elut® cartridge by elution with ethyl acetate and then concentrated under reduced pressure. The residue was taken-up in 4 mL xylene and heated to reflux for 3 d. After cooling the reaction mixture, the solvents were removed under reduced pressure. The residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 20.6 mg MS (ES+): m/e=568, chloro pattern.

Example 12

5-(Azetidine-1-carbonyl)-1-[5-(5-chloro-thiophen-2-yl)-isoxazol-3-ylmethyl]-1H-indazole-3-carboxylic acid (1-isopropyl-piperidin-4-yl)-amide To a solution of 50 mg 1-[5-(5-Chloro-thiophen-2-yl)-isoxazol-3-ylmethyl]-3-(1-isopropyl-piperidin-4-ylcarbamoyl)-1H-indazole-5-carboxylic acid in 1 mL DCM 186 mg TOTU and 130 mg NEM were added at RT followed by 8.1 mg azetidine. After stirring for 16 h the reaction mixture was concentrated under reduced pressure and the residue directly purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 14 mg MS (ES+): m/e=567, chloro pattern.

Example 13

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-methanesulfonyl-ethyl)-amide]

The title compound was prepared analogously to example 12 with the difference that 2-Methanesulfonyl-ethylamine was used instead of azetidine.

MS (ES$^+$): m/e=633, chloro pattern.

Example 14

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-sulfamoyl-ethyl)-amide]

The title compound was prepared analogously to example 12 with the difference that 2-Amino-ethanesulfonic acid amide hydrochloride was used instead of azetidine.

MS (ES$^+$): m/e=634, chloro pattern.

Example 15

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-morpholin-4-yl-ethyl)-amide]

The title compound was prepared analogously to example 12 with the difference that 2-Morpholin-4-yl-ethylamine was used instead of azetidine. MS (ES$^+$): m/e=640, chloro pattern.

Example 16

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-trimethylsilanylmethyl-amide The title compound was prepared analogously to example 12 with the difference that C-Trimethylsilanyl-methylamine was used instead of azetidine.

MS (ES$^+$): m/e=613, chloro pattern.

Example 17

1-[5-(5-Chloro-thiophen-2-yl)-isoxazol-3-ylmethyl]-1H-indazole-3,5-dicarboxylic acid 5-[bis-(2-hydroxy-ethyl)-amide]3-[(1-isopropyl-piperidin-4-yl)-amide]

The title compound was prepared analogously to example 12 with the difference that 2-(2-Hydroxy-ethylamino)-ethanol was used instead of azetidine.

MS (ES$^+$): m/e=615, chloro pattern.

Example 18

1-[5-(5-Chloro-thiophen-2-yl)-isoxazol-3-ylmethyl]-1H-indazole-3,5-dicarboxylic acid 5-[(2-hydroxy-ethyl)-methyl-amide]3-[(1-isopropyl-piperidin-4-yl)-amide]

The title compound was prepared analogously to example 12 with the difference that 2-Methylamino-ethanol was used instead of azetidine. MS (ES$^+$): m/e=585, chloro pattern.

Example 19

{[1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid ethyl ester The title compound was prepared analogously to example 12 with the difference that Amino-acetic acid ethyl ester was used instead of azetidine. MS (ES$^+$): m/e=613, chloro pattern.

Example 20

1-[5-(5-Chloro-thiophen-2-yl)-isoxazol-3-ylmethyl]-1H-indazole-3,5-dicarboxylic acid 5-[(2,2-difluoro-ethyl)-amide]3-[(1-isopropyl-piperidin-4-yl)-amide]

The title compound was prepared analogously to example 12 with the difference that 2,2-Difluoro-ethylamine was used instead of azetidine. MS (ES$^+$): m/e=591, chloro pattern.

Example 21

1-[5-(5-Chloro-thiophen-2-yl)-isoxazol-3-ylmethyl]-1H-indazole-3,5-dicarboxylic acid 5-carbamoylmethyl-amide 3-[(1-isopropyl-piperidin-4-yl)-amide]

The title compound was prepared analogously to example 12 with the difference that 2-Amino-acetamide was used instead of azetidine. MS (ES$^+$): m/e=584, chloro pattern.

Example 22

1-[5-(5-Chloro-thiophen-2-yl)-isoxazol-3-ylmethyl]-1H-indazole-3,5-dicarboxylic acid 5-[(2-hydroxy-ethyl)-amide]3-[(1-isopropyl-piperidin-4-yl)-amide]

The title compound was prepared analogously to example 12 with the difference that 2-Amino-ethanol was used instead of azetidine. MS (ES$^+$): m/e=571, chloro pattern.

Example 23

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-{[2-(2-oxo-imidazolidin-1-yl)-ethyl]-amide}

The title compound was prepared analogously to example 12 with the difference that 1-(2-Amino-ethyl)-imidazolidin-2-one was used instead of azetidine.

MS (ES$^+$): m/e=639, chloro pattern.

Example 24

1-[5-(5-Chloro-thiophen-2-yl)-isoxazol-3-ylmethyl]-1H-indazole-3,5-dicarboxylic acid 5-[(2-hydroxy-1-hydroxymethyl-1-methyl-ethyl)-amide]3-[(1-isopropyl-piperidin-4-yl)-amide]

The title compound was prepared analogously to example 12 with the difference that 2-Amino-2-methyl-propane-1,3-diol was used instead of azetidine. MS (ES$^+$): m/e=615, chloro pattern.

Example 25

{[1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid The title compound was prepared analogously to example 12 with the difference that Amino-acetic acid was used instead of azetidine. MS (ES$^+$): m/e=585, chloro pattern.

Example 26

1-[1-[5-(5-Chloro-thiophen-2-yl)-isoxazol-3-ylmethyl]-3-(1-isopropyl-piperidin-4-ylcarbamoyl)-1H-indazole-5-carbonyl]-(2S)-azetidine-2-carboxylic acid The title compound was prepared analogously to example 12 with the difference that (2S)-Azetidine-2-carboxylic acid was used instead of azetidine. MS (ES$^+$): m/e=611, chloro pattern.

Example 27

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2,2,2-trifluoro-ethyl)-amide]

The title compound was prepared analogously to example 12 with the difference that 2,2,2-Trifluoro-ethylamine was used instead of azetidine. MS (ES$^+$): m/e=609, chloro pattern.

Example 28

{[1-[5-(5-Chloro-thiophen-2-yl)-isoxazol-3-ylmethyl]-3-(1-isopropyl-piperidin-4-ylcarbamoyl)-1H-indazole-5-carbonyl]-methyl-amino}-acetic acid The title compound was prepared analogously to example 12 with the difference that Methylamino-acetic acid was used instead of azetidine. MS (ES$^+$): m/e=599, chloro pattern.

Example 29

1-[5-(5-Chloro-thiophen-2-yl)-isoxazol-3-ylmethyl]-3-(1-isopropyl-piperidin-4-ylcarbamoyl)-1H-indazole-5-carboxylic acid 2-hydroxy-ethyl ester The title compound was prepared analogously to example 12 with the difference that Ethane-1,2-diol was used instead of azetidine. MS (ES$^+$): m/e=572, chloro pattern.

Example 30

1-[5-(5-Chloro-thiophen-2-yl)-isoxazol-3-ylmethyl]-5-([1,4]oxazepane-4-carbonyl)-1H-indazole-3-carboxylic acid (1-isopropyl-piperidin-4-yl)-amide The title compound was prepared analogously to example 12 with the difference that [1,4]Oxazepane was used instead of azetidine. MS (ES$^+$): m/e=611, chloro pattern.

Example 31

1-[5-(5-Chloro-thiophen-2-yl)-isoxazol-3-ylmethyl]-5-(3-hydroxy-azetidine-4-carbonyl)-1H-indazole-3-carboxylic acid (1-isopropyl-piperidin-4-yl)-amide The title compound was prepared analogously to example 12 with the difference that Azetidin-3-ol hydrochloride was used instead of azetidine. MS (ES$^+$): m/e=583, chloro pattern.

Example 32

1-[5-(5-Chloro-thiophen-2-yl)-isoxazol-3-ylmethyl]-1H-indazole-3,5-dicarboxylic acid 3-[(1-isopropyl-piperidin-4-yl)-amide]5-(methoxy-amide)

The title compound was prepared analogously to example 12 with the difference that O-Methyl-hydroxylamine was used instead of azetidine. MS (ES$^+$): m/e=557, chloro pattern.

Example 33

1-[(5-Chloro-pyridin-2-ylcarbamoyl)-methyl]-1H-indazole-3-carboxylic acid [4-(piperidine-1-carbonyl)-phenyl]-amide (i) (4-Amino-phenyl)-piperidin-1-yl-methanone
To a solution of 100 mg 4-Amino-benzoic acid in 1 mL DCM and 0.2 mL NEt$_3$, 62 mg piperidine and 184 mg BOP-Cl were added at RT and the mixture was stirred for 16 h. After the addition of 5 mL water the mixture was filtered through a chem elut® cartridge by elution with ethyl acetate and then concentrated under reduced pressure. The residue was directly subjected to the subsequent amide coupling reaction without further purification. Yield: 125 mg.

(ii) 1H-Indazole-3-carboxylic acid [4-(piperidine-1-carbonyl)-phenyl]-amide
To a solution of 100 mg 1H-indazole-3-carboxylic acid in 2 mL DCM and 0.3 mL NEt$_3$, 125 mg (4-Amino-phenyl)-piperidin-1-yl-methanone and 157 mg BOP-Cl were added at RT and the mixture was stirred for 16 h. After the addition of 5 mL water the mixture was filtered through a chem elut® cartridge by elution with ethyl acetate and then concentrated under reduced pressure. The residue was directly subjected to the subsequent alkylation reaction without further purification.
Yield: 112 mg.

(iii) 1-[(5-Chloro-pyridin-2-ylcarbamoyl)-methyl]-1H-indazole-3-carboxylic acid [4-(piperidine-1-carbonyl)-phenyl]-amide
To a solution of 50 mg 1H-Indazole-3-carboxylic acid [4-(piperidine-l-carbonyl)-phenyl]-amide in 1 mL DMF, 46 mg Cs$_2$CO$_3$ and 36 mg 2-Bromo-N-(5-chloro-pyridin-2-yl)- acetamide were added at RT and the reaction mixture was stirred for 16 h. After addition of 5 mL water the mixture was filtered through a chem elut® cartridge by elution with ethyl acetate and and then concentrated under reduced pressure. The residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt. Yield: 111 mg MS (ES$^+$): m/e=517, chloro pattern.

Example 34

1-[5-(5-Chloro-thiophen-2-yl)-isoxazol-3-ylmethyl]-1H-indazole-3-carboxylic acid [4-(pyrrolidine-1-carbonyl)-phenyl]-amide The title compound was prepared analogously to example 33 with the difference that pyrrolidine and Bromomethyl-5-(5-chloro-thiophen-2-yl)-isoxazole was used instead of piperidine and 2-Bromo-N-(5-chloro-pyridin-2-yl)-acetamide. MS (ES$^+$): m/e=532, chloro pattern.

Example 35

1-[5-(5-Chloro-thiophen-2-yl)-isoxazol-3-ylmethyl]-1H-indazole-3-carboxylic acid [4-(morpholine-4-carbonyl)-phenyl]-amide The title compound was prepared analogously to example 33 with the difference that morpholine and Bromomethyl-5-(5-chloro-thiophen-2-yl)-isoxazole was used instead of piperidine and 2-Bromo-N-(5-chloro-pyridin-2-yl)-acetamide.

MS (ES$^+$): m/e=548, chloro pattern.

Example 36

1-[(5-Chloro-pyridin-2-ylcarbamoyl)-methyl]-1H-indazole-3-carboxylic acid [4-(morpholine-4-carbonyl)-phenyl]-amide The title compound was prepared analogously to example 33 with the difference that morpholine was used instead of piperidine. MS (ES$^+$): m/e=519, chloro pattern.

Example 37

1-(1-{1-[5-(5-Chloro-thiophen-2-yl)-isoxazol-3-ylmethyl]-1H-indazole-3-carbonyl}-piperidin-4-yl)-pyrrolidin-2-one The title compound was prepared analogously to example 33 with the difference that 1-Piperidin-4-yl-pyrrolidin-2-one and and Bromomethyl-5-(5-chloro-thiophen-2-yl)-isoxazole was used instead of (4-Amino-phenyl)-piperidin-1-yl-methanone and 2-Bromo-N-(5-chloro-pyridin-2-yl)-acetamide. MS (ES$^+$): m/e=510, chloro pattern.

Example 38

N-(5-Chloro-pyridin-2-yl)-2-{3-[4-(2-oxo-pyrrolidin-1-yl)-piperidine-1-carbonyl]-indazol-1-yl}-acetamide The title compound was prepared analogously to example 33 with the difference that 1-Piperidin-4-yl-pyrrolidin-2-one and was used instead of (4-Amino-phenyl)-piperidin-1-yl-methanone. MS (ES$^+$): m/e=481, chloro pattern.

Example 39

1-[5-(5-Chloro-thiophen-2-yl)-isoxazol-3-ylmethyl]-1H-indazole-3-carboxylic acid [4-(2-oxo-pyrrolidin-1-yl)-phenyl]-amide (i) 1-(4-Amino-phenyl)-pyrrolidin-2-one 800 mg Benzene-1,4-diamine and 600 µl Dihydro-furan-2-one were heated for 1 h to 200° C. under microwave irradiation (200 W, CEM Discover™ apparatus). Finally, 10 mL saturated $NaHCO_3$ solution were added and the mixture was directly purified by chromatography on silica gel eluting with a gradient of DCM/MeOH 100%->50%. The fractions containing the product were combined and the solvent evaporated under reduced pressure. Yield: 860 mg.

(ii) 1H-Indazole-3-carboxylic acid [4-(2-oxo-pyrrolidin-1-yl)-phenyl]-amide

To a solution of 50 mg 1H-Indazole-3-carboxylic acid in 2 mL DCM and 0.2 mL $NEt_3$, 108 mg 1-(4-Amino-phenyl)-pyrrolidin-2-one and 79 mg BOP-Cl were added at RT and the mixture was stirred for 16 h. After the addition of 5 mL water the mixture was filtered through a chem elut® cartridge by elution with ethyl acetate and then concentrated under reduced pressure. The residue was directly subjected to the subsequent alkylation reaction without further purification.

Yield: 140 mg.

(iii) 1-[5-(5-Chloro-thiophen-2-yl)-isoxazol-3-ylmethyl]-1H-indazole-3-carboxylic acid [4-(2-oxo-pyrrolidin-1-yl)-phenyl]-amide To a solution of 70 mg 1H-Indazole-3-carboxylic acid [4-(2-oxo-pyrrolidin-1-yl)-phenyl]-amide in 1 mL DMF, 9 mg NaH (60% in oil) were added at RT and stirred for 10 min. Then, 61 mg Bromomethyl-5-(5-chloro-thiophen-2-yl)-isoxazole were added and the reaction mixture was allowed to stir for 2 h. After the addition of 2 mL sat. $NaHCO_3$ the mixture was filtered through a chem elut® cartridge by elution with ethyl acetate and then concentrated under reduced pressure. The residue was purified by preparative HPLC (C18 reverse phase column, elution with a $H_2O$/MeCN gradient with 0.1% TFA). The fractions containing the product were evaporated and lyophilized to yield a white solid. The product was obtained as its trifluoroacetate salt.

Yield: 3 mg MS (ES$^+$): m/e=518, chloro pattern.

Example 40

1-[(5-Chloro-pyridin-2-ylcarbamoyl)-methyl]-1H-indazole-3-carboxylic acid [4-(2-oxo-pyrrolidin-1-yl)-phenyl]-amide The title compound was prepared analogously to example 39 with the difference that 2-Bromo-N-(5-chloro-pyridin-2- yl)-acetamide was used instead of Bromomethyl-5-(5-chloro-thiophen-2-yl)-isoxazole. MS (ES$^+$): m/e=489, chloro pattern.

Example 41

1-[5-(5-Chloro-thiophen-2-yl)-isoxazol-3-ylmethyl]-1H-indazole-3-carboxylic acid (2'-methanesulfonyl-biphenyl-4-yl)-amide The title compound was prepared analogously to example 39 with the difference that 1-2'-Methanesulfonyl-biphenyl-4-ylamine [prepared by adopting a procedure from Juraszyk, Horst; Dorsch, Dieter; Mederski, Werner; Tsaklakidis, Christos; Barnes, Christopher; Gleitz, Johannes; PCT Int. Appl. (2001), 37 pp, WO 0170678 A2] was used instead of 1-(4-Amino-phenyl)-pyrrolidin-2-one. MS (ES$^+$): m/e=589, chloro pattern.

Example 42

1-[(5-Chloro-pyridin-2-ylcarbamoyl)-methyl]-1H-indazole-3-carboxylic acid (2'-methanesulfonyl-biphenyl-4-yl)-amide The title compound was prepared analogously to example 39 with the difference that 1-2'-Methanesulfonyl-biphenyl-4-ylamine [prepared by adopting a procedure from Juraszyk, Horst; Dorsch, Dieter; Mederski, Werner; Tsaklakidis, Christos; Barnes, Christopher; Gleitz, Johannes PCT Int. Appl. (2001), 37 pp, WO 0170678 A2] and Bromo-N-(5-chloro-pyridin-2-yl)-acetamide was used instead of 1-(4-Amino-phenyl)-pyrrolidin-2-one and Bromomethyl-5-(5-chloro-thiophen-2-yl)-isoxazole. MS (ES$^+$): m/e=560, chloro pattern.

Example 43

1-[5-(5-Chloro-thiophen-2-yl)-isoxazol-3-ylmethyl]-1H-indazole-3-carboxylic acid [4-(4-methyl-6-oxo-1,4,5,6-tetrahydro-pyridazin-3-yl)-phenyl]-amide The title compound was prepared analogously to example 8 with the difference that 6-(4-Amino-phenyl)-5-methyl-4,5-dihydro-2H-pyridazin-3-one was used instead of 1-Isopropyl-piperidin-4-ylamine hydrochloride. MS (ES$^+$): m/e=545, chloro pattern.

Example 44

1-[5-(5-Chloro-thiophen-2-yl)-isoxazol-3-ylmethyl]-1H-indazole-3-carboxylic acid (4-morpholin-4-yl-phenyl)-amide The title compound was prepared analogously to example 8 with the difference that 4-Morpholin-4-yl-phenylamine was used instead of 1-Isopropyl-piperidin-4-ylamine hydrochloride.

MS (ES$^+$): m/e=520, chloro pattern.

Example 45

1-[5-(5-Chloro-thiophen-2-yl)-isoxazol-3-ylmethyl]-1H-indazole-3-carboxylic acid [4-(1H-imidazol-4-yl)-phenyl]-amide The title compound was prepared analogously to example 8 with the difference that 4-(1H-Imidazol-4-yl)-phenylamine was used instead of 1-Isopropyl-piperidin-4-ylamine hydrochloride.

MS (ES$^+$): m/e=501, chloro pattern.

Example 46

1-[5-(5-Chloro-thiophen-2-yl)-isoxazol-3-ylmethyl]-1H-indazole-3-carboxylic acid (4-piperidin-1-yl-phenyl)-amide The title compound was prepared analogously to example 8 with the difference that 4-Piperidin-1-yl-phenylamine was used instead of 1-Isopropyl-piperidin-4-ylamine hydrochloride.

MS (ES$^+$): m/e=518, chloro pattern.

Example 47

1-[5-(5-Chloro-thiophen-2-yl)-isoxazol-3-ylmethyl]-3-[4-(3-oxo-morpholin-4-yl)-phenylcarbamoyl]-1H-indazole-5-carboxylic acid methyl ester (i) 4-(4-Nitro-phenyl)-morpholine A mixture of 24.5 g morpholine and 13.3 g 1-Fluoro-4-nitro-benzene in 30 mL DMSO was heated to 100° C. This solution was poured on to 300 mL of water and the resulting precipitate was collected by filtration to yield a bright yellow crystalline product, which was dried in vacuo.
Yield: 19.7 g (ii) 4-(4-Nitro-phenyl)-morpholin-3-one To a solution of 10 g 4-(4-Nitro-phenyl)-morpholine in 200 mL DCM, 32 g Benzyl-triethyl-ammonium chloride and 22.7 g potassium permanganate (325 mesh) were cautiously added at RT. After stirring for 1 h the reaction mixture was heated to reflux for 10 h. Then, a solution of 95 g Na$_2$SO$_3$ in 450 mL water was added under ice cooling and vigorous stirring. The mixture was filtered through a pad of celite and the filtrate was concentrated under reduced pressure. The yellow solid was stirred with 250 mL water and the precipitated product was collected by filtration. This crude product was purified by chromatography on silica gel eluting with a gradient of DCM/MeOH 100%->50%. The fractions containing the product were combined and the solvent evaporated under reduced pressure. Yield: 2.6 g.

(iii) 4-(4-Amino-phenyl)-morpholin-3-one

To a solution of 2.6 g 4-(4-Nitro-phenyl)-morpholin-3-one in 350 mL ethyl acetate and 17 mL ethanol 13.2 g SnCl$_2$ dihydrate were added and the reaction mixture was heated to reflux for 2 h. Then after cooling to RT the mixture was stirred for 16 h. The precipitated product was collected by filtration and was pure enough for the next reaction step.
Yield: 2.07 g.

(iv) 3-[4-(3-Oxo-morpholin-4-yl)-phenylcarbamoyl]-1H-indazole-5-carboxylic acid methyl ester To a solution of 60 mg 1H-Indazole-3,5-dicarboxylic acid 5-methyl ester and 52 mg 4-(4-Amino-phenyl)-morpholin-3-one in 2 mL DCM, 68 mg BOP-Cl and 0.15 mL NEt$_3$ were added and the mixture was stirred for 16 h at RT. Then after the reaction mixture was diluted with 20 mL DCM, the solution was washed with 15 mL of water. The organic phase was dried over MgSO$_4$ and after filtration concentrated under reduced pressure. The crude product was subjected to the next reaction step without further purification. Yield: 71 mg.

(V) 1-[5-(5-Chloro-thiophen-2-yl)-isoxazol-3-ylmethyl]-3-[4-(3-oxo-morpholin-4-yl)-phenylcarbamoyl]-1H-indazole-5-carboxylic acid methyl ester To a solution of 71 mg 3-[4-(3-Oxo-morpholin-4-yl)-phenylcarbamoyl]-1H-indazole-5-carboxylic acid methyl ester in 1.5 mL DMF, 59 mg Cs$_2$CO$_3$ and 50 mg Bromomethyl-5-(5-chloro-thiophen-2-yl)-isoxazole were added at RT and the reaction mixture was stirred for 16 h. After filtration the solvents were removed under reduced pressure and residue was purified by preparative HPLC (C18 reverse phase column, elution with a H$_2$O/MeCN gradient with 0.1% TFA). The fractions containing the product were evaporated and lyophilized to yield a white solid. The product was obtained as its trifluoroacetate salt. Yield: 7.9 mg MS (ES$^+$): m/e=592, chloro pattern.

Example 48

1-[(5-Chloro-pyridin-2-ylcarbamoyl)-methyl]-3-(1-isopropyl-piperidin-4-ylcarbamoyl)-1H-indazole-5-carboxylic acid methyl ester To a solution of 4 g 3-(1-Isopropyl-piperidin-4-ylcarbamoyl)-1H-indazole-5-carboxylic acid methyl ester in 35 mL DMF, 3.8 g Cs$_2$CO$_3$ and 2.9 g 2-Bromo-N-(5-chloro-pyridin-2-yl)-acetamide were added at RT and the reaction mixture was stirred for 2 d. After addition of 50 mL water the mixture was extracted with ethyl acetate (3×150 mL), the combined organic layers were dried over MgSO$_4$ and filtered. The solvents were removed under reduced pressure and the residue was recrystallized from diisopropylether. Yield: 3.8 g MS (ES$^+$): m/e=513, chloro pattern.

Example 49

1-[(5-Chloro-pyridin-2-ylcarbamoyl)-methyl]-3-(1-isopropyl-piperidin-4-ylcarbamoyl)-1H-indazole-5-carboxylic acid To a solution of 3.5 g 1-[(5-Chloro-pyridin-2-ylcarbamoyl)-methyl]-3-(1-isopropyl-piperidin-4-ylcarbamoyl)-1H-indazole-5-carboxylic acid methyl ester in 150 mL DCM, 31 mL of a 1M solution of boron tribromide in DCM were added slowly at RT. The reaction mixture was stirred for 16 h. concentration of the solution under reduced pressure led to precipitation of the product which was collected by filtration. The product was obtained as its hydrobromide.
Yield: 4.6 g MS (ES$^+$): m/e=499, chloro pattern.

Example 50

1-[5-(5-Chloro-thiophen-2-yl)-isoxazol-3-ylmethyl]-3-(1-isopropyl-piperidin-4-ylcarbamoyl)-1H-indazole-5-carboxylic acid 5-methyl-2-oxo-[1,3]dioxol-4-ylmethyl ester To a solution of 0.6 g 1-[5-(5-Chloro-thiophen-2-yl)-isoxazol-3-ylmethyl]-3-(1-isopropyl-piperidin-4-ylcarbamoyl)-1H-indazole-5-carboxylic acid acetate and 0.194 g 4-Chloromethyl-5-methyl-[1,3]dioxol-2-one in 30 mL DMF 0.424 g K$_2$CO$_3$ and 0.254 g KI were added and the reaction mixture was stirred for 2 h at 50° C. in an argon atmosphere. After filtration and removal of the solvent under reduced pressure the residue was directly purified by preparative RP-HPLC (two times) eluting with a gradient of 0-100% acetonitrile in water (+0.01% trifluoroacetic acid). After addition of 1 M hydrochloric acid and lyophilization in an acetonitrile/water mixture, the product was obtained as its hydrochloride. Yield: 0.433 g, MS (ESI+): m/e=640, chloro pattern.

Example 51

1-[5-(5-Chloro-thiophen-2-yl)-isoxazol-3-ylmethyl]-5-(cyanamide-1-carbonyl)-1H-indazole-3-carboxylic acid (1-isopropyl-piperidin-4-yl)-amide The title compound was prepared analogously to example 12 with the difference that cyanamide was used instead of azetidine. MS (ES$^+$): m/e=552, chloro pattern.

Example 52

1-[1-[5-(5-Chloro-thiophen-2-yl)-isoxazol-3-ylmethyl]-3-(1-isopropyl-piperidin-4-ylcarbamoyl)-1H-indazole-5-carbonyl]-azetidine-3-carboxylic acid The title compound was prepared analogously to example 12 with the difference that Azetidine-3-carboxylic acid was used instead of azetidine. MS (ES$^+$): m/e=611, chloro pattern.

Example 53

1-[(5-Chloro-pyridin-2-ylcarbamoyl)-methyl]-1H-indazole-3-carboxylic acid [4-(3-oxo-morpholin-4-yl)-phenyl]-amide The title compound was prepared analogously to example 33 with the difference that 4-(4-Amino-phenyl)-morpholin-3-one was used instead of (4-Amino-phenyl)-piperidin-1-yl-methanone. MS (ES$^+$): m/e=505, chloro pattern.

Example 54

1-[5-(5-Chloro-thiophen-2-yl)-isoxazol-3-ylmethyl]-1H-indazole-3-carboxylic acid [4-(4-oxo-4H-pyridin-1-yl)-phenyl]-amide (i) 1-(4-Nitro-phenyl)-1H-pyridin-4-one A mixture of 10.1 g Pyridin-4-ol and 10 g 1-Fluoro-4-nitro-benzene and 46.1 g Cs$_2$CO$_3$ in 30 mL DMF was stirred at RT for 2 h. This solution was poured on to 300 mL of water and the resulting precipitate was collected by filtration to yield a bright yellow crystalline product, which was dried in vacuo. Yield: 11.2 g.

(ii) 1-(4-Amino-phenyl)-1H-pyridin-4-one

To a solution of 10 g 1-(4-Nitro-phenyl)-H-pyridin-4-one in 510 mL ethyl acetate and 26 mL ethanol, 52.1 g SnCl$_2$ dihydrate were added and the reaction mixture was heated to reflux for 6 h. Then, after cooling to RT the solvents were removed under reduced pressure. The residue was taken-up in 100 mL aqueous NaHCO$_3$ solution and 200 mL ethyl acetate were added. The inorganic precipitate was filtered off and the solids were washed with ethyl acetate. After separation of the organic layer, the aqueous layer of the filtrate was extracted with ethyl acetate (2×100 mL) and with DCM (3×150 mL). The combined organic layers were dried over $Na_2SO_4$ and the solvents were removed under reduced pressure. The remaining product was pure enough for the next reaction step.

Yield: 6 g.

(iii) 1-[5-(5-Chloro-thiophen-2-yl)-isoxazol-3-ylmethyl]-1H-indazole-3-carboxylic acid [4-(4-oxo-4H-pyridin-1-yl)-phenyl]-amide The title compound was prepared analogously to example 8 with the difference that 1-(4-Amino-phenyl)-1H-pyridin-4-one was used instead of 1-Isopropyl-piperidin-4-ylamine hydrochloride.

MS (ES+): m/e=528, chloro pattern.

Example 55

1-[(5-Chloro-pyridin-2-ylcarbamoyl)-methyl]-1H-indazole-3-carboxylic acid [4-(4-oxo-4H-pyridin-1-yl)-phenyl]-amide The title compound was prepared analogously to example 33 with the difference that 1-(4-Amino-phenyl)-1H-pyridin-4-one was used instead of (4-Amino-phenyl)-piperidin-1-yl-methanone. MS (ES+): m/e=499, chloro pattern.

Example 56

1-[5-(5-Chloro-thiophen-2-yl)-isoxazol-3-ylmethyl]-3-(1-isopropyl-piperidin-4-ylcarbamoyl)-1H-indazole-5-carboxylic acid 2-methoxy-ethyl ester The title compound was prepared analogously to example 12 with the difference that 2-Methoxy-ethanol was used instead of azetidine. MS (ES+): m/e=587, chloro pattern.

Example 57

1-[(5-Chloro-pyridin-2-ylcarbamoyl)-methyl]-3-(1-isopropyl-piperidin-4-ylcarbamoyl)-1H-indazole-5-carboxylic acid 2-hydroxy-ethyl ester The title compound was prepared analogously to example 29 with the difference that 1-[(5-Chloro-pyridin-2-ylcarbamoyl)-methyl]-3-(1-isopropyl-piperidin-4-ylcarbamoyl)-1H-indazole-5-carboxylic acid was used instead of 1-[5-(5-Chloro-thiophen-2-yl)-isoxazol-3-ylmethyl]-3-(1-isopropyl-piperidin-4-ylcarbamoyl)-1H-indazole-5-carboxylic acid.

MS (ES+): m/e=544, chloro pattern.

Example 58

1-[(5-Chloro-pyridin-2-ylcarbamoyl)-methyl]-5-([1,4]oxazepane-4-carbonyl)-1H-indazole-3-carboxylic acid (1-isopropyl-piperidin-4-yl)-amide The title compound was prepared analogously to example 30 with the difference that 1-[(5-Chloro-pyridin-2-ylcarbamoyl)-methyl]-3-(1-isopropyl-piperidin-4-ylcarbamoyl)-1H-indazole-5-carboxylic acid was used instead of 1-[5-(5-Chloro-thiophen-2-yl)-isoxazol-3-ylmethyl]-3-(1-isopropyl-piperidin-4-ylcarbamoyl)-1H-indazole-5-carboxylic acid.

MS (ES+): m/e=582, chloro pattern.

Pharmacological Testing

The ability of the compounds of the formula I to inhibit factor Xa or factor VIIa or other enzymes like thrombin, plasmin, or trypsin can be assessed by determining the concentration of the compound of the formula I that inhibits enzyme activity by 50%, i.e. the IC50 value, which was related to the inhibition constant Ki. Purified enzymes were used in chromogenic assays. The concentration of inhibitor that causes a 50% decrease in the rate of substrate hydrolysis was determined by linear regression after plotting the relative rates of hydrolysis (compared to the uninhibited control) versus the log of the concentration of the compound of formula I. For calculating the inhibition constant Ki, the IC50 value was corrected for competition with substrate using the formula $$Ki=IC50/\{1+(\text{substrate concentration}/Km)\}$$

wherein Km is the Michaelis-Menten constant (Chen and Prusoff, Biochem. Pharmacol. 22 (1973), 3099-3108; I. H. Segal, Enzyme Kinetics, 1975, John Wiley & Sons, New York, 100-125; which were incorporated herein by reference).

a) Factor Xa Assay

In the assay for determining the inhibition of factor Xa activity TBS-PEG buffer (50 mM Tris-HCl, pH 7.8, 200 mM NaCl, 0.05% (w/v) PEG-8000, 0.02% (w/v) NaN3) was used. The IC50 was determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N(a)-benzyloxycarbonyl-D-Arg-Gly-L-Arg-p-nitroanilide; Kabi Pharmacia, Inc.; Franklin, Ohio) in TBS-PEG. The assay was performed by pre-incubating the compound of formula I plus enzyme for 10 min. Then the assay was initiated by adding substrate to obtain a final volume of 100 µl. The initial velocity of chromogenic substrate hydrolysis was measured by the change in absorbance at 405 nm using a Bio-tek Instruments kinetic plate reader (Ceres UV900HDi) at 25° C. during the linear portion of the time course (usually 1.5 min after addition of substrate). The enzyme concentration was 0.5 nM and substrate concentration was 140 µM.

b) Factor VIIa Assay

The inhibitory activity towards factor VIIa/tissue factor activity was determined using a chromogenic assay essentially as described previously (J. A. Ostrem et al., Biochemistry 37 (1998) 1053-1059 which was incorporated herein by reference). Kinetic assays were conducted at 25° C. in half-area microtiter plates (Costar Corp., Cambridge, Mass.) using a kinetic plate reader (Molecular Devices Spectramax 250). A typical assay consisted of 25 µl human factor VIIa and TF (5 nM and 10 nM, respective final concentration) combined with 40 µl of inhibitor dilutions in 10% DMSO/TBS-G PEG buffer (50 mM Tris, 15 mM NaCl, 5 mM $CaCl_2$, 0.05% PEG 8000, pH 8.15). Following a 15 minutes preincubation period, the assay was initiated by the addition of 35 µl of the chromogenic substrate S-2288 (D-Ile-Pro-Arg-p-nitroanilide, Pharmacia Hepar Inc., 500 µM final concentration). The results (inhibition constants Ki (FXa) for inhibition of factor Xa) are shown in Table 1.

TABLE 1

| Example | Ki(FXa) [nM] |
|---|---|
| 1 | 79 |
| 2 | 35 |
| 3 | 17 |
| 4 | 18 |
| 5 | 285 |
| 6 | 212 |
| 7 | 86 |
| 8 | 6 |
| 9 | 82 |
| 10 | 9 |
| 11 | 7 |
| 12 | 5 |
| 13 | 40 |
| 14 | 28 |
| 15 | 46 |
| 16 | 54 |
| 17 | 30 |
| 18 | 13 |
| 19 | 26 |
| 20 | 47 |
| 21 | 33 |
| 22 | 28 |
| 23 | 33 |
| 24 | 51 |
| 25 | 14 |
| 26 | 17 |
| 27 | 39 |
| 28 | 15 |
| 29 | 39 |
| 30 | 12 |
| 32 | 22 |
| 34 | 120 |
| 35 | 530 |
| 37 | 210 |
| 39 | 19 |
| 41 | 7 |
| 43 | 730 |
| 45 | 180 |
| 47 | 9 |
| 50 | 41 |
| 51 | 5 |
| 52 | 10 |
| 53 | 240 |
| 54 | 52 |
| 56 | 43 |

We claim:

1. A compound of formula I,

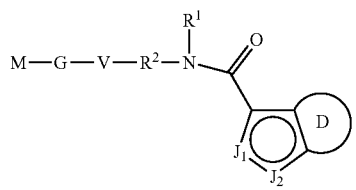

(I)

wherein $J_1$ is N, and $J_2$ is N—Q—$R^0$;
$R^0$ is 5-(5-chloro-thiophen-2-yl)-isoxazol-3-yl;
the substructure

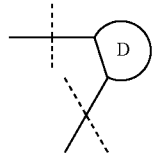

in formula I is
phenyl and is substituted 1, 2, 3 or 4 times by R3;
Q is methylene;
$R^1$ is hydrogen, —($C_1$-$C_4$)-alkyl, wherein the alkyl is unsubstituted or substituted one to three times by R13, —($C_1$-$C_3$)-alkylene-C(O)—NH—$R^0$, —($C_1$-$C_3$)-alkylene-C(O)—O—$R^{15}$, a monocyclic or bicyclic 6- to 14-membered aryl, wherein the aryl is mono-, di- or trisubstituted independently of one another by R8, a monocyclic or bicyclic 4- to 15-membered heterocyclyl, containing one, two, three or four heteroatoms chosen from nitrogen, sulfur or oxygen, —($C_1$-$C_3$)-perfluoroalkylene, —($C_1$-$C_3$)-alkylene-S(O)—($C_1$-$C_4$)-alkyl, —($C_1$-$C_3$)-alkylene-S(O)$_2$—($C_1$-$C_3$)-alkyl, —($C_1$-$C_3$)-alkylene-S(O)$_2$—N($R^{4'}$)—$R^{5'}$, —($C_1$-$C_3$)-alkylene-O—($C_1$-$C_4$)-alkyl, —($C_0$-$C_3$)-alkylene-($C_3$-$C_8$)-cycloalkyl, or —($C_0$-$C_3$)-alkylene-het, wherein the het is a 3- to 7-membered cyclic residue, containing up to 1, 2, 3 or 4 heteroatoms chosen from nitrogen, sulfur or oxygen, wherein said cyclic residue is unsubstituted or mono-, di- or trisubstituted independently of one another by R14;
$R^{4'}$ and $R^{5'}$ are independent of one another are identical or different and are hydrogen or —($C_1$-$C_4$)-alkyl,
$R^2$ is a direct bond or —($C_1$-$C_4$)-alkylene, or
$R^1$ and $R^3$ together with the atoms to which they are bonded form a 6- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14, or
$R^1$—N—$R^2$—V form a 4- to 8-membered cyclic group, containing 1, 2, 3 or 4 heteroatoms chosen from nitrogen, sulfur or oxygen, wherein said cyclic group is unsubstituted or mono-, di- or trisubstituted independently of one another by R14;
R14 is halogen, —OH, =O, —($C_1$-$C_8$)-alkyl, —($C_1$-$C_4$)-alkoxy, —NO$_2$, —C(O)—OH, —CN, —NH$_2$, —C(O)—O—($C_1$-$C_4$)-alkyl, —($C_0$-$C_8$)-alkyl-SO$_2$—($C_1$-$C_4$)-alkyl, —($C_0$-$C_8$)-alkyl-SO$_2$—($C_1$-$C_3$)-perfluoroalkyl, —($C_0$-$C_8$)-alkyl-SO$_2$—N($R^{18}$)—$R^{21}$, —C(O)—NH—($C_1$-$C_8$)-alkyl, —C(O)—N—[($C_1$-$C_8$)-alkyl]$_2$, —NR$^{18}$—C(O)—NH—($C_1$-$C_8$)-alkyl, —C(O)—NH$_2$, —S—$R^{18}$, or —NR$^{18}$—C(O)—NH—[($C_1$-$C_8$)-alkyl]$_2$,
wherein $R^{18}$ and $R^{21}$ are independently from each other hydrogen, —($C_1$-$C_3$)-perfluoroalkyl or —($C_1$-$C_6$)-alkyl;
V is 1) a 3- to 7-membered cyclic residue, containing 1, 2, 3 or 4 heteroatoms chosen from nitrogen, sulfur or oxygen, wherein said cyclic residue is unsubstituted or mono-, di- or trisubstituted independently of one another by R14,
2) a 6- to 14-membered aryl, wherein the aryl is unsubstituted or mono-, di- or trisubstituted independently of one another by R14, or 3) a monocyclic or bicyclic 4- to 15-membered heterocyclyl, wherein the heterocyclyl is unsubstituted or mono-, di- or trisubstituted independently of one another by R14, G is a direct bond, —$(CH_2)_m$—$NR^{10}$—$SO_2$—$NR^{10}$—$(CH_2)_n$—, —$(CH_2)_m$—CH(OH)—$(CH_2)_n$—, —$(CH_2)_m$—, —$(CH_2)_m$—O—$(CH_2)_n$—, —$(CH_2)_m$—C(O)—$NR^{10}$—$(CH_2)_n$—, —$(CH_2)_m$—$SO_2$—$(CH_2)_n$—, —$(CH_2)_m$—$NR^{10}$—C(O)—$NR^{10}$—$(CH_2)_n$—, —$(CH_2)_m$—$NR^{10}$—C(O)—$(CH_2)_n$—, —$(CH_2)_m$—C(O)—$(CH_2)_n$—, —$(CH_2)_m$—S—$(CH_2)_n$—, —$(CH_2)_m$—$SO_2$—$NR^{10}$—$(CH_2)_n$—, —$(CH_2)_m$—$NR^{10}$—$SO_2$—$(CH_2)_n$—, —$(CH_2)_m$—$NR^{10}$—, —$(CH_2)_m$—O—C(O)—$NR^{10}$—$(CH_2)_n$— or —$(CH_2)_m$—$NR^{10}$—C(O)—O—$(CH_2)_n$—;

n and m are independently of one another identical or different and are the integers zero, 1, 2, 3, 4, 5 or 6;

M is 1) hydrogen,
2) —$(C_1-C_8)$-alkyl, wherein the alkyl is unsubstituted or mono-, di- or trisubstituted independently of one another by R14,
3) —C(O)—N(R11)—R12,
4) —$(CH_2)_m$—$NR^{10}$,
5) a 6- to 14-membered aryl, wherein the aryl is unsubstituted or mono-, di- or trisubstituted independently of one another by R14,
6) a monocyclic or bicyclic 4- to 15-membered heterocyclyl, wherein the heterocyclyl is unsubstituted or mono-, di- or trisubstituted independently of one another by R14,
7) —$(C_3-C_8)$-cycloalkyl, wherein the cycloalkyl is unsubstituted or mono-, di- or trisubstituted independently of one another by R14, or
8) a 3- to 7-membered cyclic residue, containing 1, 2, 3 or 4 heteroatoms chosen from nitrogen, sulfur or oxygen, wherein the cyclic residue is unsubstituted or mono-, di- or trisubstituted independently of one another by R14;

R3 is 1) hydrogen,
2) halogen,
3) —$(C_1-C_4)$-alkyl, wherein the alkyl is unsubstituted or mono-, di- or trisubstituted independently of one another by R13,
4) —$(C_1-C_3)$-perfluoroalkyl,
5) phenyl, wherein the phenyl is unsubstituted or mono-, di- or trisubstituted independently of one another by R13,
6) —$(C_0-C_4)$-alkylene-O—R19,
7) —$NO_2$,
8) —CN,
9) —$SO_s$—$R^{11}$, wherein s is 1 or 2,
10) —$SO_t$—N($R^{11}$)—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—N($R^{11}$)—$R^{12}$,
14) —$(C_0-C_4)$-alkylene-N($R^{11}$)—$R^{12}$,
15) —$NR^{10}$—$SO_2$—$R^{10}$,
16) —S—$R^{10}$,
17) —$(C_0-C_2)$alkylene-C(O)—O—$(C_2-C_4)$-alkylene-O—C(O)—$(C_1-C_4)$-alkyl,
18) —C(O)—O—C(R15, R16)—O—C(O)—R17,
19) —$(C_0-C_2)$alkylene-C(O)—O—$(C_2-C_4)$-alkylene-O—C(O)—O—$(C_1-C_6)$-alkyl,
20) —C(O)—O—C(R15, R16)—O—C(O)—O—R17,
21) —$(C_0-C_4)$-alkylene-$(C_6-C_{14})$-aryl, wherein the aryl is mono-, di- or trisubstituted independently of one another by R13,
22) —$(C_0-C_4)$-alkylene-$(C_4-C_{15})$-heterocyclyl, wherein the heterocyclyl is unsubstituted or mono-, di- or trisubstituted independently of one another by R13
23) —$(C_0-C_4)$-alkylene-$(C_3-C_8)$-cycloalkyl, wherein cycloalkyl is unsubstituted or mono-, di- or trisubstituted independently of one another by R13,
24) —$(C_0-C_4)$-alkylene-het, wherein het is unsubstituted or mono-, di- or trisubstituted independently of one another by R13,
25) —$(C_0-C_4)$-alkylene-O—$CH_2$—$(C_1-C_3)$-perfluoroalkylene-$CH_2$—O—$(C_0-C_4)$-alkyl,
26) —$SO_w$—N($R^{11}$)—$R^{13}$, wherein w is 1 or 2,
27) —$(C_0-C_4)$-alkylene-C(O)—N($R^{11}$)—$R^{13}$,
28) —$(C_0-C_4)$-alkylene-N($R^{11}$)—$R^{13}$, or
29) a residue selected from the group consisting of

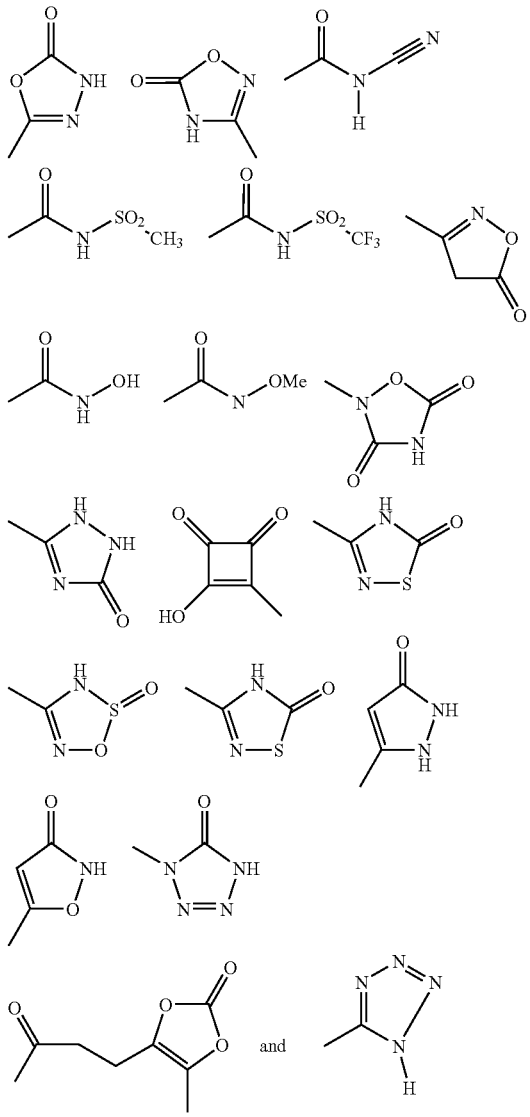

wherein Me is methyl;

R19 is a) hydrogen,
b) —$(C_1-C_4)$-alkyl, wherein alkyl is unsubstituted or mono-, di- or trisubstituted independently of one another by R13, or c) phenyl, wherein the phenyl is unsubstituted or mono-, di- or trisubstituted independently of one another by R13, d) —CF$_3$, or e) —CHF$_2$, or two —OR19 residues and adjacent atoms through which they are attached form together with the atoms which they are attached to a 5- or 6-membered ring, which is unsubstituted or substituted one, two, three or four times by R13;

R11 and R12 are independently of one another identical or different and are 1) hydrogen, 2) —(C$_1$-C$_6$)-alkyl, wherein the alkyl is unsubstituted or mono-, di- or trisubstituted independently of one another by R13, 3) —(C$_0$-C$_6$)-alkyl-(C$_3$-C$_8$)-cycloalkyl, 4) —SO$_t$—R$^{10}$, wherein t is 1 or 2, 5) —(C$_0$-C$_6$)-alkyl-(C$_6$-C$_{14}$)-aryl, wherein the alkyl and aryl independently from one another are unsubstituted or mono-, di- or trisubstituted by R13, 6) —(C$_1$-C$_3$)-perfluoroalkyl, 7) —O—R$^{17}$, or 8) —(C$_0$-C$_6$)-alkyl-(C$_4$-C$_{15}$)-heterocyclyl, wherein alkyl and heterocyclyl independently from one another are unsubstituted or mono-, di- or trisubstituted by R13, or R11 and R12 together with the nitrogen atom to which they are bonded can form a 4- to 8-membered monocyclic heterocyclic ring which in addition to the nitrogen atom can contain one or two identical or different ring heteroatoms chosen from oxygen, sulfur and nitrogen; wherein said heterocyclic ring is unsubstituted or mono-, di- or trisubstituted independently of one another by R13;

R13 is halogen, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_3$-C$_8$)-cycloalkyl, —(C$_0$-C$_3$)-alkylene-O—R$^{10}$, —Si—(CH$_3$)$_3$, —N(R$^{10}$)—S(O)$_u$—R$^{10}$, wherein u is 1 or 2, —S—R$^{10}$, —SO$_r$—R$^{10}$, wherein r is 1 or 2, —S(O)$_v$—N(R$^{10}$)—R$^{20}$, wherein v is 1 or 2, —C(O)—R$^{10}$, —(C$_1$-C$_8$)-alkyl, —(C$_1$-C$_8$)-alkoxy, phenyl, phenyloxy, —O—CF$_3$, —(C$_0$-C$_4$)-alkyl-C(O)—O—C(R15, R16)—O—C(O)—R17, —(C$_1$-C$_4$)-alkoxy-phenyl, —(C$_0$-C$_4$)-alkyl-C(O)—O—C(R15, R16)—O—C(O)—O—R17, —(C$_1$-C$_3$)-perfluoroalkyl, —O—R15, —NH—C(O)—NH—R$^{10}$, —NH—C(O)—O—R$^{10}$, or a residue from the group consisting of

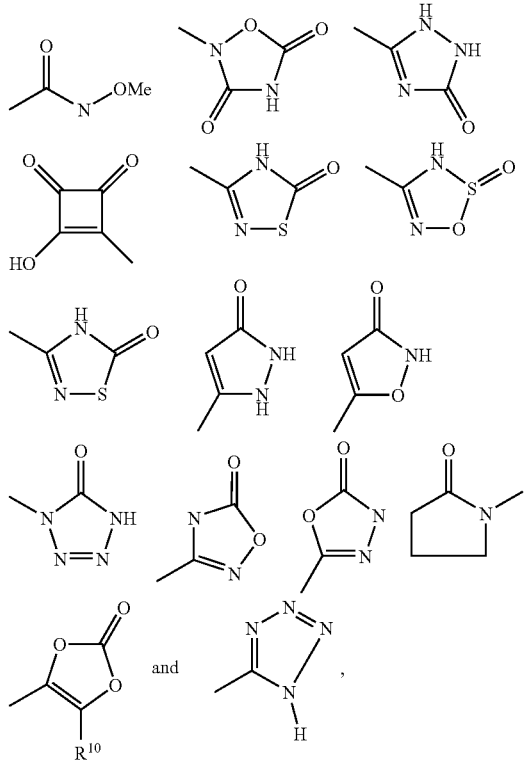

wherein Me is methyl;

R$^{10}$ and R$^{20}$ are independently of one another hydrogen, —(C$_1$-C$_6$)-alkyl, —(C$_0$-C$_4$)-alkyl-OH, —(C$_0$-C$_4$)-alkyl-O—(C$_1$-C$_4$)-alkyl or —(C$_1$-C$_3$)-perfluoroalkyl;

R15 and R16 are independently of one another hydrogen, —(C$_1$-C$_6$)-alkyl, or together with the carbon atom to which they are bonded they can form a 3- to 6 membered carbocyclic ring which is unsubstituted or substituted one to three times by R$^{10}$; and R17 is —(C$_1$-C$_6$)-alkyl, —(C$_1$-C$_6$)-alkyl-OH, —(C$_1$-C$_6$)-alkyl-O—(C$_1$-C$_6$)-alkyl, —(C$_3$-C$_8$)-cycloalkyl, —(C$_1$-C$_6$)-alkyl-O—(C$_1$-C$_8$)-alkyl-(C$_3$-C$_8$)-cycloalkyl, —(C$_1$-C$_6$)-alkyl-(C$_3$-C$_8$)-cycloalkyl, wherein the cycloalkyl is unsubstituted or substituted one, two or three times by —OH, —O—(C$_1$-C$_4$)-alkyl or R$^{10}$;

or a stereoisomer or a mixture of stereoisomers thereof in any ratio, or a physiologically tolerable salt thereof.

2. The compound according to claim 1, wherein

R3 as 25) is —(C$_0$-C$_3$)-alkylene-O—CH$_2$-(C$_1$-C$_3$)-perfluoroalkylene-CH$_2$—O—(C$_0$-C$_3$)-alkyl; and R$^{10}$ and R$^{20}$ are independently of one another hydrogen, —(C$_1$-C$_6$)-alkyl or —(C$_1$-C$_3$)-perfluoroalkyl.

3. The compound according to claim 1, wherein

R$^1$ as a monocyclic or bicyclic 6- to 14-membered aryl is phenyl, naphthyl, biphenylyl, anthryl or fluorenyl, each of which is mono-, di- or trisubstituted independently of one another by R8, or —(C$_0$-C$_3$)-alkylene-het, wherein the het is a residue selected from the group conscisting of azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, 1,2-oxa-thiepane, 1,2-oxathiolane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole and 1,2,4-triazole, wherein the het is unsubstituted or mono-, di- or trisubstituted independently of one another by R14, or $R^1$ and R3 together with the atoms to which they are bonded form azocane, azocane-2-one, 1,2-diazepine, 1,3-diazepine, 1,4-diazepine, [1,4]diazocane, [1,2]diazocan-3-one, [1,3]diazocan-2-one, dioxazine, [1,4]dioxocane, dioxole, ketopiperazine, morpholine, 1,2-oxazine, 1,3-oxazine, 1,4-oxazine, [oxocane, oxocan-2-one, piperazine, piperidine, pyran, pyrazine, pyridazine, pyrimidine or 5,6,7,8-tetrahydro-1H-azocin-2-one, each of which is unsubstituted or mono-, di- or trisubstituted independently of one another by R14, or $R^1$—N—$R^2$—V form azepine, azetidine, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, each of which is unsubstituted or mono-, di- or trisubstituted independently of one another by R14;

V is 2) phenyl, naphthyl, biphenylyl, anthryl or fluorenyl, each of which is mono-, di- or trisubstituted independently of one another by R14, or 3) acridinyl, azaindole (1H-pyrrolopyridine), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 1,4-diazepane, 4,5-dihydrooxa-zolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuiranyl, tetrahydroisochinolinyl, tetrahydrochinolinyl, 1,4,5,6-tetrahydro-pyridazinyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiopyranyl, 1,2,3-triazinyl, 1,2,3-triazolyl, 1,2,3-triazolyl, 1,2,4-triazolyl, 1,2,5-triazolyl, 1,3,4-triazolyl or xanthenyl, each of which is unsubstituted or mono-, di- or trisubstituted independently of one another by R14;

M is 1) hydrogen,
2) —($C_1$-$C_8$)-alkyl, wherein the alkyl is unsubstituted or mono-, di- or trisubstituted independently of one another by R14,
3) —C(O)—N(R11)—R12,
4) —($CH_2$)$_m$—$NR^{10}$,
5) —($C_6$-$C_{14}$)-aryl, wherein the aryl is unsubstituted or mono-, di- or trisubstituted independently of one another by R14,
6) —($C_4$-$C_{15}$)-heterocyclyl, wherein the heterocyclyl is unsubstituted or mono-, di- or trisubstituted independently of one another by R14, or
7) —($C_3$-$C_8$)-cycloalkyl, wherein the cycloalkyl is unsubstituted or mono-, di- or trisubstituted independently of one another by R14;

R3 as 25) is —($C_0$-$C_3$)-alkylene-O—$CH_2$—($C_1$-$C_3$)-perfluoroalkylene-$CH_2$—O—($C_0$-$C_3$)-alkyl, two —OR19 residues and adjacent atoms through which they are attached may form together a 1,3-dioxole ring or a 2,3-dihydro-[1,4]dioxine ring, which is substituted one, two, three or four times by R13;

R11 and R12 together with the nitrogen atom to which they are bonded may form azepine, azetidine, dioxazole, dioxazine, 1,4-diazepane, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, each of which is unsubstituted or mono-, di- or trisubstituted independently of one another by R13; and R15 and R16 are independently of one another hydrogen, —($C_1$-$C_6$)-alkyl, or together with the carbon atom to which they are bonded forrn cyclopropyl, cyclobutyl, cyclopentyl or cyclohexyl, wherein each ring is unsubstituted or substituted one to three times by $R^{10}$.

4. The compound according to claim 1, wherein
$R^1$ is hydrogen, —($C_1$-$C_4$)-alkyl, wherein the alkyl is unsubstituted or substituted one to three times by R13, —($C_1$-$C_3$)-alkylene-C(O)—NH—$R^0$, —($C_1$-$C_3$)-alkylene-C(O)—O—$R^{15}$, —($C_1$-$C_3$)-perfluoroalkylene, —$(C_1-C_3)$-alkylene-S(O)—$(C_1-C_4)$-alkyl, —$(C_1-C_3)$-alkylene-S(O)$_2$—$(C_1-C_3)$-alkyl, —$(C_1-C_3)$-alkylene-S(O)$_2$—$N(R^{4'})$—$R^{5'}$, —$(C_1-C_3)$-alkylene-O—$(C_1-C_4)$-alkyl, —$(C_0-C_3)$-alkylene-$(C_3-C_8)$-cycloalkyl, or —$(C_0-C_3)$-alkylene-het, wherein the het is azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imnidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, each of which is unsubstituted or mono-, di- or trisubstituted independently of one another by R14, or $R^1$—N—$R^2$—V form azepine, azetidine, 1,4-diazapane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, 1,4-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, each of which is unsubstituted or mono-, di- or trisubstituted independently of one another by R14;

V is 2) phenyl, wherein the phenyl is unsubstituted or mono-, di- or trisubstituted independently of one another by R14, or 3) azaindole (1H-pyrrolopyridine), azepine, azetidine, aziridine, azirine, 1,4-diazapane, 1,2-diazepine, 1,3-diazepine, 1,4-diazepine, diaziridine, diazirine, dioxazole, dioxazine, dioxole, 1,3-dioxolene, 1,3-dioxolane, furan, imidazole, imidazoline, imidazolidine, isothiazole, isothiazolidine, isothiazoline, isoxazole, isoxazoline, isoxazolidine, 2-isoxazoline, ketopiperazine, morpholine, 1,2-oxa-thiepane, 1,2-oxathiolane, 1,4-oxazepane, 1,2-oxazine, 1,3-oxazine, 1,4-oxazine, oxazole, oxaziridine, oxirane, piperazine, piperidine, pyran, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiadiazine, thiadiazole, 1,2-thiazine, 1,3-thiazine, 1,4-thiazine, 1,3-thiazole, thiazole, thiazolidine, thiazoline, thienyl, thietan, thiomorpholine, thiopyran, 1,2,3-triazine, 1,2,4-triazine, 1,3,5-triazine, 1,2,3-triazole or 1,2,4-triazole, each of which is unsubstituted or mono-, di- or trisubstituted independently of one another by R14;

M is 1) hydrogen,
2) —$(C_1-C_8)$-alkyl, wherein the alkyl is unsubstituted or mono-, di- or trisubstituted independently of one another by R14,
3) —C(O)—N(R11)—R12,
4) —$(CH_2)_m$—$NR^{10}$,
5) phenyl or naphthyl, wherein the phenyl or naphthyl are unsubstituted or mono-, di- or trisubstituted independently of one another by R14,
6) $(C_4-C_{15})$-heterocyclyl, wherein the heterocyclyl is selected from the group consisting of azepane, azepine, 1,4-diazapane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydropyridazinyl, tetrazine, tetrazole, thiadiazole, thiazole, thiophene, thiomorpholine, 1,2,3-triazine, 1,2,4-triazine, 1,3,5-triazine, 1,2,3-triazole and 1,2,4-triazole, wherein the heterocyclyl is unsubstituted or mono-, di- or trisubstituted independently of one another by R14, or
7) —$(C_3-C_8)$-cycloalkyl, wherein the cycloalkyl is unsubstituted or mono-, di- or trisubstituted independently of one another by R14;

R3 is 1) hydrogen,
2) halogen,
3) —$(C_1-C_4)$-alkyl, wherein the alkyl is unsubstituted or mono-, di- or trisubstituted independently of one another by R13,
4) —$(C_1-C_3)$-perfluoroalkyl,
5) phenyl, wherein the phenyl is unsubstituted or mono-, di- or trisubstituted independently of one another by R13,
6) —$(C_0-C_4)$-alkylene-O—R19,
8) —CN,
9) —$SO_s$—$R^{11}$, wherein s is 1 or 2,
10) —$SO_t$—$N(R^{11})$—$R^{12}$, wherein t is 1 or 2,
11) —$(C_0-C_4)$-alkylene-C(O)—$R^{11}$,
12) —$(C_0-C_4)$-alkylene-C(O)—O—$R^{11}$,
13) —$(C_0-C_4)$-alkylene-C(O)—$N(R^{11})$—$R^{12}$,
14) —$(C_0-C_4)$-alkylene-$N(R^{11})$—$R^{12}$,
15) —$NR^{10}$—$SO_2$—$R^{10}$,
17) —$(C_0-C_2)$-alkylene-C(O)—O—$(C_2-C_4)$-alkylene-O—C(O)—$(C_1-C_4)$-alkyl,
18) —C(O)—O—C(R15, R16)—O—C(O)—R17,
19) —$(C_0-C_2)$-alkylene-C(O)—O—$(C_2-C_4)$-alkylene-O—C(O)—O—$(C_1-C_6)$-alkyl,
20) —C(O)—O—C(R15, R16)—O—C(O)—O—R17,
21) —$(C_0-C_4)$-alkylene-$(C_6-C_{14})$-aryl, wherein aryl is as defined above and is mono-, di- or trisubstituted independently of one another by R13,
22) —$(C_0-C_4)$-alkylene-$(C_4-C_{15})$-heterocyclyl, wherein the heterocyclyl is unsubstituted or mono-, di- or trisubstituted independently of one another by R13,
23) —$(C_0-C_4)$-alkylene-$(C_3-C_8)$-cycloalkyl, wherein cycloalkyl is unsubstituted or mono-, di- or trisubstituted independently of one another by R13,
24) —$(C_0-C_4)$-alkylene-het, wherein the het is as defined above and is unsubstituted or mono-, di- or trisubstituted independently of one another by R13,
25) —$(C_0-C_3)$-alkylene-O—$CH_2$—$CF_2$—$CH_2$—O—$(C_0-C_3)$-alkyl, —$(C_0-C_3)$-alkylene-O—$CH_2$—$CF_2$—$CF_2$—$CH_2$—O—$(C_0-C_3)$-alkyl, or —$(C_0-C_3)$-alkylene-O—$CH_2$—$(C_1-C_3)$-perfluoroalkylene-$CH_2$—OH, 26) —SO$_w$—N(R$^{11}$)—R$^{13}$, wherein w is 1 or 2,
27) —(C$_0$-C$_4$)-alkylene-C(O)—N(R$^{11}$)—R$^{13}$,
28) —(C$_0$-C$_4$)-alkylene-N(R$^{11}$)—R$^{13}$, or
29) a residue selected from the group consisting of

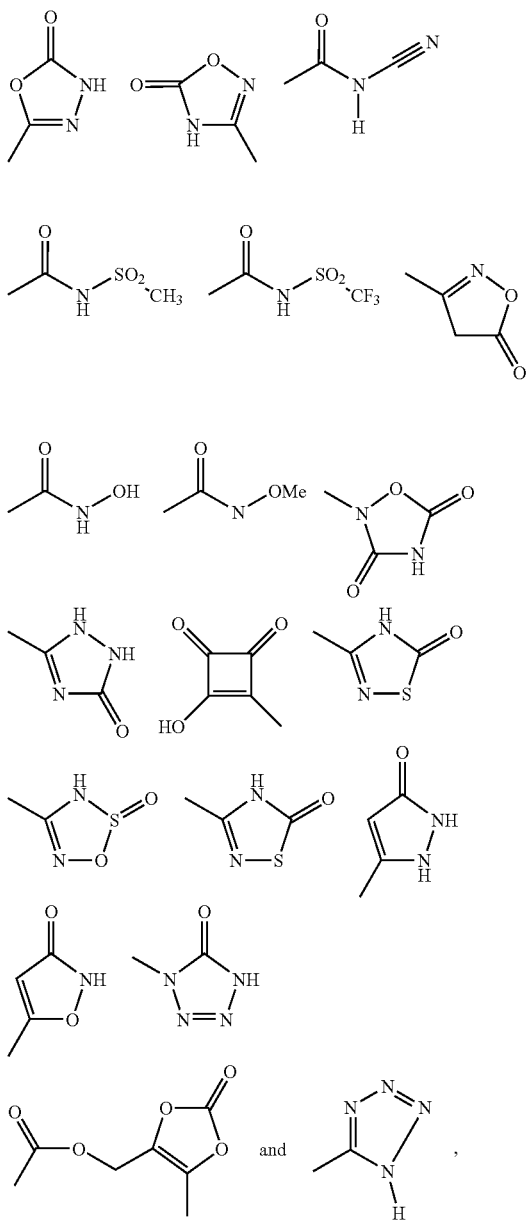

wherein Me is methyl;

two —OR19 residues and adjacent atoms through which thay are attached may form together a 1,3-dioxole ring or a 2,3-dihydro-[1,4]dioxine ring, each of which is substituted one, two, three or four times by R13;

R11 and R12 are independently of one another identical or different and are
1) hydrogen,
2) —(C$_1$-C$_6$)-alkyl, wherein the alkyl is unsubstituted or mono-, di- or trisubstituted independently of one another by R13,
5) —(C$_0$-C$_6$)-alkyl-(C$_6$-C$_{14}$)-aryl, wherein the alkyl and aryl are independently from one another unsubstituted or mono-, di- or trisubstituted by R13,
7) —O—R$^{17}$, or
8) —(C$_0$-C$_6$)-alkyl-(C$_4$-C$_{15}$)-heterocyclyl, wherein the alkyl and heterocyclyl are unsubstituted or mono-, di- or trisubstituted by R13, or R11 and R12 together with the nitrogen atom to which they are bonded form azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, 1,2,3-triazine, 1,2,4-triazine, 1,3,5-triazine, 1,2,3-triazole or 1,2,4-triazole, each of which is unsubstituted or mono-, di- or trisubstituted independently of one another by R13;

R13 is fluorine, chlorine, bromine, iodine, —NO$_2$, —CN, =O, —OH, —CF$_3$, —C(O)—O—R$^{10}$, —C(O)—N(R$^{10}$)—R$^{20}$, —N(R$^{10}$)—R$^{20}$, —(C$_0$-C$_3$)-alkylene-O—R$^{10}$, —Si—(CH$_3$)$_3$, —N(R$^{10}$)—S(O)$_2$—R$^{10}$, —S—R$^{10}$, —SO$_2$—R$^{10}$, —S(O)$_2$—N(R$^{10}$)—R$^{20}$, —C(O)—R$^{10}$, —(C$_1$-C$_8$)-alkyl, —(C$_1$-C$_8$)-alkoxy, phenyl, phenyloxy-, —O—CF$_3$, —(C$_1$-C$_3$)-perfluoroalkyl, —(C$_0$-C$_4$)-alkyl-C(O)—O—C(R15, R16)—O—C(O)—R17, —(C$_1$-C$_4$)-alkoxy-phenyl, —(C$_0$-C$_4$)-alkyl-C(O)—O—C(R15, R16)—O—C(O)—O—R17, —O—R15, —NH—C(O)—NH—R$^{10}$, —NH—C(O)—O—R$^{10}$, or a residue selected from the group consisting of

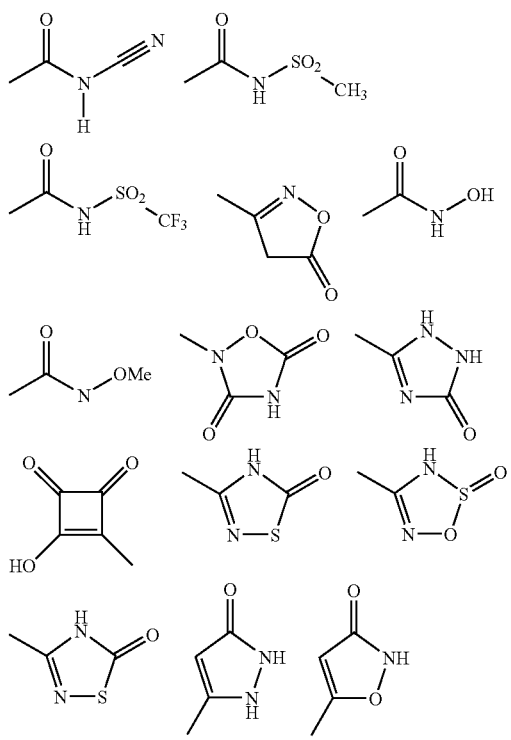

-continued

[chemical structures]

wherein Me is methyl; and

R15 and R16 are independently of one another hydrogen, —($C_1$-$C_6$)-alkyl, or together form cyclopropyl, cyclobutyl, cyclopentyl or cyclohexyl, wherein each ring is unsubstituted or substituted one to three times by $R^{10}$.

5. The compound according to claim 1, wherein $R^1$ is hydrogen, —($C_1$-$C_2$)-alkyl, —($C_1$-$C_3$)-alkylene-C(O)—NH—$R^0$, —($C_1$-$C_3$)-perfluoroalkylene, —($C_1$-$C_3$)-alkylene-C(O)—O—$R^{15}$, —($C_1$-$C_3$)-alkylene-S(O)$_2$—($C_1$-$C_3$)-alkyl or —($C_1$-$C_3$)-alkylene-S(O)$_2$—N($R^{4'}$)—$R^{5'}$, $R^2$ is a direct bond or —($C_1$-$C_2$)-alkylene, or $R^1$-N—$R^2$—V form azetidine, azetidinone, piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,4-diazepane, 1,2-diazepine, 1,3-diazepine, 1,4-diazepine, azepine, ketopiperazine, 1,4-oxazepane, oxazole, isoxazole, isoxazolidine, 2-isoxazoline, morpholine, thiazole, isothiazole, thiadiazole or thiomorpholine, each of which is unsubstituted or mono-, di- or trisubstituted independently of one another by R14;

R14 is fluorine, chlorine, —OH, =O, —($C_1$-$C_8$)-alkyl, —C(O)—OH, —CN, —NH$_2$, —C(O)—O—($C_1$-$C_4$)-alkyl, —C(O)—NH—($C_1$-$C_8$)-alkyl, —C(O)—N—[($C_1$-$C_8$)-alkyl]$_2$, —C(O)—NH$_2$ or —N($R^{18}$)—$R^{21}$, wherein $R^{18}$ and $R^{21}$ are independently from each other hydrogen, —($C_1$-$C_3$)-perfluoroalkyl or —($C_1$-$C_4$)-alkyl;

V is 2) phenyl, wherein the phenyl is unsubstituted or mono-, di- or trisubstituted independently of one another by R14, or 3) a cyclic residue selected from the group consisting of azaindole (1H-pyrrolopyridine), aziridine, azirine, azetidine, azetidinone, 1,4-diazepane, pyrrole, pyrrolidine, pyridonyl, imidazole, pyrazole, 1,2,3-triazole, 1,2,4-triazole, tetrazole, pyridine, pyrimidine, pyrazine, 1,2,3-triazine, 1,2,4-triazine, 1,3,5-triazine, tetrazine, tetrazole, azepine, diazirine, 1,2-diazepine, 1,3-diazepine, 1,4-diazepine, pyridazine, piperidine, piperazine, pyrrolidinone, ketopiperazine, furan, pyran, dioxole, 1,4-oxazepane, oxazole, isoxazole, 2-isoxazoline, isoxazolidine, morpholine, oxirane, oxaziridine, 1,3-dioxolene, 1,3-dioxolane, 1,2-oxazine, 1,3-oxazine, 1,4-oxazine, oxaziridine, thiophene, thiopyran, thietan, thiazole, isothiazole, isothiazoline, isothiazolidine, 1,2-oxathiolan, thiodiazole, thiopyran, 1,2-thiazine, 1,3-thiazole, 1,3-thiazine, 1,4-thiazine, thiadiazine and thiomorpholine, wherein sthe cyclic residue is unsubstituted or mono-, di- or trisubstituted independently of one another by R14;

G is a direct bond, —(CH$_2$)$_m$—, or —(CH$_2$)$_m$—NR$^{10}$—; m is zero, 1, 2, 3 or 4;

M is 1) hydrogen,
  2) —($C_1$-$C_6$)-alkyl, wherein the alkyl is unsubstituted or mono-, di- or trisubstituted independently of one another by R14,
  3) —C(O)—N($R^{11}$)—$R^{12}$, or
  6) heterocyclyl, wherein the heterocyclyl is selected from the group consisting of azepane, azepine, 1,4-diazepane, 1,2-diazepine, 1,3-diazepine, 1,4-diazepine, imidazole, isothiazole, isoxazole, isoxazolidine, 2-isoxazoline, ketomorpholine, ketopiperazine, morpholine, oxazole, [1,4]-oxazepane, piperazine, piperazinone, piperidine, piperidinone, pyrazine, pyridazine, pyridazinone, pyridine, pyridone, pyrimidine, pyrrolidine, pyrrolidinone, tetrahydropyran, 1,4,5,6-tetrahydro-pyridazinyl, tetrazine, tetrazole, thiadiazole, thiazole, thiomorpholine, thiophene, 1,2,3-triazine, 1,2,4-triazine, 1,3,5-triazine, 1,2,3-triazole and 1,2,4-triazole, wherein the heterocyclyl is unsubstituted or mono-, di- or trisubstituted independently of one another by R14, or 7) ($C_3$-$C_6$)-cycloalkyl;

R3 is
  1) hydrogen,
  2) halogen,
  3) —($C_1$-$C_4$)-alkyl, wherein the alkyl is unsubstituted or mono-, di- or trisubstituted independently of one another by R13,
  4) —($C_1$-$C_3$)-perfluoroalkyl,
  5) phenyl, wherein the phenyl is unsubstituted or mono-, di- or trisubstituted independently of one another by R13,
  6) —($C_0$-$C_4$)-alkylene-O—R19,
  8) —CN,
  8) —NR$^{10}$—SO$_2$—R$^{10}$,
  9) —SO$_s$—$R^{11}$, wherein s is 1 or 2,
  10) —SO$_t$—N($R^{11}$)—$R^{12}$, wherein t is 1 or 2,
  11) —($C_0$-$C_4$)-alkylene-C(O)—$R^{11}$,
  12) —($C_0$-$C_4$)-alkylene-C(O)—O—R$^{11}$,
  13) —($C_0$-$C_4$)-alkylene-C(O)—N($R^{11}$)—$R^{12}$,
  14) —($C_0$-$C_4$)-alkylene-N($R^{11}$)—$R^{12}$,
  17) —($C_0$-$C_2$)alkylene-C(O)—O—($C_2$-$C_4$)-alkylene-O—C(O)—($C_1$-$C_4$)-alkyl,
  18) —C(O)—O—C(R15, R16)—O—C(O)—R17,
  19) —($C_0$-$C_2$)alkylene-C(O)—O—($C_2$-$C_4$)-alkylene-O—C(O)—O—($C_1$-$C_6$)-alkyl,
  20) —C(O)—O—C(R15, R16)—O—C(O)—O—R17,
  25) —($C_0$-$C_3$)-alkylene-O—CH$_2$—CF$_2$—CH$_2$—O—($C_0$-$C_3$)-alkyl, —($C_0$-$C_3$)-alkylene-O—CH$_2$—CF$_2$—CF$_2$—CH$_2$—O—($C_0$-$C_3$)-alkyl, or —($C_0$-$C_3$)-alkylene-O—CH$_2$-($C_1$-$C_3$)-perfluoroalkylene-CH$_2$—OH,
  26) —SO$_w$—N($R^{11}$)—$R^{13}$, wherein w is 1 or 2,
  27) —($C_0$-$C_4$)-alkylene-C(O)—N($R^{11}$)—$R^{13}$,
  28) —($C_0$-$C_4$)-alkylene-N($R^{11}$)—$R^{13}$, or
  29) a residue selected from the group consisting of

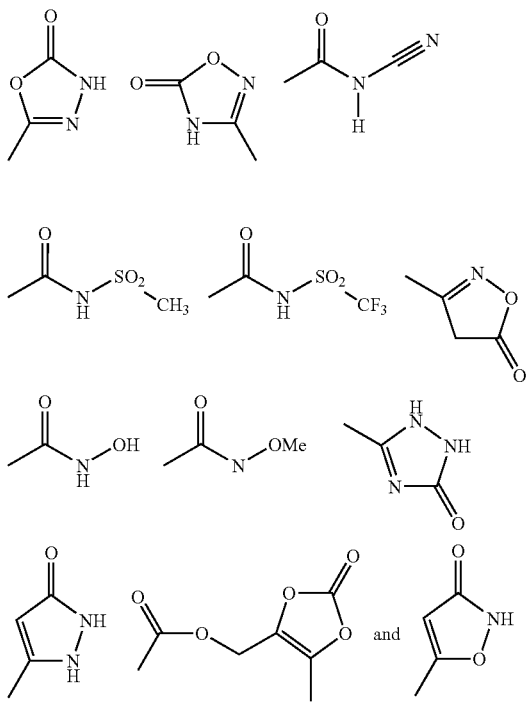

wherein Me is methyl;

two —OR19 residues and adjacent atoms through which they are attached may form a 1,3-dioxole ring or a 2,3-dihydro-[1,4]dioxine ring, each of which is substituted one, two, three or four times by R13;

$R^{11}$ and $R^{12}$ together with the nitrogen atom to which they are bonded may form azepine, azetidine, 1,4-diazepane, dioxazole, dioxazine, 1,2-diazepine, 1,3-diazepine, 1,4-diazepine, imidazole, imidazoline, imidazolidine, isothiazole, isothiazolidine, isothiazoline, isoxazole, isoxazoline, isoxazolidine, 2-isoxazoline, ketopiperazine, morpholine, [1,4]-oxazepane, oxazole, piperazine, piperidine, pyrazine, pyrazole, pyrazoline, pyrazolidine, pyridazine, pyridine, pyrimidine, pyrrole, pyrrolidine, pyrrolidinone, pyrroline, tetrahydropyridine, tetrazine, tetrazole, thiazole, thiadiazole, thiazolidine, thiazoline, thiomorpholine, thiophene, 1,2,3-triazine, 1,2,4-triazine, 1,3,5-triazine, 1,2,3-triazole or 1,2,4-triazole, each of which is unsubstituted or mono-, di- or trisubstituted independently of one another by R13;

R13 is fluorine, chlorine, —$NO_2$, —CN, =O, —OH, —$CF_3$, —C(O)—O—$R^{10}$, —C(O)—N($R^{10}$)—$R^{20}$, —N($R^{10}$)—$R^{20}$, —($C_0$-$C_3$)-alkylene-O—$R^{10}$, —Si—$(CH_3)_3$, —N($R^{10}$)—S(O)$_2$—$R^{10}$, —S—$R^{10}$, —$SO_2$—$R^{10}$, —S(O)$_2$—N($R^{10}$)—$R^{20}$, —C(O)—$R^{10}$, —($C_1$-$C_8$)-alkyl, —($C_1$-$C_8$)-alkoxy, phenyl, phenyloxy-, —O—$CF_3$, —($C_1$-$C_3$)-perfluoroalkyl, —NH—C(O)—NH—$R^{10}$, —($C_0$-$C_4$)-alkyl-C(O)—O—C(R15, R16)—O—C(O)—R17, —($C_1$-$C_4$)-alkoxy-phenyl, —($C_0$-$C_4$)-alkyl-C(O)—O—C(R15, R16)—O—C(O)—O—R17, —O—R15, —NH—C(O)—O—$R^{10}$, or a residue from the group consisting of

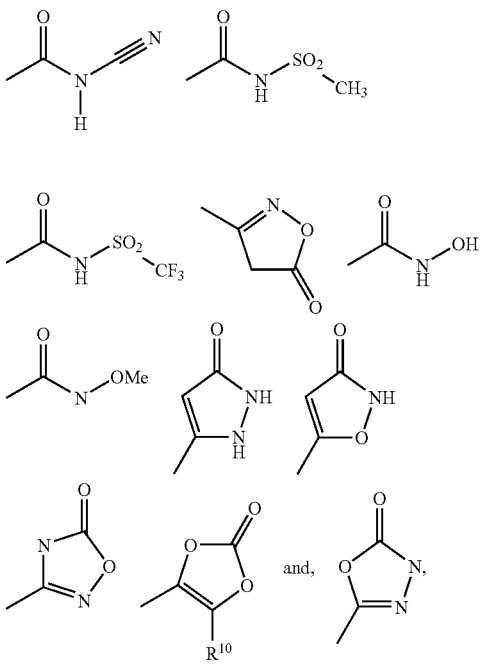

wherein Me is methyl; and

R15 and R16 are independently of one another hydrogen, —($C_1$-$C_6$)-alkyl, or together form cyclopropyl, cyclobutyl, cyclopentyl or cyclohexyl, wherein each ring is unsubstituted or substituted one to three times by $R^{10}$.

6. The compound according to claim 1, wherein $R^1$ is hydrogen or —($C_1$-$C_2$)-alkyl, $R^2$ is a direct bond or —($C_1$-$C_2$)-alkylen, or $R^1$—N—$R^2$—V form piperidine, piperazine, pyridine, pyrimidine, pyrrolidine, pyrrolidinone, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, thiadiazole or thiomorpholine, each of which is unsubstituted or mono-, di- or trisubstituted independently of one another by R14;

R14 is fluoro, chlorine, —($C_1$-$C_4$)-alkyl or —$NH_2$;

V is 2) phenyl, wherein the phenyl is unsubstituted or mono-, di- or trisubstituted independently of one another by R14, or 3) a cyclic residue selected from the group consisting of azaindolyl (1H-pyrrolopyridyl), azetidine, azepine, aziridine, azirine, 1,4-diazepane, 1,2-diazepine, 1,3-diazepine, 1,4-diazepine, diazirine, 1,3-dioxolane, dioxazole, furan, imidazole, isoquinoline, isothiazole, isothiazolidine, isothiazoline, isoxazole, 2-isoxazoline, isoxazolidine, ketopiperazine, morpholine, 1,2-oxazine, 1,3-oxazine, 1,4-oxazine, oxazole, 1,2-oxathiolan, piperidine, pyran, pyrazine, pyrazole, pyridazine, piperazine, pyridine, pyridone, pyrimidine, pyrrole, pyrrolidine, pyrrolidinone, quinazoline, quinoline, tetrazine, tetrazole, thiadiazole, 1,2-thiazine, 1,3-thiazine, 1,4-thiazine, 1,3-thiazole, thietan, thiomorpholine, thiophene, thiopyran, 1,2,3-triazine, 1,2,4-triazine, 1,3,5-triazine, 1,2,3-triazole and 1,2,4-triazole, each of which is unsubstituted or mono-, di- or trisubstituted independently of one another by R14;

G is a direct bond, —$(CH_2)_m$—, or —$(CH_2)_m$—$NR^{10}$—;

m is zero, 1, 2, 3 or 4;

M is 1) hydrogen,
2) —$(C_1$-$C_6)$-alkyl, wherein alkyl is unsubstituted or mono-, di- or trisubstituted independently of one another by R14,
3) —$C(O)$—$N(R^{11})$—$R^{12}$, or
6) heterocyclyl, wherein the heterocyclyl is selected from the group consisting of 1,4-diazepane, ketomorpholine, thiophene, pyridazone, piperidine, piperazine, pyridine, pyrimidine, pyrrolidine, pyrrolidinone, pyridonyl, imidazole, pyridazine, pyrazine, 1,2,3-triazine, 1,2,4-triazine, 1,3,5-triazine, 1,2,3-triazole, 1,2,4-triazole, tetrazine, tetrazole, 1,2-diazepine, 1,3-diazepine, 1,4-diazepine, azepine, ketopiperazine, oxazole, isoxazole, isoxazolidine, 2-isoxazoline, morpholine, thiazole, isothiazole, tetrahydropyran, 1,4,5,6-tetrahydro-pyridazinyl, thiadiazole or thiomorpholine, wherein the heterocyclyl is unsubstituted or mono-, di- or trisubstituted independently of one another by R14, or
7) $(C_3$-$C_6)$-cycloalkyl;

R3 is
1) hydrogen,
2) halogen,
3) —$(C_1$-$C_4)$-alkyl, wherein the alkyl is unsubstituted or mono-, di- or trisubstituted independently of one another by R13,
4) —$(C_1$-$C_3)$-perfluoroalkyl,
5) phenyl, wherein the phenyl is unsubstituted or mono-, di- or trisubstituted independently of one another by R13,
6) —$(C_0$-$C_4)$-alkylene-O—$R^{19}$,
8) —CN,
8) —$NR^{10}$—$SO_2$—$R^{10}$,
9) —$SO_s$—$R^{11}$, wherein s is 1 or 2,
10) —$SO_t$—$N(R^{11})$—$R^{12}$, wherein t is 1 or 2,
11) —$(C_0$-$C_4)$-alkylene-$C(O)$—$R^{11}$,
12) —$(C_0$-$C_4)$-alkylene-$C(O)$—O—$R^{11}$,
13) —$(C_0$-$C_4)$-alkylene-$C(O)$—$N(R^{11})$—$R^{12}$,
14) —$(C_0$-$C_4)$-alkylene-$N(R^{11})$—$R^{12}$,
17) —$(C_0$-$C_2)$alkylene-$C(O)$—O—$(C_2$-$C_4)$-alkylene-O—$C(O)$—$(C_1$-$C_4)$-alkyl,
18) —$C(O)$—O—$C(R15, R16)$—O—$C(O)$—$R^{17}$,
19) —$(C_0$-$C_2)$alkylene-$C(O)$—O—$(C_2$-$C_4)$-alkylene-O—$C(O)$—O—$(C_1$-$C_6)$-alkyl,
20) —$C(O)$—O—$C(R15, R16)$—O—$C(O)$—O—$R^{17}$,
26) —$(C_0$-$C_3)$-alkylene-O—$CH_2$—$CF_2$—$CH_2$—O—$(C_0$-$C_3)$-alkyl, —$(C_0$-$C_3)$-alkylene-O—$CH_2$—$CF_2$—$CF_2$—$CH_2$—O—$(C_0$-$C_3)$-alkyl, or —$(C_0$-$C_3)$-alkylene-O—$CH_2$-$(C_1$-$C_3)$-perfluoroalkylene-$CH_2$—OH,
26) —$SO_w$—$N(R^{11})$—$R^{13}$, wherein w is 1 or 2,
27) —$(C_0$-$C_4)$-alkylene-$C(O)$—$N(R^{11})$—$R^{13}$,
28) —$(C_0$-$C_4)$-alkylene-$N(R^{11})$—$R^{13}$, or
29) a residue selected from the group consisting of wherein Me is methyl;

R19 is a) hydrogen,
b) —$(C_1$-$C_4)$-alkyl, wherein the alkyl is unsubstituted or mono-, di- or trisubstituted independently of one another by R13, or
c) phenyl, wherein the phenyl is unsubstituted or mono-, di- or trisubstituted independently of one another by R13,
d) —$CF_3$, or
e) —$CHF_2$;

R11 and R12 are independently of one another identical or different and are
1) hydrogen,
2) —$(C_1$-$C_4)$-alkyl, wherein the alkyl is unsubstituted or mono-, di- or trisubstituted independently of one another by R13,
3) —$(C_0$-$C_6)$-alkyl-$(C_3$-$C_6)$-cycloalkyl,
7) —O—$R^{17}$, or
8) —$(C_0$-$C_6)$-alkyl-$(C_4$-$C_{15})$-heterocyclyl, wherein the alkyl and heterocyclyl independently from one another are unsubstituted or mono-, di- or trisubstituted by R13 and wherein the heterocyclyl azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine, or R11 and R12 together with the nitrogen atom to which they are bonded form azetidine, cyclopropyl, cyclobutyl, 4,5-dihydro-oxazole, imidazolidine, morpholine, (1,4)-oxazepane, oxazolidine, piperidine, piperazine, pyrrolidine, tetrahydrothiophene, thiazolidine or thiomorpholine;

R13 is fluorine, —CN, =O, —OH, —$CF_3$, —$C(O)$—O—$R^{10}$, —$C(O)$—$N(R^{10})$—$R^{20}$, —$N(R^{10})$—$R^{20}$, —$(C_3$-$C_6)$-cycloalkyl, —$(C_0$-$C_3)$-alkylene-O—$R^{10}$, —Si—$(CH_3)_3$, —S—$R^{10}$, —$SO_2$—$R^{10}$, —$(C_1$-$C_3)$-perfluoroalkyl, or a residue selected from the group consisting of

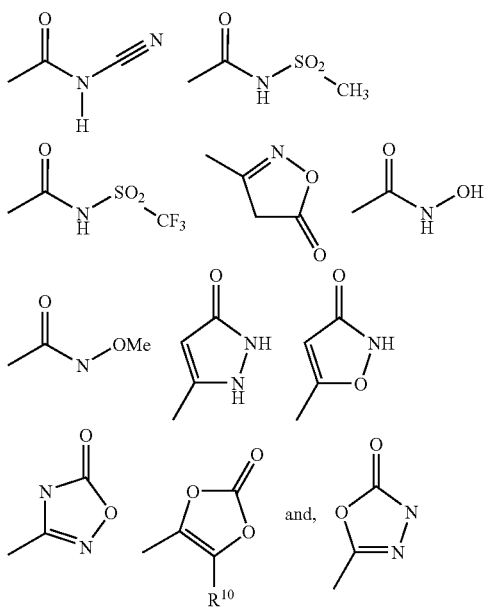

wherein Me is methyl;

R$^{10}$ and R$^{20}$ are independently of one another hydrogen, —(C$_1$-C$_4$)-alkyl or —(C$_1$-C$_3$)-perfluoroalkyl; and R$^{15}$ and R$^{16}$ are independently of one another hydrogen, —(C$_1$-C$_4$)-alkyl, or together form cyclopropyl, cyclobutyl, cyclopentyl or cyclohexyl, wherein each ring is unsubstituted or substituted one to three times by R$^{10}$.

7. The compound according to claim 1, wherein

R$^1$ is hydrogen,

R$^2$ is a direct bond or methylene, or

R$^1$—N—R$^2$—V form azetidine, pyrrolidine, piperidine or piperazine;

R14 is fluorine, chlorine, methyl, ethyl, =O, —SO$_2$—CH$_3$ or —NH$_2$;

V is 2) phenyl, wherein phenyl is unsubstituted or mono- or disubstituted independently of one another by R14, or 3) azaindolyl (1H-pyrrolopyridyl), azetidine, 1,4-diazepane, isoxazole, isoquinoline, piperazine, piperidine, pyrazine, pyridazine, pyrimidine, pyrrolidine, quinazoline, quinoline or tetrahydropyrane, each of which is unsubstituted or mono- or disubstituted independently of one another by R14;

G is a direct bond, —(CH$_2$)$_m$—, —C(O)— or —(CH$_2$)$_m$—NR$^{10}$—;

m is zero, 1 or 2;

M is 1) hydrogen, 2) (C$_2$-C$_4$)-alkyl, wherein the alkyl is unsubstituted or mono- or disubstituted independently of one another by R14, or 6) azepanyl, cyclopropyl, cyclobutyl, cyclopentyl, cyclohexyl, imidazolyl, ketomorpholinyl, morpholinyl, [1,4]Oxazepanyl, piperidinyl, phenyl, piperidonyl, pyrazinyl, pyrazolyl, pyridazinyl, pyridyl, pyrimidyl, pyrrolidinyl, 1,4,5,6-tetrahydro-pyridazinyl, or tetrahydropyranyl, each of which is unsubstituted or mono- or disubstituted independently of one another by R14;

R3 is 1) hydrogen,
2) F or C,
3) —(C$_1$-C$_4$)-alkyl, wherein the alkyl is unsubstituted or mono-, di- or trisubstituted independently of one another by R13,
4) —(C$_1$-C$_3$)-perfluoroalkyl,
5) phenyl, wherein the phenyl is unsubstituted or mono-, di- or trisubstituted independently of one another by R13,
6) —(C$_0$-C$_2$)-alkylene-O—R19,
8) —CN,
9) —SO$_s$—R$^{11}$, wherein s is 1 or 2,
10) —SO$_t$—N(R$^{11}$)—R$^{12}$, wherein t is 1 or 2,
11) —(C$_0$-C$_4$)-alkylene-C(O)—R$^{11}$,
12) —(C$_0$-C$_4$)-alkylene-C(O)—O—R$^{11}$,
13) —(C$_0$-C$_4$)-alkylene-C(O)—N(R$^{11}$)—R$^{12}$,
14) —(C$_0$-C$_4$)-alkylene-N(R$^{11}$)—R$^{12}$,
15) —NR$^{10}$—SO$_2$—R$^{10}$,
17) —(C$_0$-C$_2$)alkylene-C(O)—O—(C$_2$-C$_4$)-alkylene-O—C(O)—(C$_1$-C$_4$)-alkyl,
18) —C(O)—O—C(R15, R16)—O—C(O)—R17,
19) —(C$_0$-C$_2$)alkylene-C(O)—O—(C$_2$-C$_4$)-alkylene-O—C(O)—O—(C$_1$-C$_6$)-alkyl,
20) —C(O)—O—C(R15, R16)—O—C(O)—O—R17,
27) —(C$_0$-C$_4$)-alkylene-C(O)—N(R$^{11}$)—R$^{13}$ or
29) a residue selected from the group consisting of

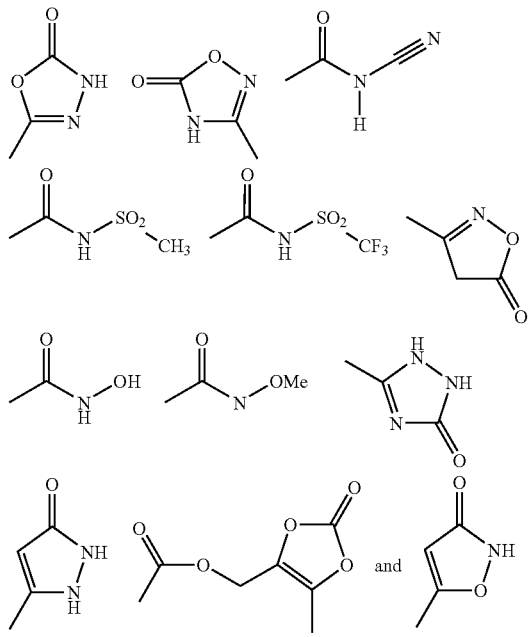

wherein Me is methyl;

R19 is a) hydrogen, b) —(C$_1$-C$_4$)-alkyl, wherein the alkyl is unsubstituted or mono-, di- or trisubstituted independently of one another by R13, or c) phenyl, wherein the phenyl is unsubstituted or mono-, di- or trisubstituted independently of one another by R13, d) —CF$_3$, or e) —CHF$_2$;

R11 and R12 are independently of one another identical or different and are 1) hydrogen,
2) —($C_1$-$C_4$)-alkyl, wherein the alkyl is unsubstituted or mono-, di- or trisubstituted independently of one another by R13,
3) —($C_0$-$C_6$)-alkyl-($C_3$-$C_6$)-cycloalkyl,
7) —O—$R^{17}$, or
8) —($C_0$-$C_6$)-alkyl-($C_6$-$C_{15}$)-heterocyclyl, wherein the alkyl and heterocyclyl independently from one another are unsubstituted or mono-, di- or trisubstituted by R13 and wherein the heterocyclyl is azetidine, imidazolidine, morpholine, 4,5-dihydro-[1,2,4]oxadiazole, -[1,3]dioxole, (1,4)-oxazepane or pyrrolidine, or R11 and R12 together with the nitrogen atom to which they are bonded form azetidine, imidazolidine, morpholine, (1,4)-oxazepane piperazine, piperidine, pyrrolidine or thiomorpholine;

R13 is fluorine, —CN, =O, —OH, —$CF_3$, —C(O)—O—$R^{10}$, —C(O)—N($R^{10}$)—$R^{20}$, —N($R^{10}$)—$R^{20}$, —($C_3$-$C_6$)-cycloalkyl, —($C_0$-$C_3$)-alkylene-O—$R^{10}$, —Si—($CH_3$)$_3$, —S—$R^{10}$, —$SO_2$—$R^{10}$, —$SO_2$—NH, —($C_1$-$C_3$)-perfluoroalkyl, —($C_1$-$C_3$)-alkyl, or a residue selected from the group consisting of

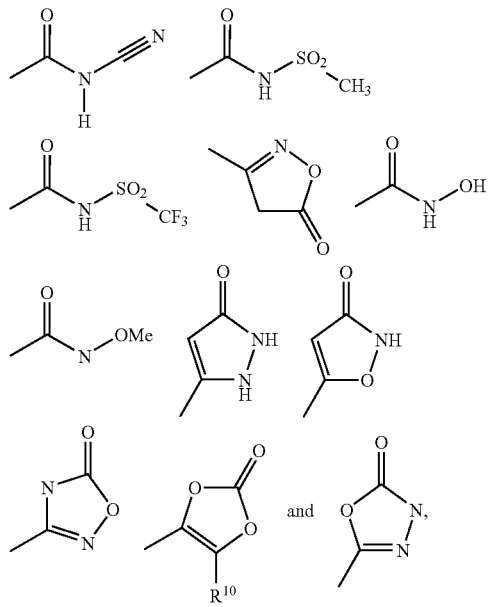

wherein Me is methyl;

$R^{10}$ and $R^{20}$ are independently of one another hydrogen, —($C_1$-$C_4$)-alkyl or —($C_1$-$C_3$)-perfluoroalkyl; and $R^{15}$ and $R^{16}$ are independently of one another hydrogen, —($C_1$-$C_4$)-alkyl, or together form cyclopropyl, cyclobutyl, cyclopentyl or cyclohexyl, wherein each ring is unsubstituted or substituted one to three times by $R^{10}$.

8. The compound according to claim 1, wherein the compound is

1-[5-(5-Chloro-thiophen-2-yl)-isoxazol-3-ylmethyl]-3-(1-isopropyl-piperidin-4-ylcarbamoyl)-1H-indazole-5-carboxylic acid methyl ester, 1-[5-(5-Chloro-thiophen-2-yl)-isoxazol-3-ylmethyl]-3-(1-isopropyl-piperidin-4-ylcarbamoyl)-1H-indazole-6-carboxylic acid methyl ester, 1-[5-(5-Chloro-thiophen-2-yl)-isoxazol-3-ylmethyl]-3-(1-isopropyl-piperidin-4-ylcarbamoyl)-1H-indazole-7-carboxylic acid methyl ester, 1-[5-(5-Chloro-thiophen-2-yl)-isoxazol-3-ylmethyl]-3-(1-isopropyl-piperidin-4-ylcarbamoyl)-1H-indazole-5-carboxylic acid, 1-[5-(5-Chloro-thiophen-2-yl)-isoxazol-3-ylmethyl]-3-(1-isopropyl-piperidin-4-ylcarbamoyl)-1H-indazole-7-carboxylic acid, 1-[5-(5-Chloro-thiophen-2-yl)-isoxazol-3-ylmethyl]-3-(1-isopropyl-piperidin-4-ylcarbamoyl)-1H-indazole-6-carboxylic acid, Indazole-1,3-dicarboxylic acid 1-[(5-chloro-pyridin-2-yl)-amide]3-[(1-isopropyl-piperidin-4-yl)-amide], 1-[5-(5-Chloro-thiophen-2-yl)-isoxazol-3-ylmethyl]-1H-indazole-3-carboxylic acid (1-isopropyl-piperidin-4-yl)-amide, 1-[5-(5-Chloro-thiophen-2-yl)-isoxazol-3-ylmethyl]-3-(1-isopropyl-piperidin-4-ylcarbamoyl)-1H-indazole-5-carboxylic acid 1-ethoxycarbonyloxy-ethyl ester, 1-[5-(5-Chloro-thiophen-2-yl)-isoxazol-3-ylmethyl]-4-cyano-1H-indazole-3-carboxylic acid (1-isopropyl-piperidin-4-yl)-amide, 1-[5-(5-Chloro-thiophen-2-yl)-isoxazol-3-ylmethyl]-4-(5-oxo-4,5-dihydro-[1,2,4]oxadiazol-3-yl)-1H-indazole-3-carboxylic acid (1-isopropyl-piperidin-4-yl)-amide, 5-(Azetidine-1-carbonyl)-1-[5-(5-chloro-thiophen-2-yl)-isoxazol-3-ylmethyl]-1H-indazole-3-carboxylic acid (1-isopropyl-piperidin-4-yl)-amide, 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-methanesulfonyl-ethyl)-amide], 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-sulfamoyl-ethyl)-amide], 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2-morpholin-4-yl-ethyl)-amide], 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-trimethylsilanylmethyl-amide, 1-[5-(5-Chloro-thiophen-2-yl)-isoxazol-3-ylmethyl]-1H-indazole-3,5-dicarboxylic acid 5-[bis-(2-hydroxy-ethyl)-amide]3-[(1-isopropyl-piperidin-4-yl)-amide], 1-[5-(5-Chloro-thiophen-2-yl)-isoxazol-3-ylmethyl]-1H-indazole-3,5-dicarboxylic acid 5-[(2-hydroxy-ethyl)-methyl-amide]3-[(1-isopropyl-piperidin-4-yl)-amide], {[1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid ethyl ester, 1-[5-(5-Chloro-thiophen-2-yl)-isoxazol-3-ylmethyl]-1H-indazole-3,5-dicarboxylic acid 5-[(2,2-difluoro-ethyl)-amide]3-[(1-isopropyl-piperidin-4-yl)-amide], 1-[5-(5-Chloro-thiophen-2-yl)-isoxazol-3-ylmethyl]-1H-indazole-3,5-dicarboxylic acid 5-carbamoylmethyl-amide 3-[(1-isopropyl-piperidin-4-yl)-amide], 1-[5-(5-Chloro-thiophen-2-yl)-isoxazol-3-ylmethyl]-1H-indazole-3,5-dicarboxylic acid 5-[(2-hydroxy-ethyl)-amide]3-[(1-isopropyl-piperidin-4-yl)-amide], 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-{[2-(2-oxo-imidazolidin-1-yl)-ethyl]-amide}, 1-[5-(5-Chloro-thiophen-2-yl)-isoxazol-3-ylmethyl]-1H-indazole-3,5-dicarboxylic acid 5-[(2-hydroxy-1-hydroxymethyl-1-methyl-ethyl)-amide]3-[(1-isopropyl-piperidin-4-yl)-amide], {[1-[5-(5-Chloro-thiophen-2-yl)-isoxazol-3-ylmethyl]-3-(1-isopropyl-piperidin-4-ylcarbamoyl)-1H-indazole-5-carbonyl]-amino}-acetic acid, 1-[1-[5-(5-Chloro-thiophen-2-yl)-isoxazol-3-ylniethyl]-3-(1-isopropyl-piperidin-4-ylcarbamoyl)-1H-indazole-5-carbonyl]-(2S)-azetidine-2-carboxylic acid, 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-[(2,2,2-trifluoro-ethyl)-amide], {[1-[5-(5-Chloro-thiophen-2-yl)-isoxazol-3-ylmethyl]-3-(1-isopropyl-piperidin-4-ylcarbamoyl)-1H-indazole-5-carbonyl]-methyl-amino}-acetic acid, 1-[5-(5-Chloro-thiophen-2-yl)-isoxazol-3-ylmnethyl]-3-(1-isopropyl-piperidin-4-ylcarbamoyl)-1H-indazole-5-carboxylic acid 2-hydroxy-ethyl ester, 1-[5-(5-Chloro-thiophen-2-yl)-isoxazol-3-ylmethyl]-5-([1,4]oxazepane-4-carbonyl)-1H-indazole-3-carboxylic acid (1-isopropyl-piperidin-4-yl)-amide, 1-[5-(5-Chloro-thiophen-2-yl)-isoxazol-3-ylmethyl]-5-(3-hydroxy-azetidine-1-carbonyl)-1H-indazole-3-carboxylic acid (1-isopropyl-piperidin-4-yl)-amide, 1-[5-(5-Chloro-thiophen-2-yl)-isoxazol-3-ylmethyl]-1H-indazole-3,5-dicarboxylic acid 3-[(1-isopropyl-piperidin-4-yl)-amide]5-(methoxy-amide), 1-[5-(5-Chloro-thiophen-2-yl)-isoxazol-3-ylmethyl]-1H-indazole-3-carboxylic acid [4-(pyrrolidine-1-carbonyl)-phenyl]-amide, 1-[5-(5-Chloro-thiophen-2-yl)-isoxazol-3-ylmethyl]-1H-indazole-3-carboxylic acid [4-(morpholine-4-carbonyl)-phenyl]-amide, 1-(1-{1-[5-(5-Chloro-thiophen-2-yl)-isoxazol-3-ylmethyl]-1H-indazole-3-carbonyl}-piperidin-4-yl)-pyrrolidin-2-one, 1-[5-(5-Chloro-thiophen-2-yl)-isoxazol-3-ylmethyl]-1H-indazole-3-carboxylic acid [4-(2-oxo-pyrrolidin-1-yl)-phenyl]-amide, 1-[5-(5-Chloro-thiophen-2-yl)-isoxazol-3-ylmethyl]-1H-indazole-3-carboxylic acid (2'-methanesulfonyl-biphenyl-4-yl)-amide, 1-[5-(5-Chloro-thiophen-2-yl)-isoxazol-3-ylmethyl]-1H-indazole-3-carboxylic acid [4-(4-methyl-6-oxo-1,4,5,6-tetrahydro-pyridazin-3-yl)-phenyl]-amide, 1-[5-(5-Chloro-thiophen-2-yl)-isoxazol-3-ylmethyl]-1H-indazole-3-carboxylic acid (4-morpholin-4-yl-phenyl)-amide, 1-[5-(5-Chloro-thiophen-2-yl)-isoxazol-3-ylmethyl]-1H-indazole-3-carboxylic acid [4-(1H-imidazol-4-yl)-phenyl]-amide, 1-[5-(5-Chloro-thiophen-2-yl)-isoxazol-3-ylmethyl]-1H-indazole-3-carboxylic acid (4-piperidin-1-yl-phenyl)-amide, 1-[5-(5-Chloro-thiophen-2-yl)-isoxazol-3-ylmethyl]-3-[4-(3-oxo-morpholin-4-yl)-phenylcarbamoyl]-1H-indazole-5-carboxylic acid methyl ester, 1-[5-(5-Chloro-thiophen-2-yl)-isoxazol-3-ylmethyl]-3-(1-isopropyl-piperidin-4-ylcarbamoyl)-1H-indazole-5-carboxylic acid 5-methyl-2-oxo-[1,3]dioxol-4-ylmethyl ester, 1-[5-(5-Chloro-thiophen-2-yl)-isoxazol-3-ylmethyl]-5-(cyanamide-1-carbonyl)-1H-indazole-3-carboxylic acid (1-isopropyl-piperidin-4-yl)-amide, 1-[1-[5-(5-Chloro-thiophen-2-yl)-isoxazol-3-ylmethyl]-3-(1-isopropyl-piperidin-4-ylcarbamoyl)-1H-indazole-5-carbonyl]-azetidine-3-carboxylic acid, 1-[5-(5-Chloro-thiophen-2-yl)-isoxazol-3-ylmethyl]-1H-indazole-3-carboxylic acid [4-(4-oxo4H-pyridin-1-yl)-phenyl]-amide, or 1-[5-(5-Chloro-thiophen-2-yl)-isoxazol-3-ylmethyl]-3-(1-isopropyl-piperidin-4-ylcarbamoyl)-1H-indazole-5-carboxylic acid 2-methoxy-ethyl ester.

9. A process for the preparation of a compound according to claim 1, wherein $J_1$ is N and $J_2$ is N—Q—$R^0$, which comprises condensing a compound of the formula 7 with a compound of the formula $HR^{8'}$ to give a compound of the formula 8 and converting the compound of the formula 8 into a compound of the formula I, wherein $J_1$ is N and $J_2$ is N—Q—$R^0$,

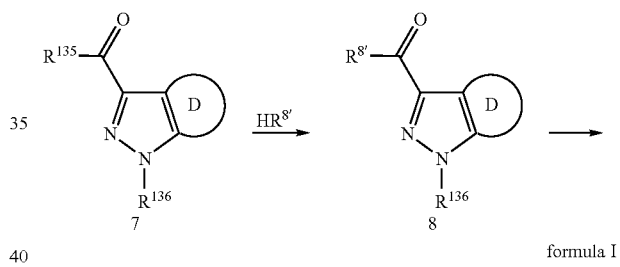

formula I wherein the residue $R^{8'}$ has the donation of —N($R^1$)—$R^2$—V-G-M as indicated in claim 1, and where the residue $R^{136}$ denotes the group -Q-$R^0$, and where the group —C(O)—$R^{135}$ is a carboxylic acid group.

10. A pharmaceutical composition comprising at least one compound according to claim 1 and a pharmaceutically acceptable carrier.

11. A method for treating thrombosis, comprising administering to the patient a pharmaceutically effective amount of a compound according to claim 1.

* * * * *